US008626274B2

(12) United States Patent (10) Patent No.: US 8,626,274 B2
Chiu et al. (45) Date of Patent: Jan. 7, 2014

(54) METHODS, SYSTEMS AND DEVICES FOR DETECTING AND DIAGNOSING HEART DISEASES AND DISORDERS

(75) Inventors: Wei-Min Brian Chiu, El Monte, CA (US); Chi-Jen Tseng, Kaohsiung County (TW)

(73) Assignee: Dynacardia, Inc., Azusa, CA (US)

( * ) Notice: Subject to any disclaimer, the term of this patent is extended or adjusted under 35 U.S.C. 154(b) by 0 days.

(21) Appl. No.: 13/141,921

(22) PCT Filed: Dec. 31, 2008
(Under 37 CFR 1.47)

(86) PCT No.: PCT/US2008/088594
§ 371 (c)(1),
(2), (4) Date: Mar. 2, 2012

(87) PCT Pub. No.: WO2010/077246
PCT Pub. Date: Jul. 8, 2010

(65) Prior Publication Data
US 2012/0330170 A1 Dec. 27, 2012

Related U.S. Application Data

(63) Continuation-in-part of application No. 11/774,688, filed on Jul. 9, 2007, now Pat. No. 7,869,864.

(51) Int. Cl.
*A61B 5/0452* (2006.01)
(52) U.S. Cl.
USPC .............................. 600/509; 600/512; 600/515
(58) Field of Classification Search
USPC .......................................... 600/509, 512, 515
See application file for complete search history.

(56) References Cited

U.S. PATENT DOCUMENTS

| | | | |
|---|---|---|---|
| 3,616,791 A | 11/1971 | Harris | |
| 4,041,468 A | 8/1977 | Perry | |
| 4,947,857 A | 8/1990 | Albert | |
| 5,092,341 A | 3/1992 | Kelen | |
| 5,609,158 A | 3/1997 | Chan | |
| 5,649,544 A | 7/1997 | Feng | |
| 6,148,228 A | 11/2000 | Fang | |
| 6,263,243 B1 | 7/2001 | Lang | |
| 6,638,232 B1 | 10/2003 | Fang | |
| 7,343,198 B2 | 3/2008 | Behbehani | |
| 7,412,283 B2 | 8/2008 | Ginzburg | |
| 2002/0120206 A1 | 8/2002 | Taha | |
| 2005/0027202 A1 | 2/2005 | Ginzburg | |
| 2006/0281996 A1 | 12/2006 | Kuo | |

OTHER PUBLICATIONS

International Search Report received in PCT/US2008/088594 mailed May 15, 2009.
Notification of Transmittal of the International Search Report and the Written Opinion of the International Searching Authority received in PCT/US2008/068731 mailed Oct. 19, 2010.
International Search Report received in PCT/US2008/068731 mailed Oct. 19, 2010.
Written Opinion of the International Searching Authority received in PCT/US2008/068731 mailed Oct. 19, 2010.

*Primary Examiner* — Joseph Dietrich
(74) *Attorney, Agent, or Firm* — Suzannah K. Sundby; Smith, Gambrell & Russell, LLP

(57) ABSTRACT

Disclosed herein methods, devices, and systems for detecting and diagnosing a heart disease or disorder in a subject from a prime electrocardiogram which comprises calculating at least one distribution function of the prime electrocardiogram and determining whether the distribution function is indicative of the presence of absence of the heart disease or disorder.

20 Claims, 28 Drawing Sheets

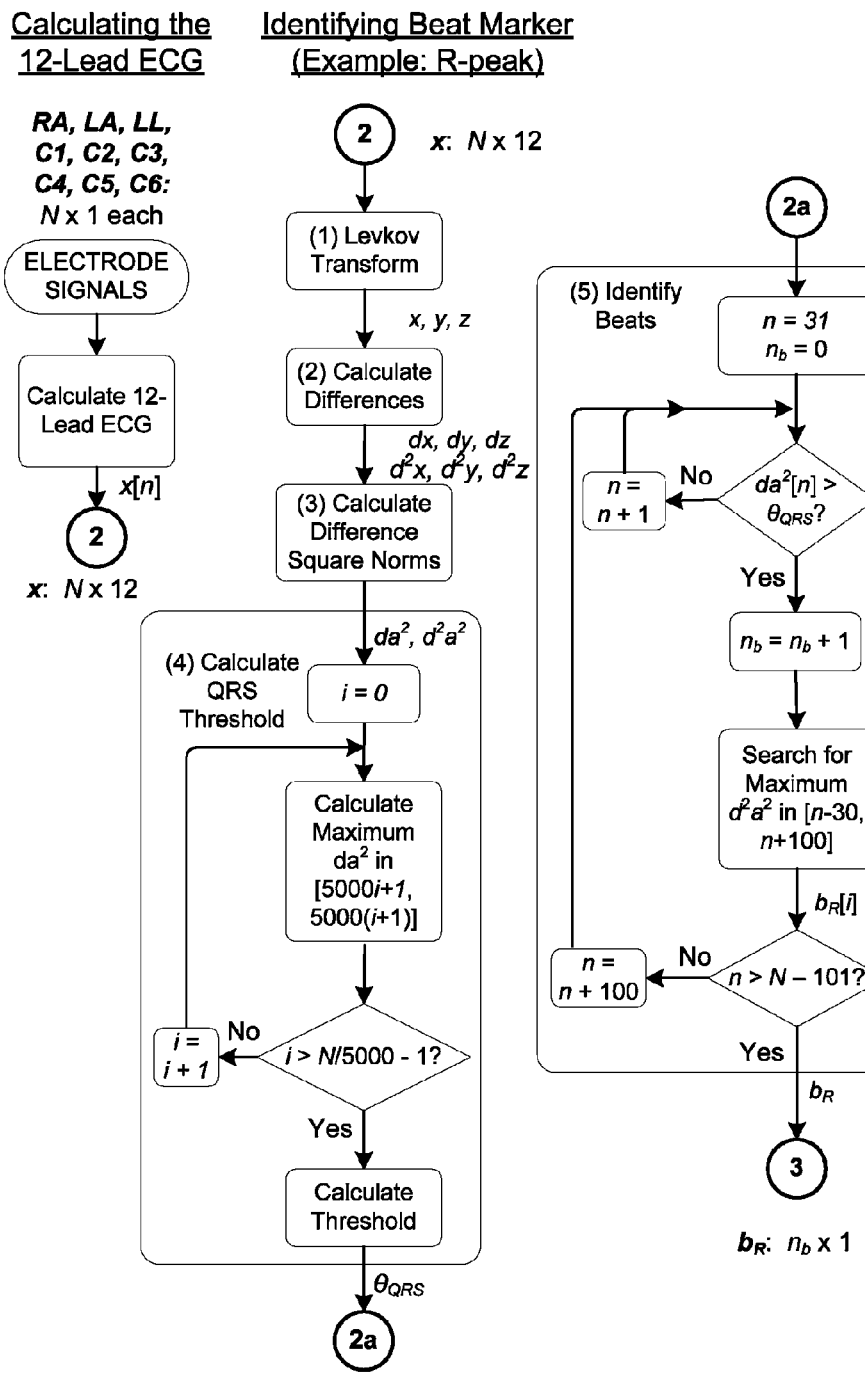
Figure 18A1

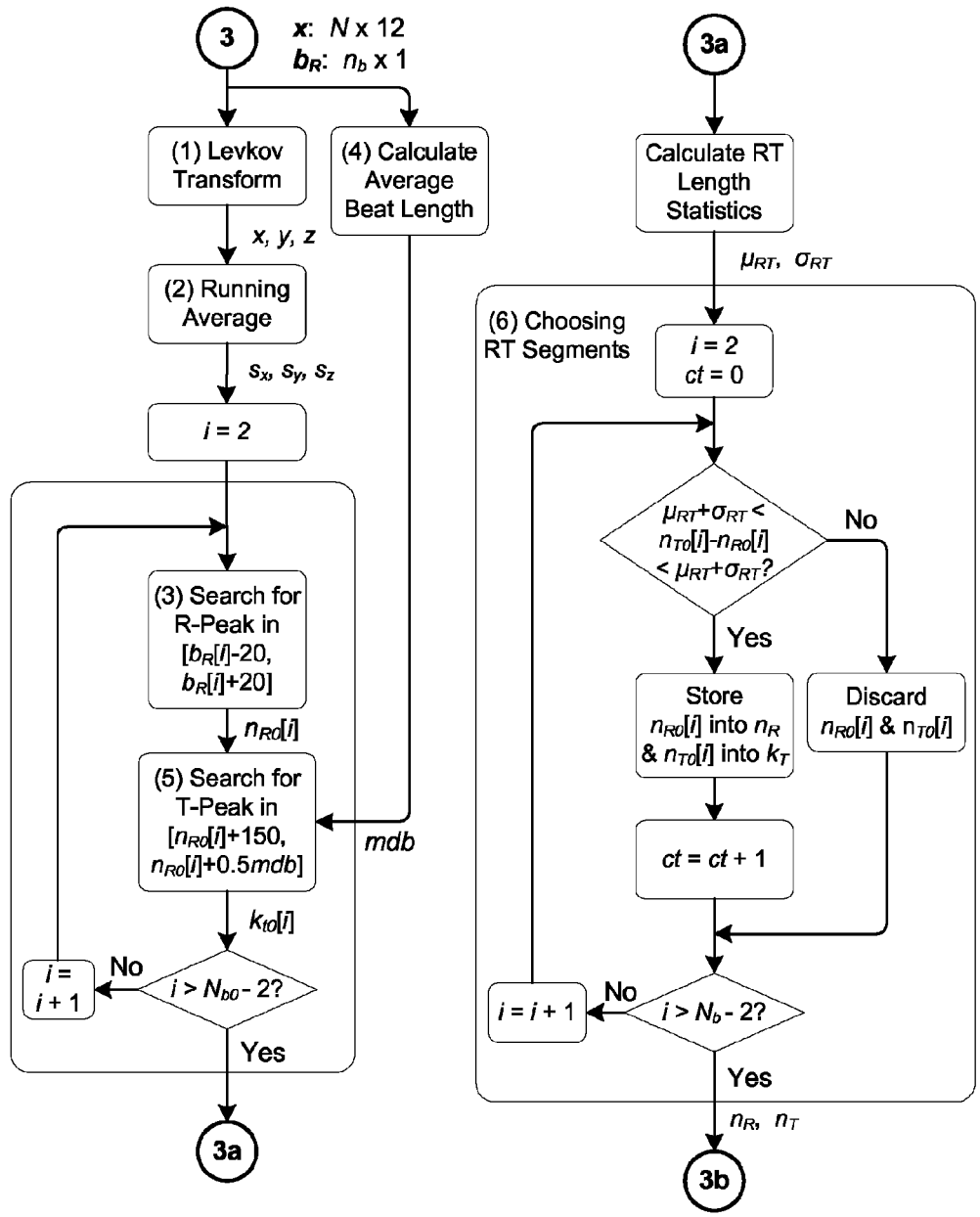
Figure 18A2

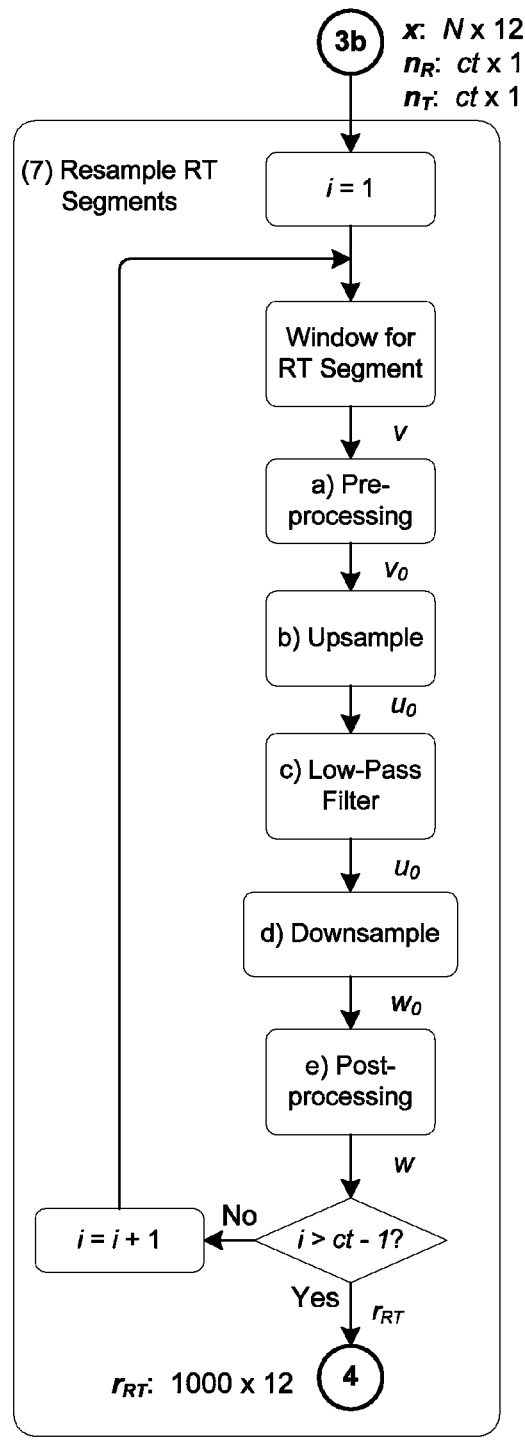
Figure 18A2 cont.

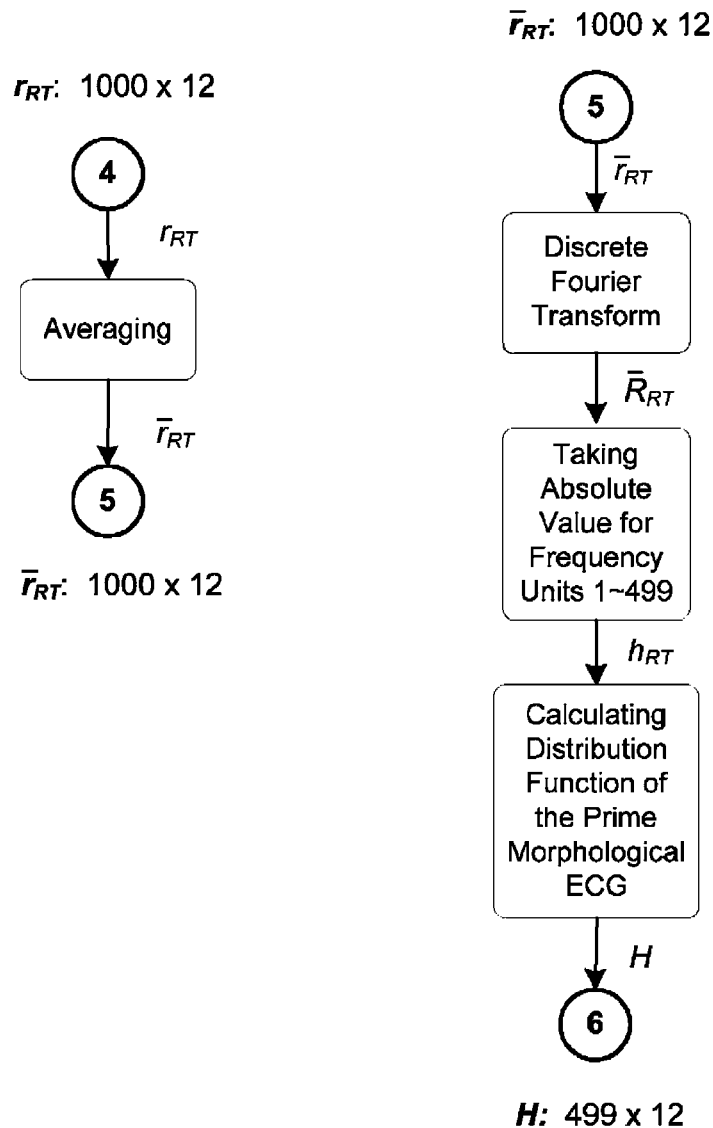
Figure 18A3

Data Acquisition and Storage
The PC-ECG data acquisition hardware stores $N: 90000 \sim 120000$ simultaneous samples of the 9 electrode signals $\{RA[n], LA[n], LL[n], C1[n], C2[n], C3[n], C4[n], C5[n], C6[n]\}$ at 12 bits precision and 1000 samples per second.

Calculating the 12-Lead ECG
*"Electrode Signals" to "2" shown in Figure 18A1*

(1) Calculate 12-Lead ECG, $n = 1,3,\cdots,N$
$$I[n] = LA[n] - RA[n]$$
$$I[n] = LL[n] - RA[n]$$
$$I[n] = LL[n] - LA[n]$$
$$aVR[n] = RA[n] - (LA[n] + LL[n])/2$$
$$aVL[n] = LA[n] - (RA[n] + LL[n])/2$$
$$aVF[n] = LL[n] - (RA[n] + LA[n])/2$$
$$V1[n] = C1[n] - (RA[n] + LA[n] + LL[n])/3$$
$$V2[n] = C2[n] - (RA[n] + LA[n] + LL[n])/3$$
$$V3[n] = C3[n] - (RA[n] + LA[n] + LL[n])/3$$
$$V4[n] = C4[n] - (RA[n] + LA[n] + LL[n])/3$$
$$V5[n] = C5[n] - (RA[n] + LA[n] + LL[n])/3$$
$$V6[n] = C6[n] - (RA[n] + LA[n] + LL[n])/3$$

Identifying Beat Marker (Example: R-peak)
*"2" to "3" shown in Figure 18A1*

(1) Levkov Transform: (from 12-lead ECG to 3-lead Frank ECG)
$$x = 0.0592I - 0.0877II - 0.1761V1 - 0.0771V2 + 0.1228V3 + 0.2432V4 + 0.2560V5 + 0.2078V6$$

$$y = 0.3827I + 0.4563II - 0.0179V1 - 0.0436V2 - 0.0490V3 + 0.0165V4 + 0.0541V5 + 0.0555V6$$

$$z = 0.0638I + 0.0258II - 0.2389V1 - 0.3140V2 - 0.2389V3 - 0.0550V4 + 0.0615V5 + 0.1138V6$$

(2) Calculate Differences:
$$dx[n] = x[n] - x[n-1] \text{ for } n = 2,3,\cdots,N$$
$$dy[n] = y[n] - y[n-1] \text{ for } n = 2,3,\cdots,N$$
$$dz[n] = z[n] - z[n-1] \text{ for } n = 2,3,\cdots,N$$
$$d^2x[n] = x[n+1] - 2x[n] + x[n-1] \text{ for } n = 2,3,\cdots,N-1$$
$$d^2y[n] = y[n+1] - 2y[n] + y[n-1] \text{ for } n = 2,3,\cdots,N-1$$
$$d^2z[n] = z[n+1] - 2z[n] + z[n-1] \text{ for } n = 2,3,\cdots,N-1$$

Figure 18B (3) Calculate Difference Square Norms:
$da[n]^2 = dx[n]^2 + dy[n]^2 + dz[n]^2$ for $n = 2,3,\cdots,N$
$d^2a[n]^2 = d^2x[n]^2 + d^2y[n]^2 + d^2z[n]^2$ for $n = 2,3,\cdots,N-1$ (4) Calculate QRS threshold $\theta_{QRS}$
<loop> Within a loop of $i = 0 \to \text{floor}(N/5000) - 1$ (for every whole 5000 millisecond interval)
  Calculate Maximum 1st Difference Square Norm in $[5000i+1, 5000(i+1)]$
    $madz[i] = \max\{adz[g], g = 5000i, 5000i+1, \cdots, 5000(i+1)\}$
  Calculate Threshold: $\theta_{QRS} = \min_i \{madz[i]\}$ (5) Identify beats
<loop> While $31 < n < N - 100$, starting at $n = 31$, advancing one time step ($n = n + 1$) per loop unless otherwise instructed
  <if-then> If $da^2[n] > \theta_{QRS}$
    Search for Maximum 2nd Difference Square Norm in $[n-30+n+100]$
      $b_R[i] = \arg\max_m \{d^2a^2[m]: m = n-30, n-29, \cdots, n+100\}$, $i = 1,2,\cdots$ (the $i$-th beat)
    $n = n + 100$ (advance forward 100 milliseconds)

Characteristic Segment (Example: RT segment)
"3" to "4" shown in Figure 18A2

(1) Levkov Transform: (from 12-lead ECG to 3-lead Frank ECG)
$x = 0.0592I - 0.0877II - 0.1761V1 - 0.0771V2 + 0.1228V3 + 0.2432V4 + 0.2560V5 + 0.2078V6$ $y = 0.3827I + 0.4563II - 0.0179V1 - 0.0436V2 - 0.0490V3 + 0.0165V4 + 0.0541V5 + 0.0555V6$ $z = 0.0638I + 0.0258II - 0.2389V1 - 0.3140V2 - 0.2389V3 - 0.0550V4 + 0.0615V5 + 0.1138V6$ (2) Running Average:
$s_x[n] = \{\sum_{m=n-4}^{n+4} x[m]/9 : n = 5,6,\cdots,N-4\}$; $s_x[n] = \{0 : n = 1,2,3,4, N-3, N-2, N-1, N\}$
$s_y[n] = \{\sum_{m=n-4}^{n+4} y[m]/9 : n = 5,6,\cdots,N-4\}$; $s_y[n] = \{0 : n = 1,2,3,4, N-3, N-2, N-1, N\}$
$s_z[n] = \{\sum_{m=n-4}^{n+4} z[m]/9 : n = 5,6,\cdots,N-4\}$; $s_z[n] = \{0 : n = 1,2,3,4, N-3, N-2, N-1, N\}$

Figure 18B cont.

(3) Search for R-peaks using the R-peak beat marker $b_R[i], i = 1, 2, \cdots, N_{b0}$, $i = 1, 2, \cdots, N_{b0}$:

<loop> Within a loop of $i = 2 \to n_b - 1$ (for each identified beat except the first and last)

$n_{R0}[i] = \arg\max_n \{\max(s_x[n], s_y[n], s_z[n]) : n = b_R[i] - 20, b_R[i] - 19, \cdots, b_R[i] + 20\}$ (4) Calculate Average Beat Length: $mdb = \sum_{i=1}^{N_{b0}-1} (b_R[i+1] - b_R[i]) / (N_{b0} - 1)$ (5) Search for T-peak using
<loop> Within a loop of $i = 2 \to n_b - 1$ (for each identified beat except the first and last)

$n_{T0}[i] = \arg\max_n \left\{ \max(|s_x[n]|, |s_y[n]|, |s_z[n]|) : \begin{array}{l} n = n_{R0}[i] + 150, n_{R0}[i] + 151, \\ \cdots, n_{R0}[i] + 0.5 mdb \end{array} \right\}$ (6) Selecting RT Segments:

$\mu_{RT} = \mathrm{mean}_{i \in [1, N_{b0}-1]} \{n_{T0}[i] - n_{R0}[i]\}$, $\sigma_{RT} = \mathrm{stddev}_{i \in [1, N_{b0}-1]} \{n_{T0}[i] - n_{R0}[i]\}$ <loop> Within a loop of $i = 2 \to N_{b0} - 2$ (for each $n_{R0}$ and $n_{T0}$ pair)

<if-then> if $\mu_{RT} - \sigma_{RT} < n_{T0}[i] - n_{R0}[i] < \mu_{RT} + \sigma_{RT}$ Store $n_{R0}[i]$ into $n_R$ and $n_{T0}[i]$ into $n_T$ if "Yes"

Discard $n_{R0}[i]$ and $n_{T0}[i]$ if "No"

(7) Resample RT segments of all leads using $n_R[i]$ and $n_T[i]$, $i = 1, 2, \cdots, ct$ <loop> Within a loop of $i = 1 \to ct$, and for lead $x$, where the segment may be represented as $v[n] = x[n_R[i] + n - 1]$, $n = 1, 2, \cdots, n_T[i] - n_R[i] + 1$, $q = n_T[i] - n_R[i]$ a) Pre-process the segment:

$v_0[n] = \begin{cases} v[q - n + 1] - v[q], & n = 1, 2, \cdots q \\ v[n - q] - v[q], & n = q + 1, q + 2, \cdots, 2q \end{cases}$ b) Upsample by a factor of 1000:

$u_0[n] = \begin{cases} v_0[(n-1)/1000 + 1], & n = 1, 1001, 2001, \cdots, (2q-1)1000 + 1 \\ 0, & else \end{cases}$ c) Filter with any low pass filter with a gain of 1000 and a cut-off frequency of $\pi / 1000$ d) Downsample by a factor of $q$:

$w_0[n] = \overline{u}_0[(n-1)q + 1]$, for $n = 1, 2, \cdots, 2000$ e) Post-process the resampled segment:

$w[n] = w_0[1000 + n] + v[q]$, for $n = 1, 2, \cdots, 1000$

The resampled RT segments compose the length-1000 $r_{RT}$ for all leads

Figure 18B cont.

Refining the Characteristic Segment (Example: RT segment)
"4" to "5" shown in Figure 18A3

Take the magnitude of the 1000-point DFT of $\bar{r}_{RT}$:

$$\bar{r}_{RT}[n] = \frac{1}{N_b} \sum_{i=1}^{N_b} r_{RT,i}[n], \ n = 1,2,\cdots,1000.$$

Density and Distribution (Example: refined RT segment)
"5" to "6" shown in Figure 18A3

(1) Take the magnitude of the 1000-point DFT of $\bar{r}_{RT}$:

$$\bar{R}_{RT}[k] = \left|\sum_{n=1}^{1000} \bar{r}_{RT}[n] e^{-j2\pi k(n-1)/1000}\right|, \ k = 0,1,\cdots,999$$

(2) Grouping and indexing the density:
$\bar{h}_{RT}[k] = \bar{R}_{RT}[k], \ k = 1,2,\cdots,499$ (3) Computing the distribution at harmonic frequency units:
$H[k] = \sum_{l=1}^{k} \bar{h}_{RT}[l]$, for $k = 1,2,\cdots,499$.

Figure 18B cont.

Thresholds:
$\theta_1 = 1371.04$
$\theta_2 = 247.70$
$\theta_3 = 248.82$
$\theta_4 = 1198.36$
$\theta_5 = 932.71$
$\theta_6 = 252.33$
$\theta_7 = 3698.32$
$\theta_8 = 352.11$
$\theta_9 = 205.85$
$\theta_{10} = 125.29$

Figure 22A

Thresholds:
$\theta_1 = 1371.04$
$\theta_2 = 247.70$
$\theta_3 = 56.50$
$\theta_4 = 1126.48$
$\theta_5 = 493.85$
$\theta_6 = 1486.36$
$\theta_7 = 483.93$
$\theta_8 = 189.26$
$\theta_9 = 411.50$
$\theta_{10} = 1117.19$

Figure 22B

Thresholds:
$\theta_1 = 1371.04$
$\theta_2 = 247.70$
$\theta_3 = 284.72$
$\theta_4 = 717.44$
$\theta_5 = 80.00$
$\theta_6 = 199.33$
$\theta_7 = 386.21$
$\theta_8 = 123.98$
$\theta_9 = 2217.76$
$\theta_{10} = 728.24$

Figure 22C

METHODS, SYSTEMS AND DEVICES FOR DETECTING AND DIAGNOSING HEART DISEASES AND DISORDERS

CROSS-REFERENCE TO RELATED APPLICATIONS

This application is a continuation-in-part of and claims the benefit of U.S. patent application Ser. No. 11/774,688, filed 9 Jul. 2007, which is herein incorporated by reference in its entirety.

BACKGROUND OF THE INVENTION

1. Field of the Invention

The present invention relates to the field of electrocardiogram analysis.

2. Description of the Related Art

For over a hundred years since the invention of the electrocardiograph which produces a graphical recording (i.e. an electrocardiogram (ECG) which may be recorded on paper or stored as electronic data) of electrical activity of a heart over time. In the prior art there are two main perspectives in the study of the heart's electrical signals: (1) morphology, the meaning of the different deflections that appear to repeat from beat to beat, and (2) rhythm (or arrhythmology as used herein), the meaning of the different periodicities of these signals. Morphology is the study of electrocardiograms and is focused on the detection of muscular or conductional abnormalities within a beat such as myocardial ischemia, hypertrophies, bundle branch blocks, and the like. Arrhythmology is the study of electrical firing and conduction abnormalities such as ventricular premature beats, conduction blocks, and the like. An electrocardiogram as used herein may be a recording of a part of one (heart) beat, a complete beat, or more than one beat.

Myocardial ischemia is traditionally detected by morphological analysis, where an abnormally elevated or depressed deflection of the ST-segment within each beat indicates possible ischemia. Prior art methods of electrocardiogram analysis and interpretation, mainly visual inspection of the time-domain electrocardiogram, provide a poor expectation of about 30 to 60% accuracy in detection of ischemia.

Other methods of ischemia detection include pattern recognition methods such as frequency-domain analysis and wavelet-transform analysis. Pattern recognition involves taking a resource-limited observation (RLO) and a resource-rich observation (RRO) from the same subject. An RLO is an observation that is non-invasive, inexpensive, and time-efficient such as a conventional ECG. An RRO is an observation that is more invasive, more expensive, and less time-efficient as compared to an RLO such as exercise electrocardiography, dobutamine stress echocardiography, single positron emission computerized tomography (SPECT) Thallium-201 scanning, coronary angiography, and the like. RRO observations are more accurate in detecting ischemia as compared with conventional standard resting electrocardiogram analysis.

One pattern recognition method for detecting ischemia employs energy spectral density (ESD) analysis (sometimes referred to as power spectral density (PSD) analysis) of the harmonics of an electrocardiogram. See e.g. Fang & Hone, Principle and clinical application of Bio-Cybernetic Cardio-Diagnostic System (BKD) C2001; Fisher (1998) Biomedical Instrumentation Technology, 32(4):387; Noera & Oueida (1999) Giornale della Arteriosclerosi 34(2):81; and U.S. Pat. Nos. 5,649,544, 6,638,232, and 6,148,228; Fokapu & Girard (1991) Electrocardiography 12(2):645; Jones et al. (1992) J Electrocardiograph 25(Suppl):188; Rozentryt et al. (1999) Med Sci Monit 5(4):777; Haberl et al. (1989) European Heart J 10:316; Sierra et al. (1997) Proc 19$^{th}$ Int'l Conf IEEE/EMBS p. 76. Unfortunately, ESD methods and analysis are difficult to interpret and correlate to morphology consistently.

Therefore, a need still exists for methods, systems and devices for detecting and diagnosing heart diseases and disorders such as ischemia.

SUMMARY OF THE INVENTION

The present invention provides a method for determining a distribution function of a prime electrocardiogram which comprises obtaining a prime electrocardiogram; obtaining density functions for the harmonics in a range of harmonics of the prime electrocardiogram; and summing the density functions. In some embodiments, the prime electrocardiogram is a prime morphological electrocardiogram. In other embodiments, the prime electrocardiogram is a prime arrhythmological electrocardiogram. In some embodiments, the prime morphological electrocardiogram is obtained by obtaining a raw electrocardiogram as electronic data; selecting at least one characteristic segment or at least one characteristic window; and isolating the characteristic segment or the characteristic window by removing information extraneous to the characteristic segment or the characteristic window. In some embodiments, the characteristic segment is a QT segment, an RT segment, or a PR segment. In some embodiments, the characteristic window includes part or all of a T-wave or part or all of a PQRST interval. In some embodiments, the characteristic segment or the characteristic window is further refined by averaging the characteristic segment or the characteristic window. In some embodiments, the averaged characteristic window or the averaged characteristic segment may be repeated by N times, wherein N is any positive integer. In some embodiments, the isolated characteristic segment is a plurality of isolated characteristic segments in series. In some embodiments, the isolated characteristic window is a plurality of isolated characteristic windows in series.

In some embodiments, the present invention provides a method for diagnosing or detecting a heart disease or disorder, such as myocardial ischemia in a subject which comprises acquiring a prime electrocardiogram from the subject; obtaining a plurality of density functions for the harmonics in a range of harmonics of the prime electrocardiogram; summing the plurality of density functions to give at least one distribution function; and determining the presence or absence of the heart disease or disorder based on whether the distribution function is indicative of the heart disease or disorder. In some embodiments, the prime electrocardiogram is a prime morphological electrocardiogram. In other embodiments, the prime electrocardiogram is a prime arrhythmological electrocardiogram. In some embodiments, the prime morphological electrocardiogram is obtained by obtaining a raw electrocardiogram as electronic data; selecting at least one characteristic segment or at least one characteristic window; and isolating the characteristic segment or the characteristic window by removing information extraneous to the characteristic segment or the characteristic window. In some embodiments, the characteristic segment is a QT segment, an RT segment, or a PR segment. In some embodiments, the characteristic window includes part or all of a T-wave or part or all of a PQRST interval. In some embodiments, the characteristic segment or the characteristic window is further refined by averaging the characteristic segment or the characteristic window. In some embodiments, the averaged characteristic window or the averaged characteristic segment may be repeated by N times, wherein N is any positive integer. In some embodiments, the isolated characteristic segment is a plurality of isolated characteristic segments in series. In some embodiments, the isolated characteristic window is a plurality of isolated characteristic windows in series.

In some embodiments, a combination of distribution functions selected from the group consisting of $H_{aVL}[30] \leq \theta_1$, $H_{V2}[6] > \theta_2$, and $H_{II}[6] \leq \theta_3$; $H_{aVL}[30] \leq \theta_1$, $H_{V2}[6] > \theta_2$, $H_{II}[6] > \theta_3$, $H_{V1}[30] > \theta_4$, and $H_{aVL}[499] > \theta_5$; $H_{aVL}[30] \leq \theta_1$, $H_{V2}[6] > \theta_2$, $H_{II}[6] > \theta_3$, $H_{V1}[30] \leq \theta_4$, and $H_{III}[30] > \theta_6$; $H_{aVL}[30] \leq \theta_1$, $H_{V2}[6] > \theta_2$, $H_{II}[6] > \theta_3$, $H_{V1}[30] \leq \theta_4$, $H_{III}[30] > \theta_6$, and $H_{V5}[499] > \theta_7$; and $H_{aVL}[30] \leq \theta_1$, $H_{V2}[6] > \theta_2$, $H_{II}[6] > \theta_3$, $H_{V1}[30] \leq \theta_4$, and $H_{III}[30] > \theta_6$, $H_{V5}[499] \leq \theta_7$, $H_{V5}[6] > \theta_8$, $H_{aVR}[6] > \theta_9$, and $H_{III}[6] > \theta_{10}$ is indicative of the heart disease or disorder. In some embodiments, a combination of distribution functions selected from the group consisting of $H_{aVL}[30] > \theta_1$; $H_{aVL}[30] \leq \theta_1$, and $H_{V2}[6] \leq \theta_2$; $H_{aVL}[30] \leq \theta_1$, $H_{V2}[6] > \theta_2$, $H_{II}[6] > \theta_3$, $H_{V1}[30] > \theta_4$, and $H_{aVL}[499] \leq \theta_5$; $H_{aVL}[30] \leq \theta_1$, $H_{V2}[6] > \theta_2$, $H_{II}[6] > \theta_3$, $H_{V1}[30] \leq \theta_4$, $H_{III}[30] > \theta_6$, $H_{V5}[499] \leq \theta_7$, and $H_{V5}[6] \leq \theta_8$; $H_{aVL}[30] \leq \theta_1$, $H_{V2}[6] > \theta_2$, $H_{II}[6] > \theta_3$, $H_{V1}[30] \leq \theta_4$, $H_{III}[30] > \theta_6$, $H_{V5}[499] \leq \theta_7$, $H_{V5}[6] > \theta_8$, and $H_{aVR}[6] \leq \theta_9$; and $H_{aVL}[30] \leq \theta_1$, $H_{V2}[6] > \theta_2$, $H_{II}[6] > \theta_3$, $H_{V1}[30] \leq \theta_4$, $H_{III}[30] > \theta_6$, $H_{V5}[499] \leq \theta_7$, $H_{V5}[6] > \theta_8$, $H_{aVR}[6] > \theta_9$, and $H_{III}[6] \leq \theta_{10}$ is indicative of the presence of the heart disease or disorder. In some embodiments, the method further comprises determining a secondary factor such as the subject's age or whether the subject suffers from diabetes mellitus.

Thus, in some embodiments, a combination of age and distribution functions selected from the group consisting of $H_{aVL}[30] \leq \theta_1$, $H_{V2}[6] > \theta_2$, age$\leq \theta_3$, and $H_{aVR}[30] \leq \theta_4$; $H_{aVL}[30] \leq \theta_1$, $H_{V2}[6] > \theta_2$, age$> \theta_3$, $H_{V5}[6] > \theta_5$, $H_{V1}[499] > \theta_6$, and $H_{aVR}[499] > \theta_{10}$; and $H_{aVL}[30] \leq \theta_1$, $H_{V2}[6] > \theta_2$, age$> \theta_3$, $H_{V5}[6] > \theta_5$, $H_{V1}[499] \leq \theta_6$, $H_{V2}[499] > \theta_7$, $H_{aVL}[30] > \theta_7$, $H_{aVL}[30] > \theta_8$, and $H_{V4}[6] > \theta_9$ is indicative of the absence of the heart disease or disorder. In some embodiments, a combination of age and distribution functions selected from the group consisting of $H_{aVL}[30] > \theta_1$; $H_{aVL}[30] > \theta_1$ and $H_{V2}[6] \leq \theta_2$; $H_{aVL}[30] > \theta_1$, $H_{V2}[6] \leq \theta_2$, age$\leq \theta_3$, and $H_{aVR}[30] > \theta_4$; $H_{aVL}[30] \leq \theta_1$, $H_{V2}[6] > \theta_2$, age$> \theta_3$, and $H_{V5}[6] \leq \theta_5$; $H_{aVL}[30] \leq \theta_1$, $H_{V2}[6] > \theta_2$, age$> \theta_3$, $H_{V5}[6] > \theta_5$, $H_{V1}[499] > \theta_6$, and $H_{aVR}[499] \leq \theta_{10}$; $H_{aVL}[30] \leq \theta_1$, $H_{V2}[6] > \theta_2$, age$> \theta_3$, $H_{V5}[6] > \theta_5$, $H_{V1}[499] \leq \theta_6$, and $H_{V2}[499] \leq \theta_7$; $H_{aVL}[30] \leq \theta_1$, $H_{V2}[6] > \theta_2$, age$> \theta_3$, $H_{V5}[6] > \theta_5$, $H_{V1}[499] \leq \theta_6$, $H_{V2}[499] > \theta_7$, $H_{aVL}[30] > \theta_7$, and $H_{aVL}[30] \leq \theta_8$; and $H_{aVL}[30] \leq \theta_1$, $H_{V2}[6] > \theta_2$, age$> \theta_3$, $H_{V5}[6] > \theta_5$, $H_{V1}[499] \leq \theta_6$, $H_{V2}[499] > \theta_7$, $H_{aVL}[30] > \theta_7$, $H_{aVL}[30] > \theta_8$, and $H_{V4}[6] \leq \theta_9$ is indicative of the presence of the heart disease or disorder.

In some embodiments, a combination of distribution functions and the presence or absence of diabetes mellitus (DM) selected from the group consisting of $H_{aVL}[6] \leq \theta_1$, DM is positive, and $H_{V6}[499] \leq \theta_2$; and $H_{aVL}[6] \leq \theta_1$, DM is negative, $H_{aVF}[6] > \theta_3$, $H_I[6] > \theta_4 S H_I[6] > \theta_4$, $H_{II}[6] \leq \theta_5$, $H_{III}[6] \leq \theta_6$, $H_{V5}[30] \leq \theta_7$, and $H_{V3}[6] \leq \theta_8$ is indicative of the absence of the heart disease or disorder. In some embodiments, a combination of distribution functions and the presence or absence of diabetes mellitus (DM) selected from the group consisting of $H_{aVL}[6] > \theta_1$; $H_{aVL}[6] \leq \theta_1$, DM is positive, and $H_{V6}[499] > \theta_2$; $H_{aVL}[6] \leq \theta_1$, DM is negative, and $H_{aVF}[6] \leq \theta_3$; $H_{aVL}[6] \leq \theta_1$, DM is negative, $H_{aVF}[6] > \theta_3$, and $H_I[6] \leq \theta_4$; $H_{aVL}[6] \leq \theta_1$, DM is negative, $H_{aVF}[6] > \theta_3$, $H_I[6] > \theta_4$, and $H_{II}[6] > \theta_5$; $H_{aVL}[6] \leq \theta_1$, DM is negative, $H_{aVF}[6] > \theta_3$, $H_I[6] > \theta_4$, $H_{II}[6] \leq \theta_5$, and $H_{III}[6] > \theta_6$, $H_{aVL}[6] \leq \theta_1$, DM is negative, $H_{aVF}[6] > \theta_3$, $H_I[6] > \theta_4$, $H_{II}[6] \leq \theta_5$, $H_{III}[6] \leq \theta_6$, and $H_{V5}[30] > \theta_7$; and $H_{aVL}[6] \leq \theta_1$, DM is negative, $H_{aVF}[6] > \theta_3$, $H_I[6] > \theta_4 S H_I[6] > \theta_4$, $H_{II}[6] \leq \theta_5$, $H_{III}[6] \leq \theta_6$, $H_{V5}[30] \leq \theta_7$, and $H_{V3}[6] > \theta_8$ is indicative of the absence of the heart disease or disorder.

In some embodiments, a plurality of distribution functions greater than a set threshold value is indicative of the presence of the heart disease or disorder.

In some embodiments, the following combination of distribution functions $$c_{3,1} = \left[1 + \exp\left(-\sum_{i=1}^{18} c_{2,i} g_{2,1,i} - g_{2,1,0}\right)\right]^{-1} \leq 0.5, \text{ where}$$

$$c_{2,l} = \left[1 + \exp\left(-\sum_{m=1}^{33} c_{1,m} g_{1,l,m} - g_{1,l,0}\right)\right]^{-1}$$

for $l = 1, 2, \ldots, 18$, where $c_{1,m} = [1 + \exp(-Q_m - g_{0,m,0})]^{-1}$ for $m = 1, 2, \ldots, 33$, where $Q_m = H_I[6]g_{0,m,1} + H_{II}[6]g_{0,m,2} + H_{III}[6]g_{0,m,3} + H_{aVR}[6]g_{0,m,4} +$ $H_{aVL}[6]g_{0,m,5} + H_{aVF}[6]g_{0,m,6} + H_{V1}[6]g_{0,m,7} + H_{V2}[6]g_{0,m,8} +$ $H_{V3}[6]g_{0,m,9} + H_{V4}[6]g_{0,m,10} + H_{V5}[6]g_{0,m,11} + H_{V6}[6]g_{0,m,12} +$ $H_I[30]g_{0,m,13} + H_{II}[30]g_{0,m,14} + H_{III}[30]g_{0,m,15} + H_{aVR}[30]g_{0,m,16} +$ $H_{aVL}[30]g_{0,m,17} + H_{aVF}[30]g_{0,m,18} + H_{V1}[30]g_{0,m,19} + H_{V2}[30]g_{0,m,20} +$ $H_{V3}[30]g_{0,m,21} + H_{V4}[30]g_{0,m,22} + H_{V5}[30]g_{0,m,23} + H_{V6}[30]g_{0,m,24}$, for m=1, 2, . . . , 33 is indicative of the absence of the heart disease or disorder. In some embodiments, the following combination of distribution functions $$c_{3,1} = \left[1 + \exp\left(-\sum_{i=1}^{18} c_{2,1} g_{2,1,i} g_{2,1,0}\right)\right]^{-1} > 0.5, \text{ where}$$

$$c_{2,1} = \left[1 + \exp\left(-\sum_{m=1}^{33} c_{1,m} g_{1,i,m} - g_{1,i,0}\right)\right]^{-1} \text{ for}$$

$l = 1, 2, \ldots, 18$, where $c_{1,m} = [1 + \exp(-Q_m - g_{0,m,0})]^{-1}$ for $m = 1, 2, \ldots, 33$, where $Q_m = H_I[6]g_{0,m,1} + H_{II}[6]g_{0,m,2} + H_{III}[6]g_{0,m,3} + H_{aVR}[6]g_{0,m,4} +$ $H_{aVL}[6]g_{0,m,5} + H_{aVF}[6]g_{0,m,6} + H_{V1}[6]g_{0,m,7} + H_{V2}[6]g_{0,m,8} +$ $H_{V3}[6]g_{0,m,9} + H_{V4}[6]g_{0,m,10} + H_{V5}[6]g_{0,m,11} + H_{V6}[6]g_{0,m,12} +$ $H_I[30]g_{0,m,13} + H_{II}[30]g_{0,m,14} + H_{III}[30]g_{0,m,15} + H_{aVR}[30]g_{0,m,16} +$ $H_{aVL}[30]g_{0,m,17} + H_{aVF}[30]g_{0,m,18} + H_{V1}[30]g_{0,m,19} + H_{V2}[30]g_{0,m,20} +$ $H_{V3}[30]g_{0,m,21} + H_{V4}[30]g_{0,m,22} + H_{V5}[30]g_{0,m,23} + H_{V6}[30]g_{0,m,24}$, for m=1, 2, . . . , 33 is indicative of the presence of the heart disease or disorder. In some embodiments, the method further comprises determining a secondary factor such as the subject's age or whether the subject suffers from diabetes mellitus.

Thus, in some embodiments, a combination of age, the presence or absence of diabetes mellitus, and distribution functions selected from the group consisting of $$c_{3,1} = \left[1 + \exp\left(-\sum_{i=1}^{20} c_{2,1} g_{2,1,i} - g_{2,1,0}\right)\right]^{-1} \leq 0.5, \text{ where}$$

-continued $$c_{2,l} = \left[1 + \exp\left(-\sum_{m=1}^{50} c_{1,m} g_{1,l,m} - g_{1,l,0}\right)\right]^{-1} \text{ for } l = 1, 2, \ldots, 20,$$

where $$c_{1,m} = [1 + \exp(-Q_m - g_{0,m,0})]^{-1} \text{ for } m = 1, 2, \ldots, 50, \text{ where}$$

$$Q_m =$$

$$H_I[6]g_{0,m,1} + H_{II}[6]g_{0,m,2} + H_{III}[6]g_{0,m,3} + H_{aVR}[6]g_{0,m,4} + H_{aVL}[6]g_{0,m,5} +$$

$$H_{aVF}[6]g_{0,m,6} + H_{V1}[6]g_{0,m,7} + H_{V2}[6]g_{0,m,8} + H_{V3}[6]g_{0,m,9} +$$

$$H_{V4}[6]g_{0,m,10} + H_{V5}[6]g_{0,m,11} + H_{V6}[6]g_{0,m,12} + H_I[30]g_{0,m,13} +$$

$$H_{II}[30]g_{0,m,14} + H_{III}[30]g_{0,m,15} + H_{aVR}[30]g_{0,m,15} +$$

$$H_{aVL}[30]g_{0,m,17} + H_{aVF}[30]g_{0,m,18} + H_{V1}[30]g_{0,m,15} +$$

$$H_{V2}[30]g_{0,m,20} + H_{V3}[30]g_{0,m,21} + H_{V4}[30]g_{0,m,22} + H_{V5}[30]g_{0,m,23} +$$

$$H_{V6}[30]g_{0,m,24} + (age)g_{0,m,25} + (DM)g_{0,m,26} \text{ for } m = 1, 2, \ldots, 50$$

where age is the age in years, and DM=1, if there is presence of diabetes mellitus, and DM=0, if there is no presence of diabetes mellitus is indicative of the absence of the heart disease or disorder.

In some embodiments, a combination of age, the presence or absence of diabetes mellitus, and the following combination of distribution functions $$c_{3,1} = \left[1 + \exp\left(-\sum_{i=1}^{20} c_{2,i} g_{2,1,i} - g_{2,1,0}\right)\right]^{-1} > 0.5, \text{ where}$$

$$c_{2,i} = \left[1 + \exp\left(-\sum_{m=1}^{50} c_{1,m} g_{1,i,m} - g_{1,i,0}\right)\right]^{-1} \text{ for } l = 1, 2, \ldots, 20,$$

where $$c_{1,m} - [1 + \exp(-Q_m - g_{0,m,0})]^{-1} \text{ for } m = 1, 2, \ldots, 50, \text{ where}$$

$$Q_m =$$

$$H_I[6]g_{0,m,1} + H_{II}[6]g_{0,m,2} + H_{III}[6]g_{0,m,3} + H_{aVR}[6]g_{0,m,4} + H_{aVL}[6]g_{0,m,5} +$$

$$H_{aVF}[6]g_{0,m,6} + H_{V1}[6]g_{0,m,7} + H_{V2}[6]g_{0,m,8} + H_{V3}[6]g_{0,m,9} +$$

$$H_{V4}[6]g_{0,m,10} + H_{V5}[6]g_{0,m,11} + H_{V6}[6]g_{0,m,12} + H_I[30]g_{0,m,13} +$$

$$H_{II}[30]g_{0,m,14} + H_{III}[30]g_{0,m,15} + H_{aVR}[30]g_{0,m,16} + H_{aVL}[30]g_{0,m,17} +$$

$$H_{aVF}[30]g_{0,m,16} + H_{V1}[30]g_{0,m,18} + H_{V1}[30]g_{0,m,19} +$$

$$H_{V2}[30]g_{0,m,20} + H_{V3}[30]g_{0,m,21} + H_{V4}[30]g_{0,m,22} + H_{V5}[30]g_{0,m,23} +$$

$$H_{V6}[30]g_{0,m,24} + (age)g_{0,m,25} + (DM)g_{0,m,26} \text{ for } m = 1, 2, \ldots, 50,$$

where age is the age in years, and DM=1, if there is presence of diabetes mellitus, and DM=0, if there is no presence of diabetes mellitus is indicative of the presence of the heart disease or disorder.

In some embodiments, the following combination of distribution functions $$c_{2,1} = \left[1 + \exp\left(-\sum_{m=1}^{75} c_{1,m} g_{1,1,m} - g_{1,1,0}\right)\right]^{-1} \leq 0.5, \text{ where}$$

$$c_{2,1} = \left[1 + \exp\left(-\sum_{m=1}^{75} c_{1,m} g_{1,1,m} - g_{1,1,0}\right)\right]^{-1} \leq 0.5, \text{ where}$$

$$c_{1,m} = [1 + \exp(-Q_m - g_{0,m,0})]^{-1} \text{ for } m = 1, 2, \ldots, 75, \text{ where}$$

$$Q_m =$$

$$H_I[6]g_{0,m,1} + H_{II}[6]g_{0,m,2} + H_{V1}[6]g_{0,m,3} + H_{V2}[6]g_{0,m,4} + H_{V3}[6]g_{0,m,5} +$$

$$H_{V4}[6]g_{0,m,6} + H_{V5}[6]g_{0,m,7} + H_{V6}[6]g_{0,m,8} + H_I[30]g_{0,m,9} +$$

$$H_{II}[30]g_{0,m,10} + H_{V1}[30]g_{0,m,11} + H_{V2}[30]g_{0,m,12} +$$

$$H_{V3}[30]g_{0,m,13} + H_{V4}[30]g_{0,m,14} + H_{V5}[30]g_{0,m,15} +$$

$$H_{V6}[30]g_{0,m,16} \text{ for } m = 1, 2, \ldots, 75$$

is indicative of the absence of the heart disease or disorder. In some embodiments, the following combination of distribution functions $$c_{2,1} = \left[1 + \exp\left(-\sum_{m=1}^{75} c_{1,m} g_{1,1,m} - g_{1,1,0}\right)\right]^{-1} > 0.5, \text{ where}$$

$$c_{1,m} = [1 + \exp(-Q_m - g_{0,m,0})]^{-1} \text{ for } m = 1, 2, \ldots, 75, \text{ where}$$

$$c_{2,1} = \left[1 + \exp\left(-\sum_{m=1}^{75} c_{1,m} g_{1,1,m} - g_{1,1,0}\right)\right]^{-1} > 0.5, \text{ where}$$

$$c_{1,m} = [1 + \exp(-Q_m - g_{0,m,0})]^{-1} \text{ for } m = 1, 2, \ldots, 75, \text{ where}$$

$$Q_m - H_I[6]g_{0,m,1} + H_{II}[6]g_{0,m,2} + H_{V1}[6]g_{0,m,3} +$$

$$H_{V2}[6]g_{0,m,4} + H_{V3}[6]g_{0,m,5} + H_{V4}[6]g_{0,m,6} + H_{V5}[6]g_{0,m,7} +$$

$$H_{V6}[6]g_{0,m,8} + H_I[30]g_{0,m,9} + H_{II}[30]g_{0,m,10} + H_{V1}[30]g_{0,m,11} +$$

$$H_{V2}[30]g_{0,m,12} + H_{V3}[30]g_{0,m,13} + H_{V4}[30]g_{0,m,14} +$$

$$H_{V5}[30]g_{0,m,15} + H_{V6}[30]g_{0,m,16} \text{ for } m = 1, 2, \ldots, 75$$

is indicative of the absence of the heart disease or disorder.

Any one or more of the steps of the method of the present invention may be performed with a software program, a computer, an electrocardiograph, an electrical circuit, a data acquisition module, a prime electrocardiogram converter, or a combination thereof.

In some embodiments, the present invention provides a system or device for detecting or diagnosing a subject as suffering from a heart disease or disorder comprising an electrocardiograph for obtaining a raw electrocardiogram from the subject; a data acquisition module for converting the raw electrocardiogram into a raw digital electrocardiogram; a prime electrocardiogram converter for converting the raw digital electrocardiogram into a prime electrocardiogram; and a distribution function computer to calculate at least one distribution function of the prime electrocardiogram.

In some embodiments, the present invention provides a system or device for detecting or diagnosing a subject as suffering from a heart disease or disorder comprising means for obtaining a raw electrocardiogram from the subject; means for converting the raw electrocardiogram into a raw digital electrocardiogram; means for converting the raw digital electrocardiogram into a prime electrocardiogram; and means for calculating at least one distribution function of the prime electrocardiogram.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 5B shows the ESD of the ECG of FIG. 5A. The harmonics of the ECG of FIG. 5A are shown to be evenly-spaced, with all zero ESD in between.

FIG. 5D shows the ESD of the ECG of FIG. 5C. The harmonics of the ECG of FIG. 5C are shown to be evenly-spaced, with comparably low ESD in between.

FIG. 13E shows an ideal triangle wave at a sampling rate of 1000 samples per second, at a magnitude of 5 and period of 100 ms.

FIG. 18A1 schematically shows the steps for calculating the 12-lead ECG and identifying the beat marker.

FIG. 18A2 schematically shows obtaining the characteristic segment.

FIG. 18A3 schematically shows refining the characteristic segment and obtaining the density and distribution of a prime morphological ECG.

FIG. 18B outlines the steps in FIGS. 18A and 18A1 to 18A3.

FIG. 22A shows sample threshold values of the statistical decision tree of FIG. 19.

FIG. 22B shows sample threshold values of the statistical decision tree of FIG. 20.

FIG. 22C shows sample threshold values of the statistical decision tree of FIG. 21.

DETAILED DESCRIPTION OF THE INVENTION

The present invention provides methods and devices for detecting and diagnosing heart diseases and disorders in a subject based on electrocardiograms (ECGs) obtained from the subject. Specifically, the present invention relates to methods and devices for analyzing the morphology of an ECG to diagnose heart diseases and disorders, such as myocardial ischemia, hypertrophies, bundle branch blocks, ventricular pre-excitations, and the like. In some embodiments, the present invention provides methods and devices for analyzing the morphology of the systolic cycle (e.g. RT segment) of the beats of an ECG to detect or diagnose myocardial ischemia (ischemia) in a subject.

Prior art methods of ESD analysis attempt to detect and diagnose heart disease, such as ischemia, by examining multiple periods (90 seconds) of an ECG, x, that is directly transformed into the frequency domain and expressed in terms of its energy spectral density, $|X(f)|^2$ and then correlates the energy spectral density to heart disease. See e.g. ESD methods U.S. Pat. No. 6,638,232, U.S. Pat. No. 6,148,228, and U.S. Pat. No. 5,649,544, which are herein incorporated by reference.

Unfortunately, prior art ESD methods and analysis are difficult to interpret and correlate to morphology consistently. Specifically, prior art ESD analysis does not account for the disintegration of the harmonics due to one or more aperiodicities of an ECG. For example, the method of Fang et al. (U.S. Pat. Nos. 6,638,232 and 6,148,228) attempts to detect ischemia by calculating the area under the curve (AUC) of the ESD. However, Fang et al. fails to adequately correlate the area under the curve to heart disease because harmonic disintegration is not addressed. Thus, the method of Fang et al can not adequately correlate ESD of an ECG to heart disease.

A harmonic is the spectral energy that is an integer multiple of a fundamental frequency of an ECG signal. As used herein, "harmonic disintegration" refers to a distortion of the height and shape of a harmonic due to the dispersion of the harmonic energy from the harmonic frequency to neighboring frequencies by aperiodicities. As used herein, "aperiodicities" include arrhythmological aperiodicities, such as leakage due to aperiodic windowing and periodic rate variability, and morphological aperiodicities, such as beat morphological variations, sub-fundamental frequency oscillations and white noise.

Figure 1A:
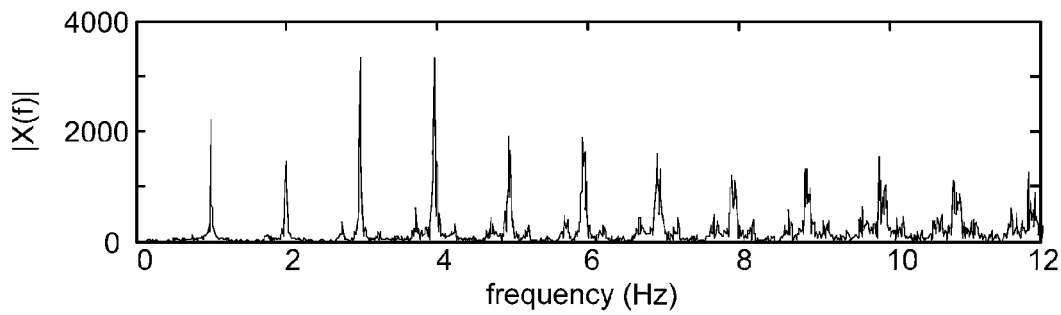
FIG. 1A shows the energy spectral density (ESD) of an ECG with low frequency domain dispersion for the best case scenario of a prior art method.
Figure 1B:
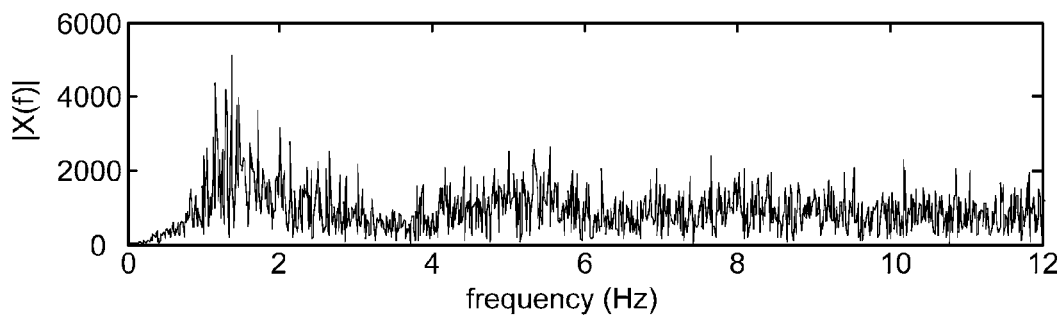
FIG. 1B shows the ESD of an ECG with severe frequency domain dispersion for the worst case scenario of a prior art method.

For example, the ESDs of electrocardiograms from over 400 patients were determined according to prior art ESD methods. The best case ESD was taken from an electrocardiogram having the smallest amount of aperiodicities exhibited distinct harmonics until about the $8^{th}$ or $9^{th}$ harmonic. The best case ESD is shown in FIG. 1A wherein harmonic disintegration is observable (as peaks that are less distinct than the peaks at the first few harmonics) at about the $8^{th}$ or $9^{th}$ harmonic. The worst case ESD was taken from an electrocardiogram exhibiting the largest amount of aperiodicities severe arrhythmia and heart rate variability (HRV). The worst case ESD is shown in FIG. 1B wherein distinct harmonics are not present.

As disclosed herein, the present invention addresses the problem of harmonic disintegration in ESD of an ECG, thereby enabling the analysis of morphological data that can be accurately correlated to the presence or absence of heart disease.

Unless otherwise indicated, all ECGs were sampled at 1000 Hz with a 12-bit resolution. As used herein, a "raw" ECG refers an electrocardiogram obtained from a subject with an electrocardiograph which as not been modified or manipulated, e.g. a conventional ECG obtained using electrocardiographs known in the art.

Aperiodicities

There are two types of aperiodicities. The first is "arrhythmological aperiodicity" which is a condition where the time to complete a cardiac cycle varies from beat to beat. The second is "morphological aperiodicity" which is a condition where the shape of amplitude deflections at an instantaneous point along the time trajectory varies from beat to beat.

1. Arrhythmological Aperiodicities

Arrhythmological aperiodicities include leakage due to aperiodic windowing and periodic rate variability. Leakage due to aperiodic windowing is leakage of the spectral energy from a harmonic due to incorporation of an incomplete period (a portion of a beat of an ECG). Periodic rate variability includes heart rate variability and arrhythmias.

a. Leakage Due to Aperiodic Windowing

Harmonic disintegration due to leakage due to aperiodic windowing may be exemplified by the following:

First, an ideal impulse train is obtained. As used herein, an "ideal impulse train" refers to an impulse train having impulses uniformly spaced in time and identical in magnitude. An impulse train (Dirac comb) is a series of impulses alternating with periods in the time domain, wherein the impulses have magnitudes of one and the periods have magnitudes of zero. Specifically, the ideal impulse train was obtained by first calculating the average of the beat periods of an ECG, identifying the number of beats and then generating a train of impulses having a number of impulses that is the same as the number of beats, giving each impulse a magnitude of one which alternate with periods having magnitudes of zero, and separating the impulses by the average of the beat periods. Then, aperiodic windowing of the ideal impulse train is created by removing a portion of the last period of the ideal impulse train.

Figure 2A:
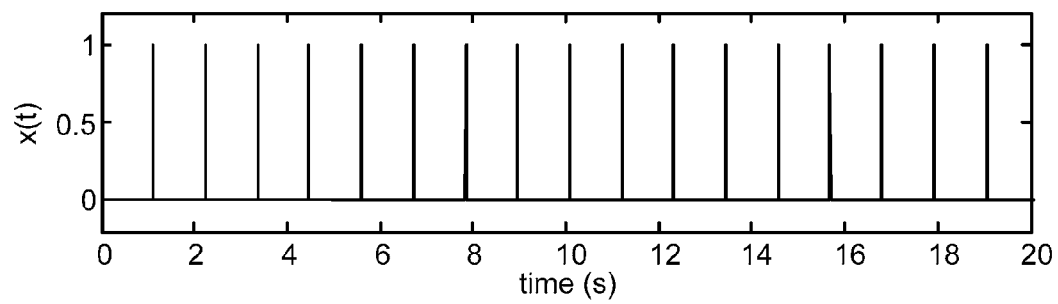
FIG. 2A shows 20 seconds of an ideal impulse train at a sampling rate of 1000 samples per second and spaced 1120 milliseconds (ms) apart.
Figure 2B:
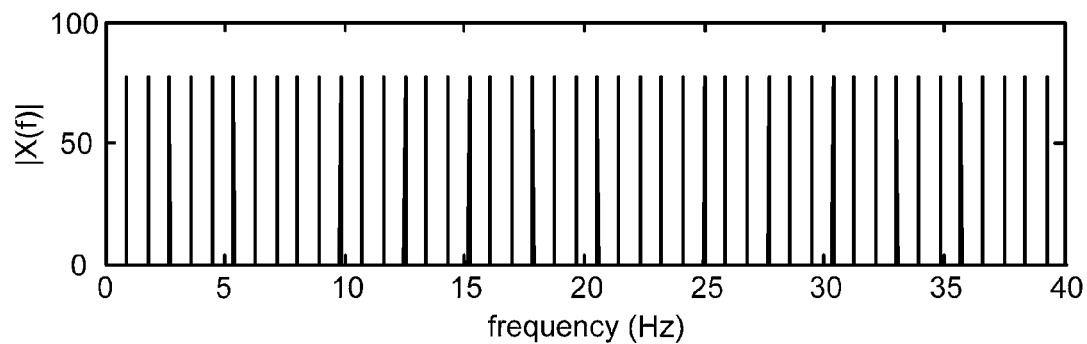
FIG. 2B shows the ESD of the impulse train of FIG. 2A from 0 to 40 Hertz (Hz).
Figure 3A:
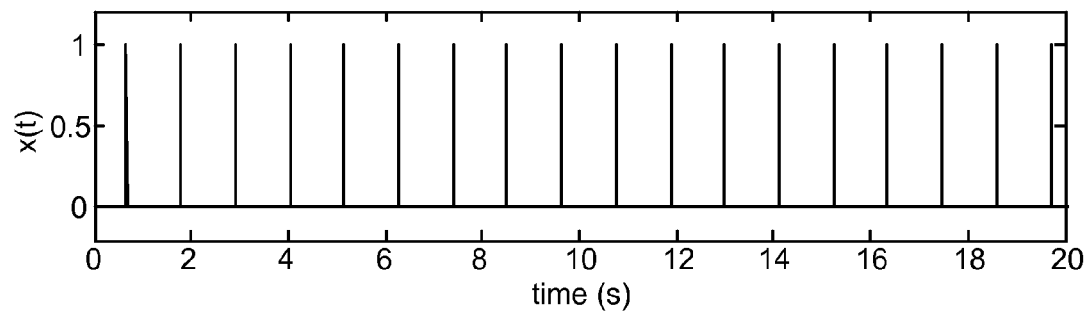
FIG. 3A shows an impulse train with windowing leakage which was created by taking the ideal impulse shown in FIG. 2A and removing the first 400 ms.

To observe the effect of leakage due to aperiodic windowing, the discrete Fourier transform (DFT) of the ideal impulse train and the aperiodic windowed ideal impulse train were taken to obtain the ESDs. FIG. 2A shows the ideal impulse train and its ESD is shown in FIG. 2B. FIG. 3A shows the aperiodic windowed ideal impulse train and its ESD is shown in FIG. 3B.

Figure 3B:
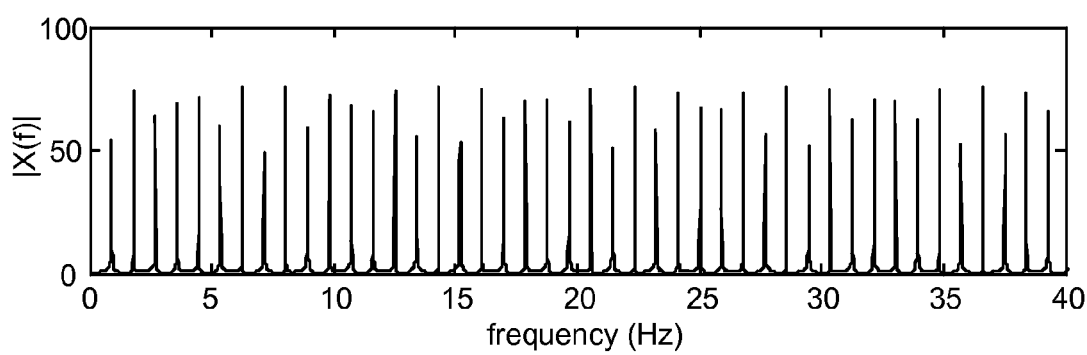
FIG. 3B shows the ESD of the impulse train of FIG. 3A from 0 to 40 Hz.

A comparison of FIG. 2B and FIG. 3B shows that leakage due to aperiodic windowing results in harmonics of varying magnitudes thereby illustrating harmonic disintegration.

b. Periodic Rate Variability

Harmonic disintegration due to periodic rate variability may be exemplified by the following:

First, an impulse train having impulses at locations in the time domain corresponding to the R peaks of an ECG with heart rate variability (HRV) was obtained.

Figure 4A:
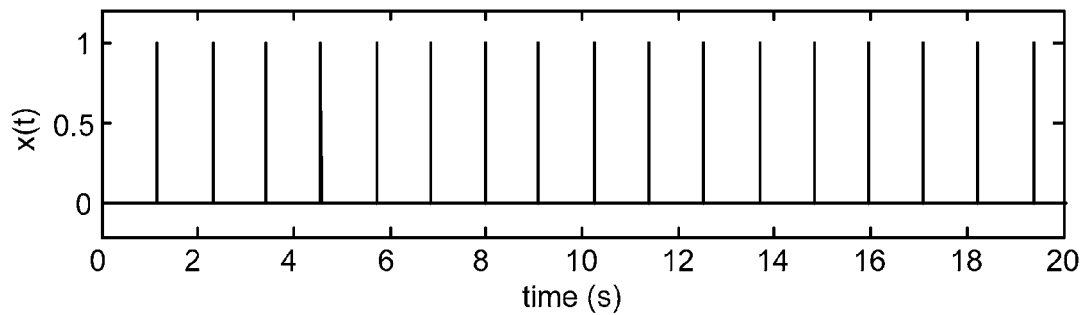
FIG. 4A shows an impulse train with rate variability which was created by taking an ECG sampled at 1000 samples per second and making all of its deflections zero except for its R peak locations, which were set to a deflection of one. The mean period between beats of this ECG is 1.12 seconds, and the standard deviation of its periods is 0.021 s.

To observe the effect of periodic rate variability, the discrete Fourier transform (DFT) of the impulse train was taken to obtain the ESD. FIG. 4A shows the impulse train and its ESD is shown in FIG. 4B.

Figure 4B:
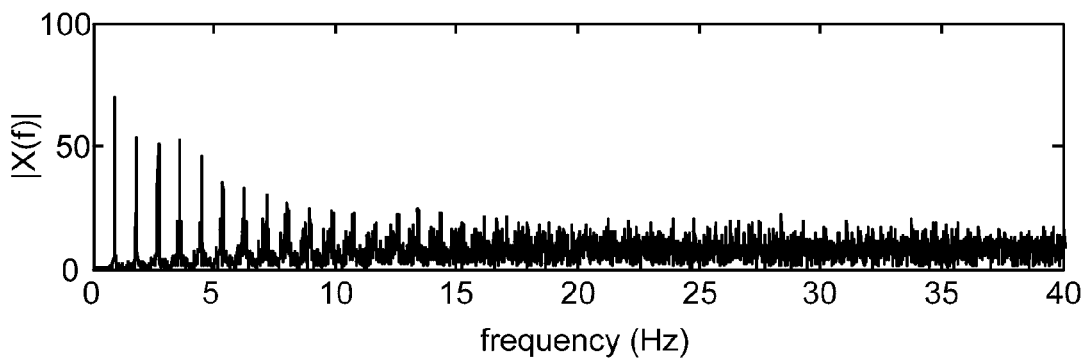
FIG. 4B shows the ESD of the impulse train of FIG. 4A from 0 to 40 Hz.

A comparison of FIG. 2B and FIG. 4B shows that periodic rate variability results in harmonics which are indistinguishable at increasing frequencies thereby illustrating harmonic disintegration.

2. Morphological Aperiodicities

Morphological aperiodicities include beat morphology variations, sub-fundamental frequency oscillations, and white noise. Beat morphological variations refer to the differences in shape between different beats in the same lead of the same ECG. Sub-fundamental frequency oscillations are oscillations that occur at frequencies that are lower than the fundamental frequency (frequency of an ECG is the average heart rate). White noise, or more commonly known as additive white Gaussian noise (AWGN), is a random signal with a flat power spectral density.

a. Beat Morphological Variations

Figure 5A:
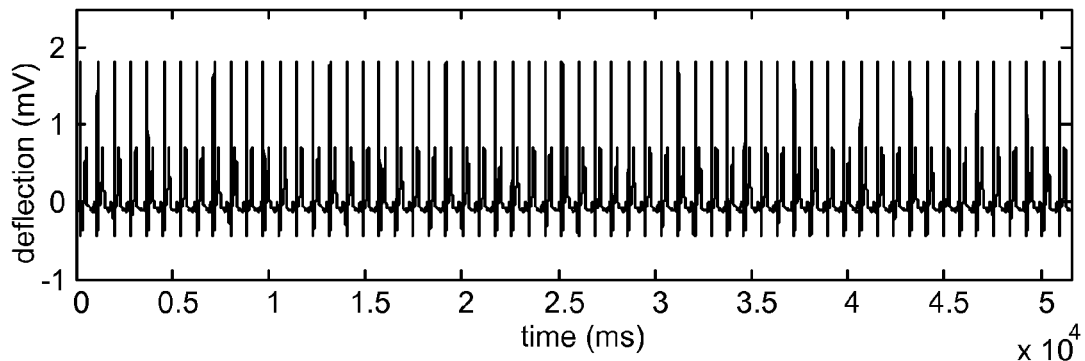
FIG. 5A shows an ideal ECG which was created by taking one beat of an ECG sampled at 1000 samples per second and repeating it 60 times.
Figure 5B:
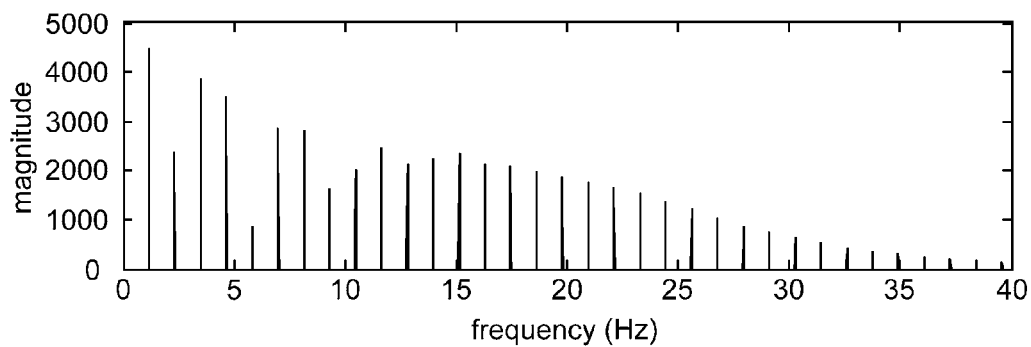
Figure 5C:
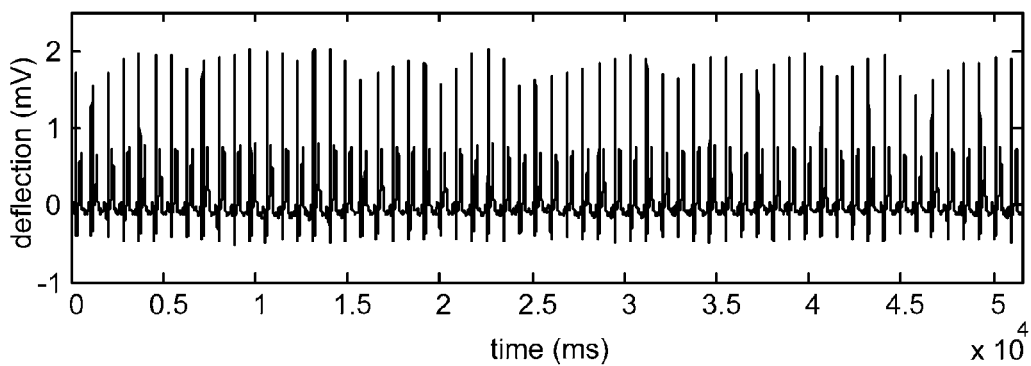
FIG. 5C shows an aligned ECG which was created by taking a characteristic window comprising most of the PQRST interval of the ECG used in FIG. 5A with the beat marker representing the R-peak.

Harmonic disintegration due to beat morphological variations may be illustrated by the following:

First, the periods and the deflections of the beats of an ECG were made to be identical in length and shape to obtain an ideal ECG and the beat periods of an ECG were made to be identical in length while maintaining the different shapes of the beats to obtain an ECG having beat morphological variations. Then, the DFTs of the ideal ECG and the ECG having beat morphological variations were taken. FIG. 5A shows the ideal ECG and its ESD is shown in FIG. 5B. FIG. 5C shows the ECG having beat morphological variations and its ESD is shown in FIG. 5D.

Figure 5D:
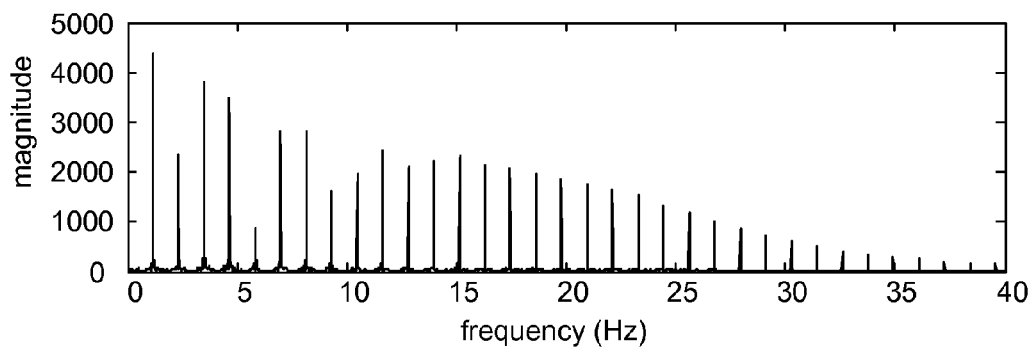

A comparison of FIG. 5B and FIG. 5D shows that beat morphological variations results in some harmonic disintegration which is provided at the baseline of FIG. 5D.

b. Sub-Fundamental Frequency Oscillations

Sub-fundamental frequency oscillations are due to breathing, movement, surface muscle contraction, and interference from electrical activity of other organs. In some embodiments of the present invention, sub-fundamental frequency oscillations may be filtered out using low corner frequency highpass filters and methods known in the art.

c. White Noise

White noise is caused by friction and other thermal noise and environmental noise. In some embodiments of the present invention, the effects of white noise may be reduced by signal averaging or optimizing hardware design using methods known in the art.

Thus, the present invention addresses the problem of harmonic disintegration in ESDs of ECGs due to aperiodicities. Specifically, the present invention provides a method of determining the distribution functions of a prime ECG which may be used to detect and diagnose heart diseases and disorders such as myocardial ischemia.

I. Creation of a Prime ECG

As used herein, a "prime ECG" refers to an ECG which is modified such that certain information of each beat in the ECG is made to be constant. A prime ECG includes a prime morphological ECG and a prime arrhythmological ECG. As used herein, a "prime morphological ECG" refers to an ECG which is modified such that the arrhythmological information of each beat is made to be constant. As used herein, a "prime arrhythmological ECG" refers to an ECG which is modified such that the morphological information of each beat is made to be constant.

Before a prime ECG is created, an ECG must be obtained from a subject. The ECG may be obtained with a device, such as an electrocardiograph, that measures electrical potentials caused by heart activity. There are a variety of methods and devices known in the art for obtaining an ECG, such devices include the CAM-14® available from General Electric Healthcare (Milwaukee, Wis.), the UNIVERSAL ECG™ available from QRS Diagnostic (Plymouth, Minn.), the CARDIO-CARD® available from Nasiff Associates (Brewerton, N.Y.), and the like. Preferably, the ECG is accessible in computer readable form, e.g. recorded and/or stored as electronic data, which allows one to readily manipulate the data mathematically.

Conventional methods and devices employing the 12 lead system may be used in accordance with the present invention. In these embodiments, the computation of the lead data for the 12 lead system (Leads I, II, III, aVR, aVL, aVF, V1, V2, V3, V4, V5, V6) acquired from the 10 electrodes (RA, LA, RL, LL, C1, C2, C3, C4, C5, C6) is done by the device or algorithms known in the art. See Malmivuo & Plonsey (1995) BIOELECTROMAGNETISM Oxford: New York, which is herein incorporated by reference.

In other embodiments, alternative lead systems may be used in accordance with the present invention. Alternative lead systems include the 15 lead system, the 16 lead system, the 30 lead system, the 32 lead system, the 9 lead system, the 3 lead systems (including EASI and Frank leads), and the like. See Lux et al. (1979) Circulation 59(2): 356, Brady et al. (2000) Amer. J. of Emergency Medicine 18(3): 239, Sgarbossa et al. (2001) Amer. Heart J. 141(4): 507, Dower et al. (1988) J. of Electrocardiology Suppl: S182, and Edenbrandt et al. (1988) J. of Electrocardiology 21(4): 361, which are herein incorporated by reference. For example, in accordance with the present invention, an ECG may be obtained with one of these alternative lead systems rather than with the conventional 12 lead system.

A. Prime Morphological ECG

Once the ECG is obtained, a prime morphological ECG is made by isolating the morphological information of beats from the ECG by making the arrhythmological information constant, and may further include refining the morphological information.

1. Isolating Morphological Information

Once the ECG is obtained, then a beat marker for the beats is selected. As used herein a "beat marker" refers to a characteristic point that corresponds to a desired electrical state in a cardiac cycle, such as the P-peak, the Q-peak, the R-peak, the S-peak, the J-point, the T-peak, and the like. A beat marker may readily be identified using methods known in the art. See Haque et al. (2002) 2nd Int'l Conf. Elec. & Comp Engr. and Afonso et al. (1999) IEEE Trans. on Biomed Eng. 46(2):192, which are herein incorporated by reference.

As exemplified herein, the beat markers were identified using a vectorcardiogram (VCG). First, VCG with an orthogonal lead system using the Levkov transform was obtained using methods known in the art. See Augustyniak (2001) Proc. of 10$^{th}$ Int'l Conf. on System-Modelling-Control, p. 51 and Levkov (1987) Med & Biol Engr & Computing, March, p. 155, which are herein incorporated by reference. Then the first and second differences of the VCG was taken and a representative maximum distance from the point of origin of the first derivative over the entire VCG was determined. The durations in the first difference of the entire VCG which exceeded more than half of the maximum distance were detected and a point in each of the durations which had the lowest second difference was found.

For example, a beat marker representing the R-peak for an ECG sampled at 1000 samples per second was identified by:
1. Calculating the length-N VCG (x, y, z) from the length-N 12-lead ECG (I, II, III, aVR, aVL, aVF, V1, V2, V3, V4, V5, V6) using the Levkov transform:

$x=0.0592I-0.0877II-0.1761V1-0.0771V2+0.1228V3+0.2432V4+0.2560V5+0.2078V6$ $y=0.3827I+0.4563II-0.0179V1-0.0436V2-0.0490V3+0.0165V4+0.0541V5+0.0555V6$ $z=0.0638I+0.0258II-0.2389V1-0.3140V2-0.2389V3-0.0550V4+0.0615V5+0.1138V6$

2. Calculating the first-order differences of the VCG (dx, dy, dz), and the second-order differences of the VCG ($d^2x, d^2y, d^2z$):

$dx[n]=x[n]-x[n-1]$ for $n=2,3,\ldots,N$ $dy[n]=y[n]-y[n-1]$ for $n=2,3,\ldots,N$ $dz[n]=z[n]-z[n-1]$ for $n=2,3,\ldots,N$ $d^2x[n]=x[n+1]-2x[n]+x[n-1]$ for $n=2,3,\ldots,N-1$ $d^2y[n]=y[n+1]-2y[n]+y[n-1]$ for $n=2,3,\ldots,N-1$ $d^2z[n]=z[n+1]-2z[n]+z[n-1]$ for $n=2,3,\ldots,N-1$ 3. Calculating the first-order difference square norms of the VCG ($da^2$), and the second-order difference square norms of the VCG ($d^2a^2$):

$da^2[n]=dx^2[n]+dy^2[n]+dz^2[n]$ for $n=2,3,\ldots,N$ $d^2a^2[n]=d^2x^2[n]+d^2y^2[n]+d^2z^2[n]$ for $n=2,3,\ldots,N-1$ 4. Finding the maxima of $\{da^2[n]: n=5000i+1, 5000i+2, \ldots, 5000(i+1)\}$, where $0 \le i < N/5000-1$, letting a threshold ($\theta_{QRS}$) be one-half of the minimum of these maxima
5. Identifying beats (b) by scanning $da^2[n]$ from $n=31$ to $n=N-100$, such that each time $\theta_{QRS}$ is exceeded by $da^2[n]$ an R-peak beat marker is located at $b_R[i]=\arg\max_m\{d^2a^2[m]: m=n-30, n-29, \ldots, n+100\}$, $i=1, 2, \ldots$, and scanning is resumed at $n+100$.

a. Characteristic Segment

After the beat marker is selected, a segment may be chosen. A segment includes the conventional segments commonly used in ECG analysis, such as the PR segment, the PR interval, the QRS complex, the ST segment, and the QT interval, and other segments, such as the RT segment which is the segment from the R-peak to the T-peak, the RT stop segment which is the segment from the R-peak to the end of the T, the JT segment which is the segment from the J-point to the T-peak, the PQ segment which is the segment from the P-peak to the Q-peak, the complete segment which is the segment that begins at the PR interval to the end of the QT interval, the complete point segment, which is the segment from one point in a cardiac cycle to the corresponding point in the next cardiac cycle (e.g. the RR interval), and the like.

The choice of the segment depends on the type of heart disease or disorder desired to be detected. For example, if one is interested in detecting ischemia, one would select the QT or the RT segment as data in these segments is known to be important in detection of ischemia and ventricular hypertrophies. See Camm, et al., eds. (2006) THE ESC TEXTBOOK OF CARDIOVASCULAR MEDICINE, Blackwell, which is herein incorporated by reference. Similarly, if one is interested in detecting atrial diseases or disorders, one would select the PR segment as data in this segment is known to be important in detection of such diseases and disorders including atrioventricular blocks, pericarditis, and atrial infarction. See Camm, et al., eds. (2006) THE ESC TEXTBOOK OF CARDIOVASCULAR MEDICINE, Blackwell, which is herein incorporated by reference.

As exemplified herein, the segment selected for detecting ischemia is the RT segment. Use of the RT segment is suitable for ischemia detection as the RT segment (1) includes the entire ST segment, (2) provides a frame of reference for the amplitude deflection of the ST segment as compared to the maximum deflections of its circumscribing R-wave and T-wave, and (3) is the portion of the systolic cycle in which repolarization takes place in the subepicardium, the ventricular territory most prone to ischemia or necrosis. See Camm, et al., eds. (2006) THE ESC TEXTBOOK OF CARDIOVASCULAR MEDICINE, Blackwell, which is herein incorporated by reference. Those skilled in the art may readily select a segment suitable for detecting and diagnosing a desired heart disease or condition in accordance with the present invention.

Once chosen, the segments are resampled to a given fixed length so that each resampled segment is identical in length to give a characteristic segment. Methods and devices known in the art may be used to resample the segment in accordance with the present invention. In some embodiments, resampling is conducted according to the classic Oppenheim & Schafer upsample-filter-downsample algorithm. See Oppenheim et al. (1989) DISCRETE-TIME SIGNAL PROCESSING, Prentice, which is herein incorporated by reference.

As exemplified herein, the characteristic segments were identified using a running average of a vectorcardiogram (VCG) and a beat marker. First, a VCG with an orthogonal lead system using the Levkov transform was obtained using methods known in the art. See Augustyniak (2001) Proc. of 10$^{th}$ Int'l Conf. on System-Modelling-Control, p. 51 and Levkov (1987) Med & Biol Engr & Computing, March p. 155, which are herein incorporated by reference. Then a running average of the VCG was taken. Characteristic points at the ends of the segment of the running average of the VCG were detected relative to the beat marker as some maxima of the running average of the VCG. Then only the beats for which the segment fall within one standard deviation of the mean of the lengths of the segments of the beats were selected. Each beat's segment was resampled to a fixed length. Since the characteristic segment is the result of resampling ECG segment of an arbitrary length (q) into a common length (p), it is not on a conventional time index such as an index of milliseconds. Consequently, the DFT of the characteristic segment is not on a conventional frequency index such as an index of Hertz. As used herein, a "time unit" refers to time-domain index of the characteristic segment. And as used herein, a "frequency unit" refers to frequency-domain index of the characteristic segment. The time unit and the frequency unit retain the same inverse relationship as the relationship between the second and the Hertz.

For example, a characteristic segment representing the RT segment for an ECG sampled at 1000 samples per second, with a beat marker representing the R-peak, was identified by:
1. Calculating the length-N VCG (x, y, z) from the length-N 12-lead ECG (I, II, III, aVR, aVL, aVF, V1, V2, V3, V4, V5, V6) using the Levkov transform:

$$x=0.0592I-0.0877II-0.1761V1-0.0771V2+0.1228V3+0.2432V4+0.2560V5+0.2078V6$$

$$y=0.3827I+0.4563II-0.0179V1-0.0436V2-0.0490V3+0.0165V4+0.0541V5+0.0555V6$$

$$z=0.0638I+0.0258II-0.2389V1-0.3140V2-0.2389V3-0.0550V4+0.0615V5+0.1138V6$$

2. Calculating a smoothened VCG($s_x, s_y, s_z$) by taking running averages:

$$s_x[n] = \begin{cases} \sum_{m=n-4}^{n+4} x[m]/9, & n=5, 6, \ldots, N-5, N-4 \\ 0, & n=1, 2, 3, 4, N-3, N-2, N-1, N \end{cases}$$

$$s_y[n] = \begin{cases} \sum_{m=n-4}^{n+4} y[m]/9, & n=5, 6, \ldots, N-5, N-4 \\ 0, & n=1, 2, 3, 4, N-3, N-2, N-1, N \end{cases}$$

$$s_z[n] = \begin{cases} \sum_{m=n-4}^{n+4} z[m]/9, & n=5, 6, \ldots, N-5, N-4 \\ 0, & n=1, 2, 3, 4, N-3, N-2, N-1, N \end{cases}$$

3. Identifying the segment R-peak locations ($n_{R0}$) using a beat marker representing the R-peak ($b_R[i]$, $i=1, 2, \ldots, N_{b0}$), for beats $i=1, 2, \ldots, N_{b0}$:

$$n_{R0}[i]=\arg\max_n\{\max(s_x[n], s_y[n], s_z[n]): n=b_R[i]-20, b_R[i]-19, \ldots, b_R[i]+20\}$$

4. Calculating the average beat period (mdb) by using a beat marker representing the R-peak ($b_R[i]$, $i=1, 2, \ldots, N_{b0}$): mdb=$\Sigma_{i=1}^{N_{b0}-1}(b_R[i+1]-b_R[i])/(N_{b0}-1)$
5. Identifying the segment T-peak locations ($n_{T0}$) using a beat marker representing the R-peak ($b_R[i]$, $i=1, 2, \ldots, N_{b0}$), the segment R-peak locations $n_{R0}$, and the average beat period mdb, for beats $i=1, 2, \ldots, N_{b0}-1$:

$$n_{T0}[i]=\arg\max_n\{\max(|s_x[n]|, |s_y[n]|, |s_z[n]|):$$

$$n=n_{R0}[i]+150, n_{R0}[i]+151, \ldots, n_{R0}[i]+0.5mdb\}$$

6. Selecting segment representing the RT segment ($\{n_R, n_T\}$) by calculating the segment periods ($dn_{RT0}$) for each of the $N_{b0}-1$ beats, $dn_{RT0}[i]=n_{T0}[i]-n_{R0}[i]$, calculating the mean ($\mu_{RT}$) and standard deviation ($\sigma_{RT}$) of $dn_{RT0}$, and selecting the segment in beats such that: $\{n_R, n_T\}=\{n_{R0}[i], n_{T0}[i]: \mu_{RT}-\sigma_{RT}<n_{T0}[i]-n_{R0}[i]<\mu_{RT}+\sigma_{RT}\}$, for any $i=1, 2, \ldots, N_{b0}-1$
7. Resampling the $N_b$ selected segment representing the RT segment (in locations $\{n_R[i], n_T[i]\}$, $i=1, 2, \ldots, N_b$, for all leads) from its corresponding segment lengths ($dn_{RT}[i]=n_T[i]-n_R[i]$, $i=1, 2, \ldots, N_b$) to a fixed length of 1000 by using the Oppenheim and Schafer algorithm as follows:

Given a length-q original sequence ($v[n]$), $n=1, 2, \ldots, q$, representing a segment of an ECG lead that is to be resampled to length-p resampled sequence ($w[n]$), $n=1, 2, \ldots, p$:

(a) Pre-process v such that the first and last value of the signal to be resampled are zero by creating a length-2q pre-processed original sequence ($v_0$) where:

$$v_0[n] = \begin{cases} v[q-n+1]-v[q], & n=1, 2, \ldots q \\ v[n-q]-v[q], & n=q+1, q+2, \ldots, 2q \end{cases}$$

(b) upsample $v_0[n]$ by factor of p by zero-filling to create a length-2pq upsampled sequence ($u_0$) where:

$$u_0[n] = \begin{cases} v_0[(n-1)/p+1], & n=1, p+1, 2p+1, \ldots, (2q-1)p+1 \\ 0, & \text{else} \end{cases}$$

(c) filter with any low pass filter with a gain of p and a cut-off frequency of $\pi/p$ to get a length-2pq filtered upsampled sequence ($\bar{u}_0$):
(d) downsample $\bar{u}_0$ by factor of q by sampling to create a length-2p pre-processed resampled sequence ($w_0$) where:

$$w_0[n]=\bar{u}_0[(n-1)q+1], \text{ for } n=1, 2, \ldots, 2p$$

(e) post-process $w_0$ to recover the resampled sequence by creating a length-p resampled sequence (w) where:

$$w[n]=w_0[p+n]+v[q], \text{ for } n=1, 2, \ldots, p$$

b. Characteristic Window

After the beat marker is selected, a window may be chosen. A window comprises the conventional intervals commonly used in ECG analysis, the PR segment, the PR interval, the QRS complex, the ST segment, and the QT interval, and other intervals, such as the R wave which comprises all of the R wave, the T wave which comprises all of the T wave, the PQRST interval, which is an interval that overlaps with the interval from the start of the P wave to the end of the T wave, and the like.

The choice of the window depends on the type of heart disease or disorder desired to be detected. For example, if one is interested in detecting ventricular ischemia, one would select a window that includes the T-wave as data in the T-wave is known to be important in ventricular ischemia detection. See e.g. Camm, et al., eds. (2006) THE ESC TEXTBOOK OF CARDIOVASCULAR MEDICINE, Blackwell, which is herein incorporated by reference. Similarly, if one is interested in detecting hypertrophies, or myocardial or ventricular ischemia, one would select the QRS complex as the date in the QRS complex is known to be important in detection of hypertrophy and ischemia. See e.g. Camm, et al., eds. (2006) THE ESC TEXTBOOK OF CARDIOVASCULAR MEDICINE, Blackwell, which is herein incorporated by reference, which is herein incorporated by reference.

A characteristic window is obtained by selecting a portion of a cardiac cycle of interest which may be consistently identified by its relation to the beat marker. The start and end of a characteristic window have fixed-length distances in time relative to the beat marker. For example, a characteristic window comprising most of or all of the PQRST interval may be obtained by selecting the R-peak as the beat marker, selecting beats for which the RR interval fall within one standard deviation of the mean of the RR interval of the ECG, then for the selected beats designating a fixed length that is less than the minimum length of the RR interval of the selected beats such that the characteristic window overlaps with the PQRST interval, and the start and end of the characteristic window have fixed-length relations to the beat marker.

For example, the characteristic window comprising most of or all of the PQRST interval for an ECG sampled at 1000 samples per second, with a beat marker representing the R-peak, may be identified by:

1. Calculating the beat periods by using a beat marker representing the R-peak ($b_R[i]$, i=1, 2, ..., $N_{b0}$): $dn_{b0}[i] = b_R[i+1] - b_R[i]$, for beats i=1, 2, ..., $N_{b0} - 1$
2. Selecting non-arrhythmic beats by calculating the mean ($\mu_{b0}$) and standard deviation ($\sigma_{b0}$) of $dn_{b0}$, and selecting the beats such that the set of $N_b$ selected beat markers ($b_{Rs}$) is: $b_{Rs} = \{b_R[i]: \mu_{b0} - \sigma_{b0} < dn_{b0}[i] < \mu_{b0}\}$, for any i=2, 3, ..., $N_{b0} - 1$
3. Calculating the minimum beat periods ($N_{RR}$) using the beat marker:

$$N_{RR} = \min_i \{b_R[i+1] - b_R[i] : b_R[i] \epsilon b_{Rs}\}$$

4. Setting the characteristic window start points at $n = b_R[i] - 0.3 N_{RR}$ for the selected beats ($b_R[i] \epsilon b_{Rs}$)
5. Setting the characteristic window end points at $n = b_R[i] + 0.6 N_{RR}$ for the selected beats ($b_R[i] \epsilon b_{Rs}$)

2. Creating the Prime Morphological ECG

After the characteristic segments or the characteristic windows are identified, prime morphological ECG is then obtained by isolating the characteristic segments or the characteristic windows in the ECG by removing information extraneous to the characteristic segments or characteristic windows.

Figure 6A:
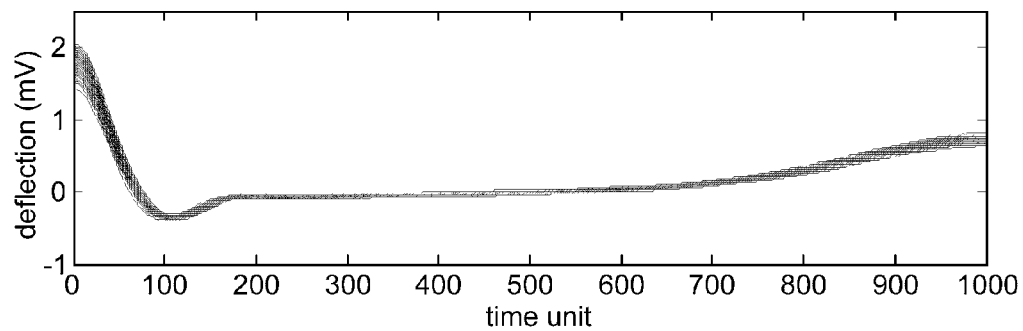
FIG. 6A shows an example of a characteristic segment. It is a group of length-1000 (1000 time units) RT characteristic segment from 60 beats of lead V5 of an ECG sampled at 1000 samples per second.

Characteristic segments or windows may be identified and isolated. As exemplified herein, a characteristic segment representing the RT segment is isolated from 12-lead ECG (sampled at 1000 samples per second) by identifying and isolating all selected RT segments. FIG. 6A shows an example of a group of RT characteristic segment from 60 beats of lead V5 of an ECG, in which the overlapping characteristic segment of the 60 beats appear substantially similar but not identical.

Figure 6B:
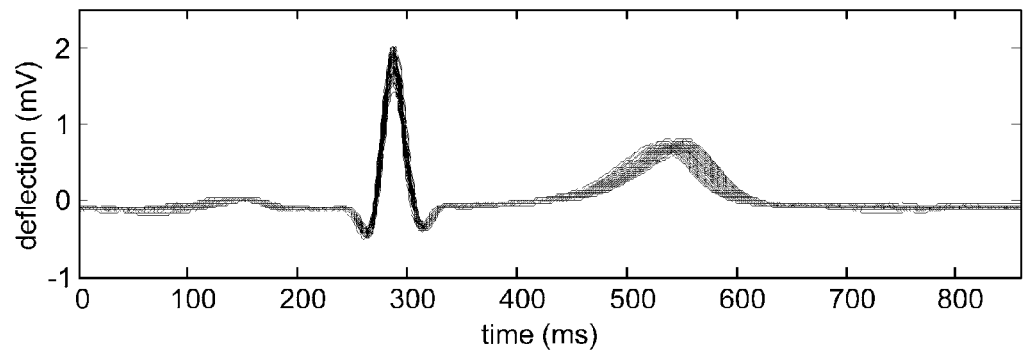
FIG. 6B shows an example of a characteristic window. It is a group of length-859 (859 ms) PQRST characteristic window from 60 beats of V5 of an ECG sampled at 1000 samples per second.

Similarly, characteristic windows may be identified and isolated. For example, a length-859 characteristic window representing the PQRST window is isolated from 12-lead ECG (sampled at 1000 samples per second) by identifying and isolating all selected PQRST windows. FIG. 6B shows an example of a group of PQRST characteristic window from 60 beats of lead V5 of an ECG, in which the overlapping characteristic window of the 60 beats appear substantially similar but not identical.

The isolated characteristic segment or the isolated characteristic segment has a fixed length from beat to beat, therefore arrhythmological information (arrhythmological aperiodicities such as leakage due to aperiodic windowing and periodic rate variability) is removed.

As exemplified herein, the characteristic segment comprising the RT characteristic segment of length-p of an ECG lead ($\{r_{RT,i}[1], r_{RT,i}[2], \ldots, r_{RT,i}[p]\}$), for selected beats i=1, 2, ..., $N_b$, is created by arranging in series the RT characteristic segment into a length-$pN_b$ sequence:

$$r_{RT} = \{r_{RT,1}[1], \ldots, r_{RT,1}[p] | r_{RT,2}[1], \ldots, r_{RT,2}[p] | \ldots | r_{RT,N_b}[1], \ldots, r_{RT,N_b}[p]\}$$

Figure 7A:
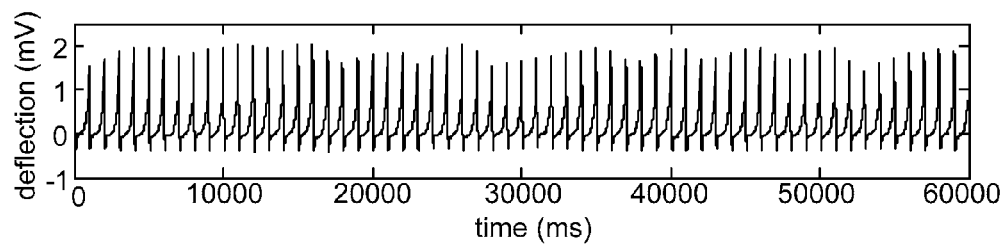
FIG. 7A shows RT as the characteristic segment in series which was created by arranging the group of RT characteristic segment of FIG. 6A in series.

FIG. 7A shows an example of a length-1000 (p=1000) RT characteristic segment of 60 selected beats in series.

Similarly, an example of the characteristic window comprising the PQRST characteristic window of length-q of an ECG lead ($\{r_{PQRST,i}[1], r_{PQRST,i}[2], \ldots, r_{PQRST,i}[q]\}$) sampled at 1000 samples per second, for selected beats i=1, 2, ..., $N_b$, is created by isolating and arranging in series the RT characteristic segment into a length-$qN_b$ sequence:

$$r_{PQRST} = \left\{ \begin{array}{c} r_{PQRST,1}[1], \ldots, \\ r_{PQRST,1}[q] \end{array} \middle| \begin{array}{c} r_{PQRST,2}[1], \ldots, \\ r_{PQRST,2}[q] \end{array} \middle| \ldots \middle| \begin{array}{c} r_{PQRST,N_b}[1], \ldots, \\ r_{PQRST,N_b}[q] \end{array} \right\}$$

Figure 7B:
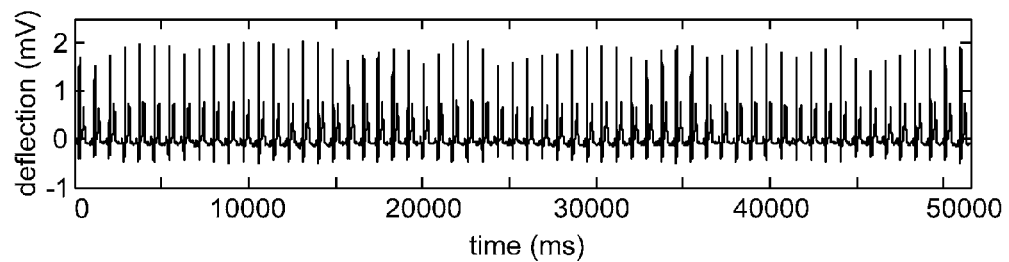
FIG. 7B shows PQRST as the characteristic window in series which was created by arranging the group of PQRST characteristic window of FIG. 6B in series.

FIG. 7B shows an example of a length-859 (q=859) PQRST characteristic window of 60 selected beats in series.

3. Refining the Characteristic Segment or Characteristic Window

Prior to creating the prime morphological ECG, the characteristic segment or the characteristic window may be refined by averaging the characteristic segment or the characteristic window. After removing the arrhythmological aperiodicities, the effects of morphological aperiodicities such as beat morphological variations, sub-fundamental frequency oscillations, and white noise may be reduced or removed by averaging.

The averaging of an ECG is a technique known in the art to reduce noise. The signal-averaged ECG (SAECG) is used in detection of sustained ventricular arrhythmias or sudden cardiac death in post-infarction patients, as well as in predicting cardiac and arrhythmic mortality. See Sierra et al. (1997) Proc. 19th Int'l Conf. IEEE/EMBS: 76, and Camm, et al., eds. (2006) THE ESC TEXTBOOK OF CARDIOVASCULAR MEDICINE, Blackwell, which are herein incorporated by reference.

Figure 8A:
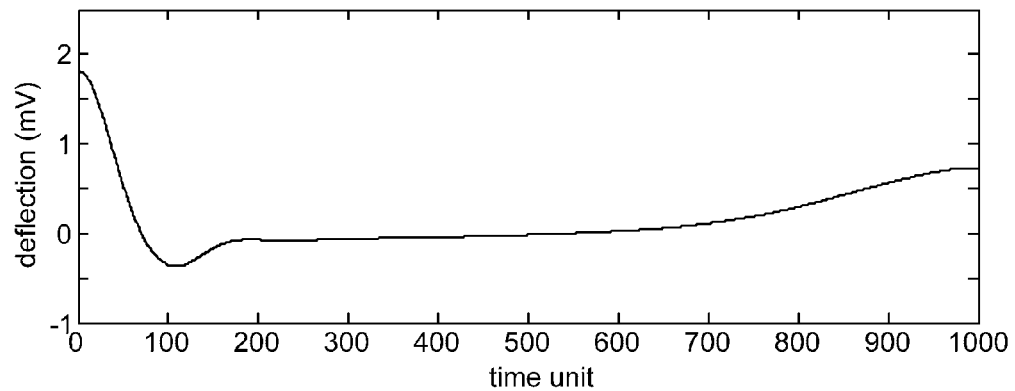
FIG. 8A shows the RT segment average which was created by taking the average of the deflections of the RT characteristic segment of FIG. 6A at each time unit.

As exemplified herein, the averaged RT characteristic segment ($\bar{r}_{RT}$) of length-p of an ECG lead $\{r_{RT,i}[1], r_{RT,i}[2], \ldots, r_{RT,i}[p]\}$, for selected beats i=1, 2, ..., $N_b$, is created by taking the average:

$$\bar{r}_{RT}[n] = \frac{1}{N_b} \sum_{i=1}^{N_b} r_{RT,i}[n],$$

n=1, 2, ..., p. FIG. 8A shows an example of the averaged RT characteristic segment of length-1000 of lead V5 of an ECG.

Figure 8B:
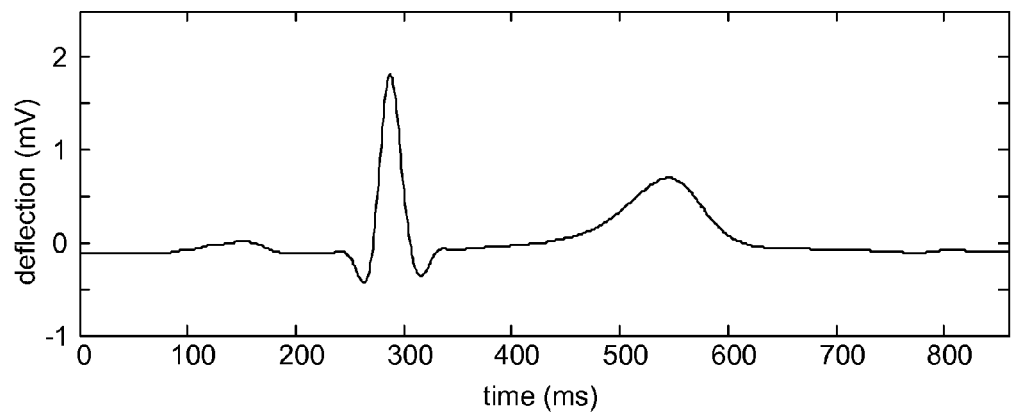
FIG. 8B shows the PQRST window average which was created by taking the average of the deflections of the PQRST characteristic window of FIG. 6B at each millisecond.

Similarly, an example that finds the averaged PQRST characteristic window ($\bar{r}_{PQRST}$) of length-q of an ECG lead $\{r_{PQRST,i}[1], r_{PQRST,i}[2], \ldots, r_{PQRST,i}[q]\}$, for selected beats i=1, 2, ..., $N_b$, is created by taking the average $$\bar{r}_{PQRST}[n] = \frac{1}{N_b} \sum_{i=1}^{N_b} r_{PQRST,i}[n],$$

n=1, 2, ..., q. FIG. 8B shows an example of the averaged PQRST characteristic window of length-859 of lead V5 of an ECG.

Alternatively, after averaging, the averaged characteristic segment or averaged characteristic window may be repeated by any positive integer number of times to give the same morphological information as the averaged characteristic segment or averaged characteristic window. For example, the averaged characteristic segment comprising the RT characteristic segment of length-p of an ECG lead $\bar{r}_{RT} = \{\bar{r}_{RT}[1], \bar{r}_{RT}[2], \ldots, \bar{r}_{RT}[p]\}$, is repeated several times to form a repeated averaged RT segment:

$$\ddot{r}_{RT} = \left\{ \begin{array}{c} \bar{r}_{RT}[1], \ldots, \bar{r}_{RT}[p] | \bar{r}_{RT}[1], \ldots, \bar{r}_{RT}[p] | \ldots \\ |\bar{r}_{RT}[1], \ldots, \bar{r}_{RT}[p] \end{array} \right\}.$$

Figure 9A:
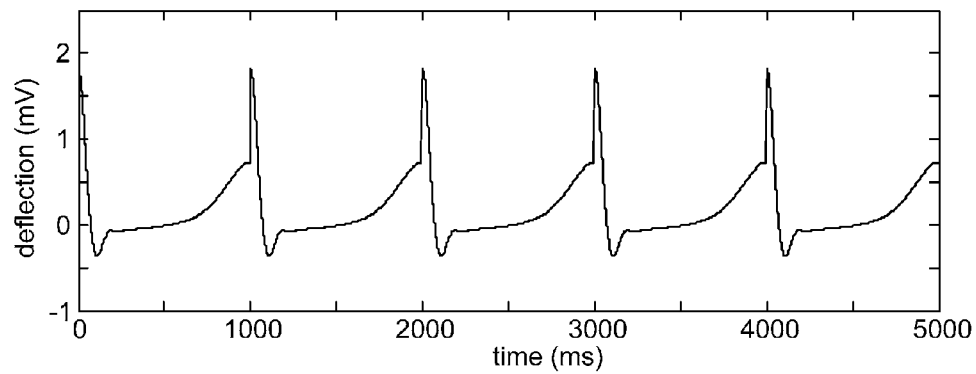
FIG. 9A shows 5000 time units of the RT segment average in series which was created by taking the RT segment average of FIG. 8A and repeating it 60 times.

FIG. 9A shows an example of the averaged RT characteristic segment of length-1000 of lead V5 of an ECG repeated 5 times. Similarly, for example, the averaged characteristic segment comprising the PQRST characteristic window of length-q of an ECG lead $\bar{r}_{PQRST} = \{\bar{r}_{PQRST}[1], \bar{r}_{PQRST}[2], \ldots, \bar{r}_{PQRST}[q]\}$, is repeated several times to form a repeated averaged PQRST window:

$$\ddot{r}_{PQRST} = \left\{ \begin{array}{c} \bar{r}_{PQRST}[1], \ldots, \bar{r}_{PQRST}[p] | \bar{r}_{PQRST}[1], \ldots, \bar{r}_{PQRST}[p] | \ldots \\ |\bar{r}_{PQRST}[1], \ldots, \bar{r}_{PQRST}[p] \end{array} \right\}.$$

Figure 9B:
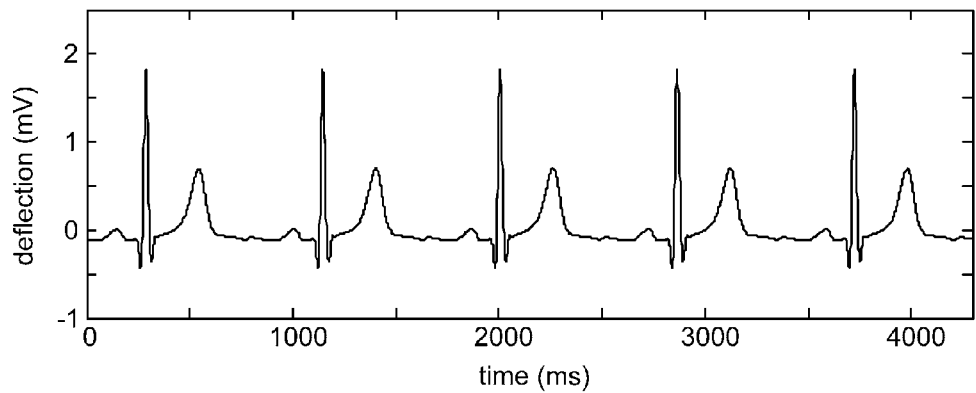
FIG. 9B shows 4295 ms of the PQRST window average in series which was created by taking the PQRST window average of FIG. 8B and repeating it 60 times.

FIG. 9B shows an example of the averaged PQRST characteristic window of length-859 of lead V5 of an ECG repeated 5 times.

4. Density Function of a Prime Morphological ECG

After the time-domain expression of a prime morphological ECG is obtained, morphological information of beats from the prime morphological ECG may be expressed as a density function. "Density" as applied to a prime morphological ECG is the harmonic peak energy (magnitude) of the discrete Fourier transform of the prime morphological ECG. "Density function" as applied to a prime morphological ECG is the density at a frequency (for a characteristic window) or a frequency unit (for a characteristic segment) equal to the sampling rate multiplied by the ordered number of the harmonic peak divided by the length of the period of the prime morphological ECG.

As exemplified herein, the discrete Fourier transform (DFT) of the prime morphological ECG, which includes (1) isolated characteristic segment or isolated characteristic window in series, (2) averaged characteristic segment or characteristic window, and (3) repetitions of averaged characteristic segment or characteristic window, is taken. The magnitude of the DFT of the prime morphological ECG at the harmonic frequencies or frequency locations of the prime morphological ECG are grouped and indexed to form the density function. Since the Fourier transform of a real sequence is symmetric, the distinct harmonics that form the density function is half of the total number of harmonics of the sequence in the frequency domain. See Oppenheim et al. (2006) SIGNALS AND SYSTEMS, Prentice, which is herein incorporated by reference.

Harmonics may be observed by taking the DFT of the isolated characteristic segment or isolated characteristic window in series. An isolated characteristic segment or characteristic window in series is created by identifying, isolating, and arranging in series the characteristic segment or the characteristic window of ECG. To observe the harmonics, first the magnitude of the DFT is taken of the isolated characteristic segment in series or the isolated characteristic window in series. Then the harmonic powers at the harmonic locations are grouped and indexed into the density function.

As exemplified herein, the harmonics of a length-$pN_b$ isolated characteristic segment comprising the RT characteristic segment of length-p of an ECG lead in series ($r_{RT} = \{r_{RT,1}[1], \ldots, r_{RT,1}[p] | r_{RT,2}[1], \ldots, r_{RT,2}[p] | \ldots | r_{RT,N_b}[1], \ldots, r_{RT,N_b}[p]\}$) is computed by:
 1. Taking the magnitude ($R_{RT}$) of the DFT of $r_{RT}$:

$$R_{RT}[k] = |\Sigma_{n=1}^{pN_b} r_{RT}[n] e^{-j2\pi k(n-1)/pN_b}|, k = 0, 1, \ldots, pN_b - 1$$

2. Grouping and indexing the harmonics into the density function ($h_{RT}$) by isolating the $R_{RT}$ at positive integer multiples of $N_b$:

$$h_{RT}[k] = R_{RT}[kN_b], k = 1, 2, \ldots, p/2 - 1$$

The frequency unit ($\tilde{f}$) of the isolated characteristic segment in series is defined as an integer multiple of the quotient the sampling rate ($f_s$), and the length of the isolated characteristic segment in series ($pN_b$):

$$\tilde{f}(k) = \frac{f_s k}{pN_b},$$

$k = 0, 1, \ldots, pN_b - 1$.

Figure 10A:
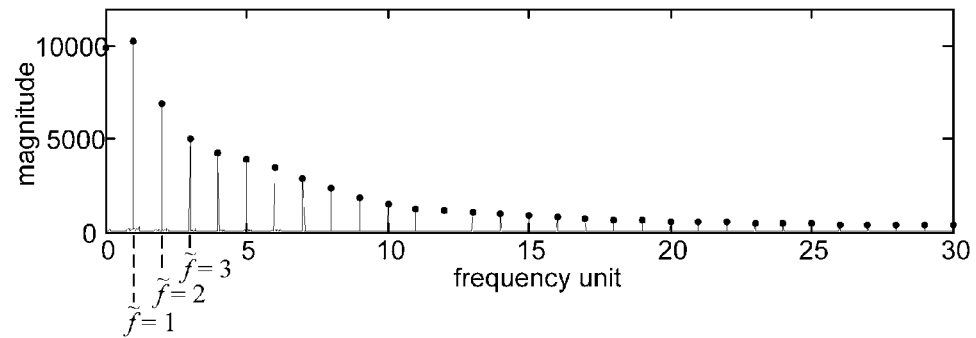
FIG. 10A shows the magnitude of the discrete Fourier transform of the RT characteristic segment in series of FIG. 7A from 0 to 30 frequency units.

FIG. 10A shows an example of the magnitude of the DFT of a length-1000 (p=1000) RT characteristic segment resampled to 1000 samples per second ($f_s$=1000) of 60 selected beats in series, in which the 1$^{st}$ harmonic peak is located at $$\tilde{f} = \frac{f_s(N_b)}{pN_b} = 1,$$

the 2$^{nd}$ harmonic peak is located at $$\tilde{f} = \frac{f_s(2N_b)}{pN_b} = 2,$$

the 3$^{rd}$ harmonic peak is located at $$\tilde{f} = \frac{f_s(3N_b)}{pN_b} = 3,$$

and so on.

Similarly, an example of the harmonics of a length-$qN_b$ isolated characteristic window comprising the PQRST characteristic window of length-q of an ECG lead in series $$\left( r_{PQRST} = \left\{ \begin{array}{c} r_{PQRST,1}[1], \ldots, \\ r_{PQRST,1}[q] \end{array} \middle| \begin{array}{c} r_{PQRST,2}[1], \ldots, \\ r_{PQRST,2}[q] \end{array} \middle| \ldots \middle| \begin{array}{c} r_{PQRST,N_b}[1], \ldots, \\ r_{PQRST,N_b}[q] \end{array} \right\} \right)$$

is computed by:
 1. Taking the magnitude ($R_{PQRST}$) of the DFT of $r_{PQRST}$:

$$R_{PQRST}[k] = |\Sigma_{n=1}^{qN_b} r_{PQRST}[n] e^{-j2\pi k(n-1)/qN_b}|, k = 0, 1, \ldots, qN_b - 1$$

2. Grouping and indexing the harmonics into the density function ($h_{PQRST}$):

$$h_{PQRST}[k] = R_{PQRST}[kN_b], k = 1, 2, \ldots, q/2 - 1$$

Figure 10B:
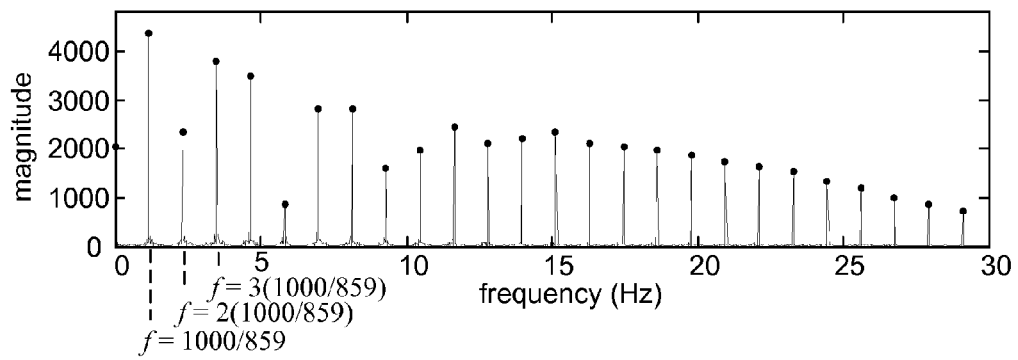
FIG. 10B shows the magnitude of the discrete Fourier transform of the PQRST characteristic window in series of FIG. 7B from 0 to 30 Hz.

FIG. 10B shows an example of the magnitude of the DFT of a length-859 (q=859) PQRST characteristic window sampled at 1000 samples per second ($f_s$=1000) of 60 selected beats in series, in which the 1$^{st}$ harmonic peak is located at $\tilde{f} = (f_s/q)(1) = 1000/859$ Hz, the 2$^{nd}$ harmonic peak is located at $\tilde{f} = (f_s/q)(2) = 2000/859$ Hz, the 3$^{rd}$ harmonic peak is located at $\tilde{f} = (f_s/q)(3) = 3000/859$ Hz, and so on.

Harmonics may be observed by taking the DFT of the averaged characteristic segment or averaged characteristic window. An averaged characteristic segment or characteristic window is created by identifying, isolating, and averaging the characteristic segment or the characteristic window of ECG. To observe the harmonics, first the magnitude of the DFT is taken of the averaged characteristic segment or the averaged characteristic window. Then the harmonic powers at the harmonic locations are grouped and indexed into the density function.

As exemplified herein, the harmonics of an averaged characteristic segment comprising the RT characteristic segment of length-p of an ECG lead ($\bar{r}_{RT} = \{\bar{r}_{RT}[1], \ldots, \bar{r}_{RT}[p]\}$) is computed by:

1. Taking the magnitude ($\bar{R}_{RT}$) of the point DFT of $\bar{r}_{RT}$:

$$\bar{R}_{RT}[k] = |\Sum_{n=1}^{p} \bar{r}_{RT}[n] e^{-j2\pi k(n-1)/p}|, k=0,1,\ldots,p-1$$

2. Grouping and indexing the harmonics into the density function ($\bar{h}_{RT}$):

$$\bar{h}_{RT}[k] = \bar{R}_{RT}[k], k=1,2,\ldots,p/-2-1$$

The frequency unit ($\tilde{f}$) of the averaged characteristic segment is defined as an integer multiple of the quotient the sampling rate ($f_s$), and the length of the isolated characteristic segment in series (p):

$$\tilde{f}(k) = \frac{f_s k}{p},$$

k=0, 1, ..., p−1.

Figure 11A:
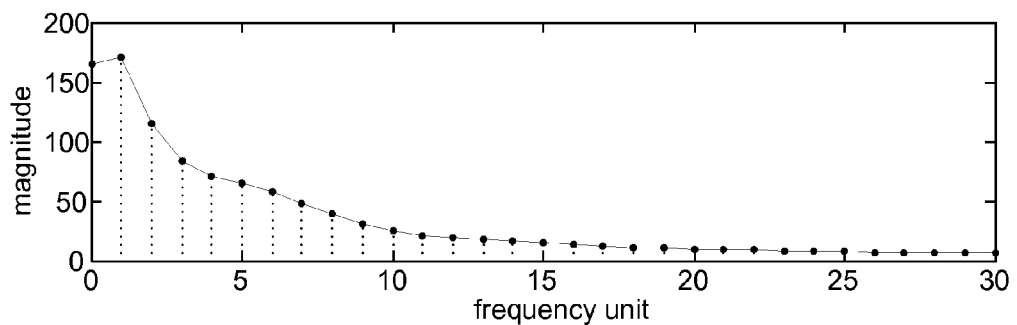
FIG. 11A shows the magnitude of the discrete Fourier transform of the RT characteristic segment average of FIG. 8A from 0 to 30 frequency units.

FIG. 11A shows an example of the magnitude of the DFT of a length-1000 (p=1000) averaged RT characteristic segment resampled to 1000 samples per second ($f_s$=1000), in which the $1^{st}$ harmonic peak is located at $\tilde{f}=f_s(1)/p=1$, the $2^{nd}$ harmonic peak is located at $\tilde{f}=f_s(2)/p=2$, the $3^{rd}$ harmonic peak is located at $\tilde{f}=f_s(3)/p=3$, and so on.

Similarly, an example of the harmonics of an averaged characteristic window comprising the PQRST characteristic window of length-q of an ECG lead ($\bar{r}_{PQRST} = \{\bar{r}_{PQRST}[1], \ldots, \bar{r}_{PQRST}[q]\}$) is computed by:

1. Taking the magnitude ($\bar{R}_{PQRST}$) of the DFT of $\bar{r}_{PQRST}$:

$$\bar{R}_{PQRST}[k] = |\Sum_{n=1}^{q} \bar{r}_{PQRST}[n] e^{-j2\pi k(n-1)/q}|, k=0,1,\ldots,q-1$$

2. Grouping and indexing the harmonics into the density function ($\bar{h}_{PQRST}$):

$$\bar{h}_{PQRST}[k] = \bar{R}_{PQRST}[k], k=1,2,\ldots,q/2-1$$

Figure 11B:
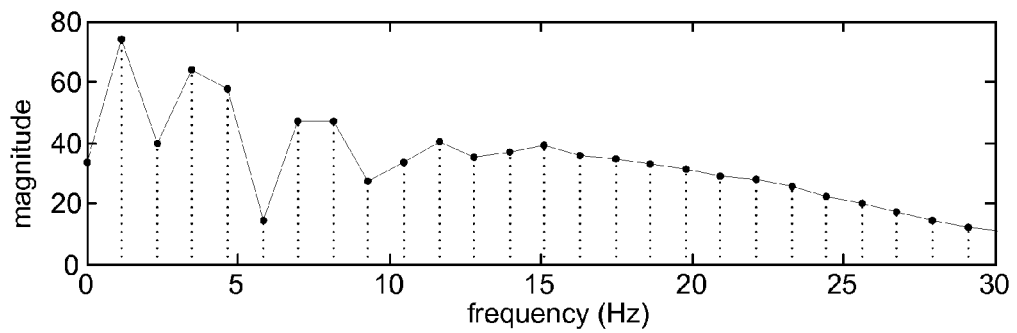
FIG. 11B shows the magnitude of the discrete Fourier transform of the PQRST characteristic window average of FIG. 8B from 0 to 30 Hz.

FIG. 11B shows an example of the magnitude of the DFT of a length-859 (q=859) averaged PQRST characteristic window sampled at 1000 samples per second ($f_s$=1000), in which the $1^{st}$ harmonic peak is located at $\tilde{f}=(f_s/q)(1)=1000/859$ Hz, the $2^{nd}$ harmonic peak is located at $\tilde{f}=(f_s/q)(2)=2000/859$ Hz, the $3^{rd}$ harmonic peak is located at $\tilde{f}=(f_s/q)(3)=3000/859$ Hz, and so on.

Harmonics may be observed by taking the DFT of the repeated averaged characteristic segment or repeated averaged characteristic window. A repeated averaged characteristic segment or characteristic window is created by repeating the averaged characteristic segment or the averaged characteristic window of ECG. To observe the harmonics, first the magnitude of the DFT is taken of the repeated averaged characteristic segment or the repeated averaged characteristic window. Then the harmonic powers at the harmonic locations are grouped and indexed into the density function.

As exemplified herein, the harmonics of an averaged characteristic segment comprising the RT characteristic segment of length-p of an ECG lead and repeated $N_M$ times $$\ddot{r}_{RT}:$$

is computed by:

1. Taking the magnitude $$(\ddot{R}_{RT})$$

of the DFT of $$\left( \ddot{r}_{RT} = \begin{cases} \bar{r}_{RT}[1], \ldots, \bar{r}_{RT}[p] | \bar{r}_{RT}[1], \ldots, \bar{r}_{RT}[p] | \ldots \\ |\bar{r}_{RT}[1], \ldots, \bar{r}_{RT}[p] \end{cases} \right\}, \text{length} - pN_M \right)$$

$$\ddot{R}_{RT}[k] = \left| \Sum_{n=1}^{pN_M} \ddot{r}_{RT}[n] e^{-j2\pi k(n-1)/pN_M} \right|, k = 0, 1, \ldots, pN_M - 1$$

2. Grouping and indexing the harmonics into the density function $$(\ddot{h}_{RT}):$$

$$\ddot{h}_{RT}[k] = \ddot{R}_{RT}[kN_M],$$

k=1, 2, ..., p/2−1

The frequency unit $$(\tilde{\tilde{f}})$$

of the repeated averaged characteristic segment is defined as an integer multiple of the quotient the sampling rate ($f_s$), and the length of the isolated characteristic segment in series ($pN_M$):

$$\tilde{\tilde{f}} = \frac{f_s k}{pN_M},$$

k=0, 1, ..., $pN_M$−1.

Figure 12A:
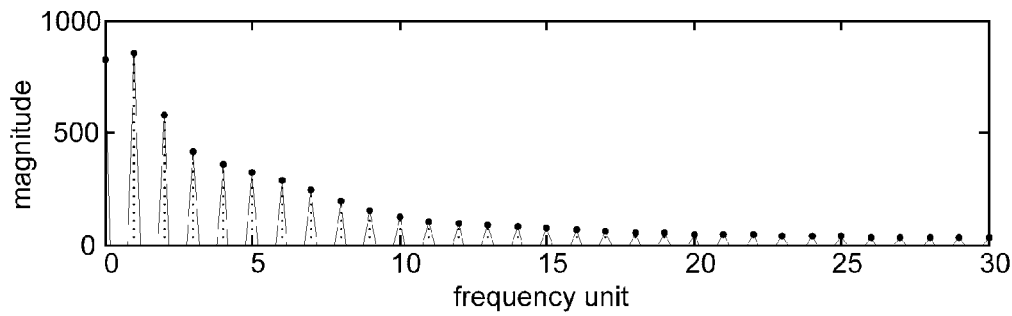
FIG. 12A shows the magnitude of the discrete Fourier transform of the RT characteristic segment average in series of FIG. 9A from 0 to 30 frequency units.

FIG. 12A shows an example of the magnitude of the DFT of a length-1000 (p=1000) averaged RT characteristic segment resampled to 1000 samples per second ($f_s$=1000) repeated 5 times ($N_M$=5), in which the $1^{st}$ harmonic peak is located at $$\tilde{\tilde{f}} = \frac{f_s(N_M)}{pN_M} = 1,$$

the 2$^{nd}$ harmonic peak is located at $$\tilde{\tilde{f}} = \frac{f_s(2N_M)}{pN_M} = 2,$$

the 3$^{rd}$ harmonic peak is located at $$\tilde{\tilde{f}} = \frac{f_s(3N_M)}{pN_M} = 3,$$

and so on.

Similarly, an example of the harmonics of an averaged characteristic segment comprising the PQRST characteristic window of length-q of an ECG lead and repeated $N_M$ times $$(\tilde{r}_{PQRST} = \{\tilde{r}_{PQRST}[1], \ldots, \tilde{r}_{PQRST}[q] | \tilde{r}_{PQRST}[1],$$
$$\ldots, \tilde{r}_{PQRST}[q] | \ldots | \tilde{r}_{PQRST}[1], \ldots, \tilde{r}_{PQRST}[q]\},$$

length-$qN_M$) is computed by:

1. Taking the magnitude $$(\tilde{R}_{PQRST})$$

of the $qN_M$-point DFT of $$\tilde{r}_{PQRST}:$$

$$\tilde{R}_{PQRST}[k] = \left| \sum_{n=1}^{qN_M} \tilde{r}_{PQRST}[n] e^{-j2\pi k(n-1)/qN_M} \right|, k = 0, 1, \ldots, qN_M - 1$$

2. Grouping and indexing the harmonics into the density function ($\tilde{\tilde{h}}_{PQRST}$):

$$\tilde{\tilde{h}}_{PQRST}[k] = \tilde{\tilde{R}}_{PQRST}[kN_M], k = 1, 2, \ldots, q/2 - 1$$

Figure 12B:
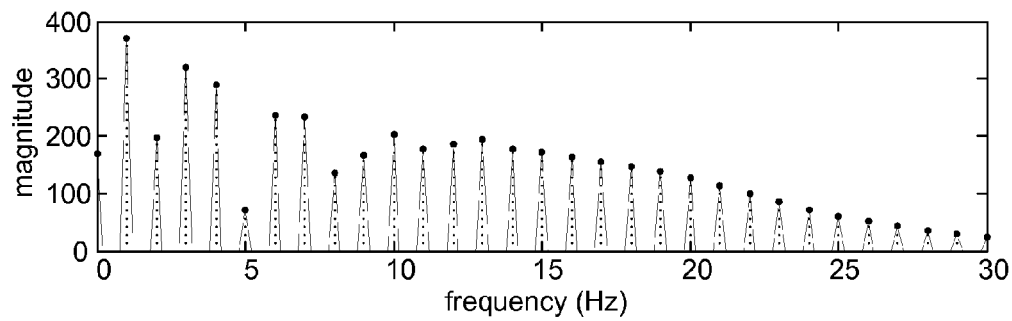
FIG. 12B shows the magnitude of the discrete Fourier transform of the PQRST characteristic window average in series of FIG. 9B from 0 to 30 Hz.

FIG. 12B shows an example of the magnitude of the DFT of a length-859 (q=859) averaged PQRST characteristic window sampled at 1000 samples per second ($f_s$=1000) repeated 5 times ($N_M$=5), in which the 1$^{st}$ harmonic peak is located at $\tilde{f}=(f_s/q)(1)$=1000/859 Hz, the 2$^{nd}$ harmonic peak is located at $\tilde{f}=(f_s/q)(2)$=2000/859 Hz, the 3$^{rd}$ harmonic peak is located at $\tilde{f}=(f_s/q)(3)$=3000/859 Hz, and so on.

The above examples $$(h_{RT}, \bar{h}_{RT}, \ddot{h}_{RT}, h_{PQRST}, \bar{h}_{PQRST}, \ddot{h}_{PQRST})$$

show that, regardless of how many distinct or similar (averaged) characteristic segments or characteristic windows are used or repeated in the creation of the density function, the length of the density function is half the length of one characteristic segment or one characteristic window.

5. Distribution Function of a Prime Morphological ECG

After the density function is obtained, an accounting of the distribution of the energy of the harmonics may be calculated. "Distribution" as applied to a prime morphological ECG is the sum of the density from zero to a given frequency (for a characteristic window) or a frequency unit (for a characteristic segment) equal to the sampling rate multiplied by the ordered number of the harmonic peak divided by the length of the period of the prime morphological ECG. "Distribution function" as applied to a prime morphological ECG is the sum of the density functions over a given range of harmonics. In some embodiments, the sum is a weighted sum. Those skilled in the art may readily optimize the weight a sum is given for a desired application.

As exemplified herein, the distribution function (H) of a density function ($h_{RT}[k]$, k=1, 2, ..., p/2−1) of a prime morphological ECG created from an RT characteristic segment of length-p of an ECG lead, is computed by: $H[k]=\Sigma_{l=1}^{k} h_{RT}[l]$, for k=1, 2, ..., p/2−1.

Similarly, an example of the distribution function (H) of a density function ($h_{PQRST}[k]$, k=1, 2, ..., q/2−1) of a prime morphological ECG created from a PQRST characteristic window of length-q of an ECG lead, is computed by: $H[k]=\Sigma_{l=1}^{k} h_{PQRST}[l]$, for k=1, 2, ..., q/2−1. The lead of the harmonic distribution function is denoted by the subscript. For example, $H_{aVL}[k]$ is the harmonic distribution of lead aVL.

B. Prime Arrhythmological ECG

Once the ECG is obtained, a prime arrhythmological ECG is made by isolating the arrhythmological information of beats from the ECG by making the morphological information constant, and may further include refining the arrhythmological information.

There are a variety of methods known in the art for isolating arrhythmological information, such as normal-to-normal (NN) interval variability methods that include the RR interval variability analysis and the like, and time interval variability methods that include QT interval variability analysis, RT interval variability analysis, and the like. See Kurths et al. (1995) Chaos 5(1):88, Berger et al. (1997) Circulation 96(5): 1557, and Sosnowski et al. (2001) Europace 3:39, which are herein incorporated by reference. There are a variety of devices known in the art for isolating arrhythmological information based on these prior art methods, such devices include the HOLTER MONITORING SYSTEM® available from Philips (Amsterdam, Netherlands), the CARDIO HOLTER ECG SYSTEM® available from Nasiff Associates (Brewerton, N.Y.), and the like.

Unfortunately, prior art interval variability methods provide limited arrhythmological information for the analysis of harmonic disintegration caused by arrhythmological aperiodicities such as leakage due to aperiodic windowing and periodic rate variability.

As provided herein, a prime arrhythmological ECG is made by a waveform train. A "waveform train" is a series of waveforms over time periods in the time domain, wherein all the waveforms have the same morphology over these time periods, and wherein no partial period is present. An ideal waveform train is a waveform train in which all waveforms are spaced equidistant from each other. A waveform train based on an ECG is a waveform train in which the waveform at each beat is placed in relation to a beat marker of the ECG.

1. Isolating Arrhythmological Information

Once the ECG is obtained, then beat markers for the beats are selected as disclosed herein.

2. Creating the Prime Arrhythmological ECG

After the beat marker is selected and the arrhythmological information is isolated, a waveform train may be created based on the beat markers. Waveforms trains known in the art include the impulse train (Dirac comb), the square wave, the triangular wave, the sawtooth wave, the sine wave, the cosine wave, and the like. See Oppenheim et al. (2006) SIGNALS AND SYSTEMS, Prentice, which is herein incorporated by reference.

The choice of the waveform for the waveform train depends on the desired transform domain response. Transform domain response may be observed by taking a transform of the ideal discrete-time waveform train. For example, an ideal discrete-time impulse train has a frequency-domain response of a train of impulses of equal heights. An ideal discrete-time sine wave has a frequency-domain response of a single impulse. An ideal discrete-time square wave has a frequency-domain response of a train of impulses logarithmically decreasing with an increase in frequency. See Oppenheim et al. (2006) SIGNALS AND SYSTEMS, Prentice, which is herein incorporated by reference.

Figure 13A:
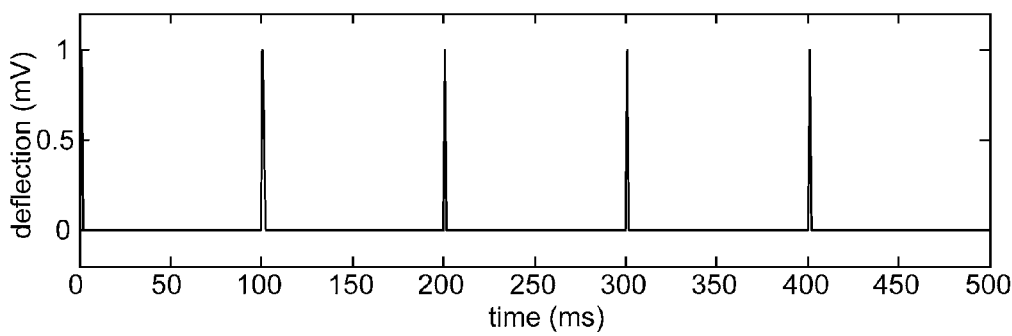
FIG. 13A shows 0.5 second of an ideal impulse train at a sampling rate of 1000 samples per second and spaced 100 ms apart.
Figure 13B:
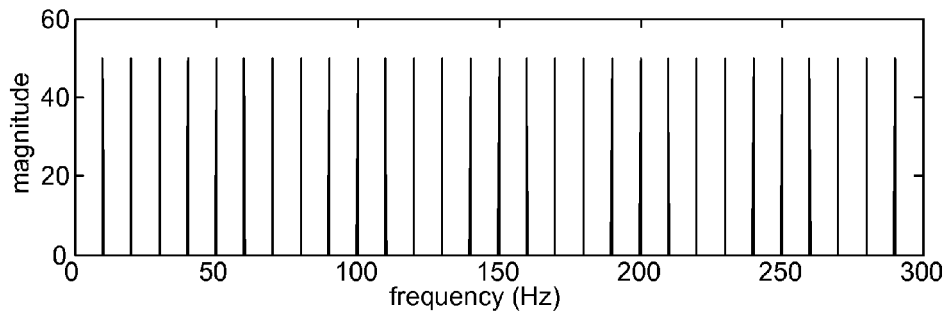
FIG. 13B shows the magnitude of the discrete Fourier transform of the ideal impulse train of FIG. 13A from 0 to 300 Hz.
Figure 13C:
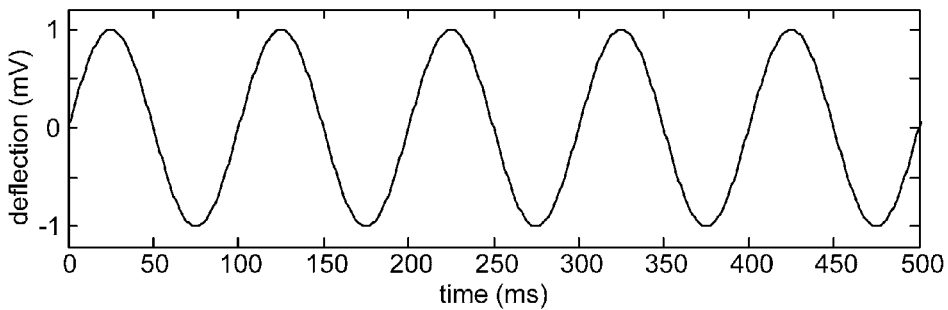
FIG. 13C shows 0.5 seconds of an ideal sine wave at a sampling rate of 1000 samples per second, at a magnitude of one and period of 100 ms.
Figure 13D:
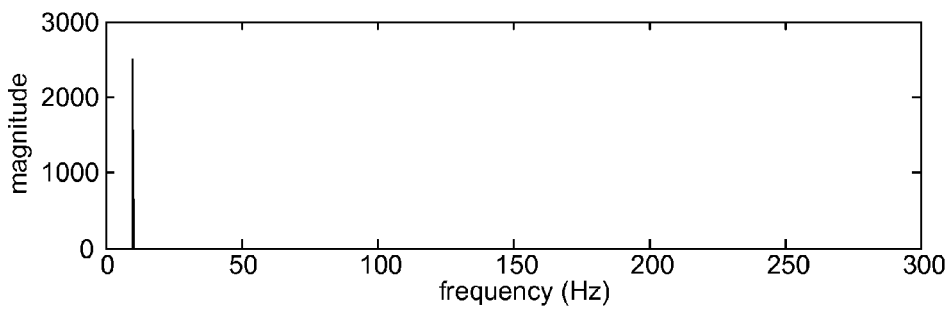
FIG. 13D shows the magnitude of the discrete Fourier transform of the ideal sine wave of FIG. 13C from 0 to 300 Hz.
Figure 13E:
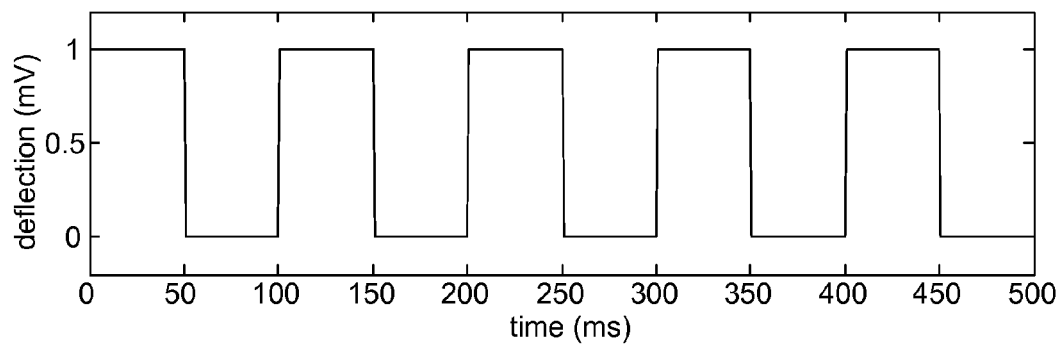
FIG. 13E shows an ideal square wave at a sampling rate of 1000 samples per second, at a magnitude of one and period of 100 ms.
Figure 13F:
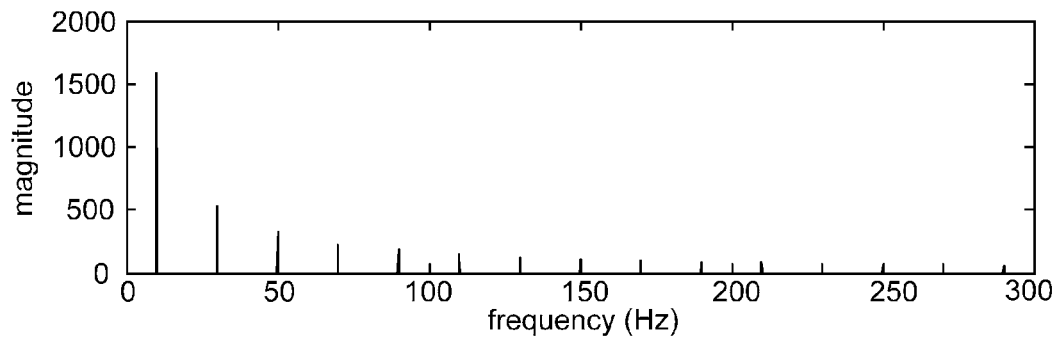
FIG. 13F shows the magnitude of the discrete Fourier transform of the ideal square wave of FIG. 13E from 0 to 300 Hz.
Figure 13G:
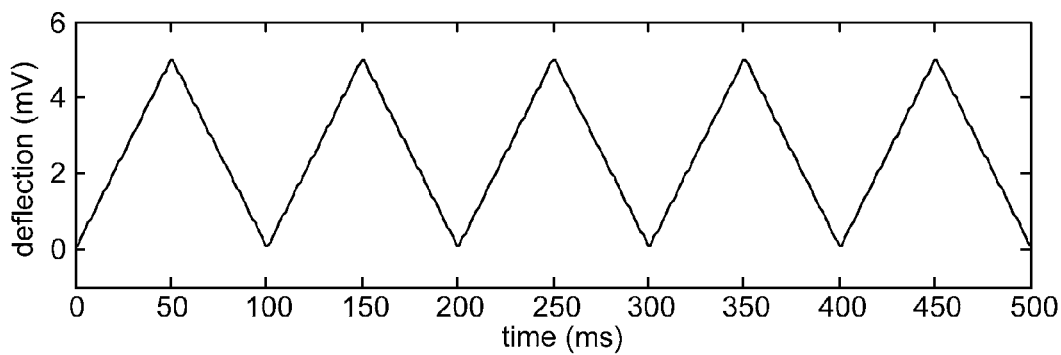
FIG. 13G shows an ideal triangle wave.
Figure 13H:
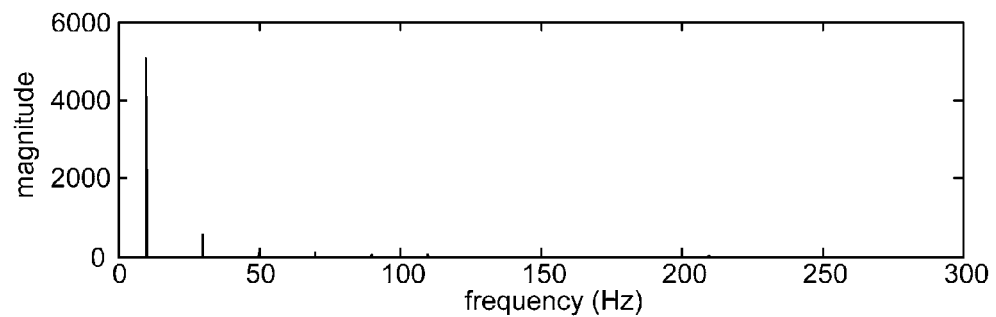
FIG. 13H shows the magnitude of the discrete Fourier transform of the ideal triangle wave of FIG. 13G from 0 to 300 Hz.

FIG. 13A shows an example of an ideal impulse train and FIG. 13B its frequency-domain transform. FIG. 13C shows an example of an ideal sine wave train and FIG. 13D its frequency-domain transform. FIG. 13E shows an example of an ideal square wave train and FIG. 13F its frequency-domain transform. FIG. 13G shows an example of an ideal triangular wave train and FIG. 13H its frequency-domain transform.

As exemplified herein, an impulse train based on a beat marker of an ECG representing the R-peak was created by first identifying a beat marker representing the R-peak for all beats. An impulse train of the same length as the ECG in which the value at the beat marker for each beat is 1, and the value at all other time locations for each beat was zero, is created. Then any partial beat at the start or the end of the impulse train was removed. An impulse train based on a beat marker representing the R-peak ($b_R[i]$, i=1, 2, ..., $N_{b0}$), for beats i=1, 2, ..., $N_{b0}$ for a length-N ECG sampled at 1000 samples per second is created by:

1. Creating a sequence of zeros ($a_{I0}$) of length N: $a_{I0}[n]=\{0: n=1, 2, \ldots, N\}$
2. Changing the values of $a_I$ at beat marker locations to 1:

$$a_{I0}[n]=\{1:n=b_R[1],b_R[2],\ldots,b_R[N_{b0}]\}$$

3. Removing any partial beats to create the impulse train ($a_I$):

$$a_I[n]=a_{I0}[n+b_R[1]-1], n=1,2,\ldots,b_R[N_{b0}]-b_R[1]$$

Figure 14:
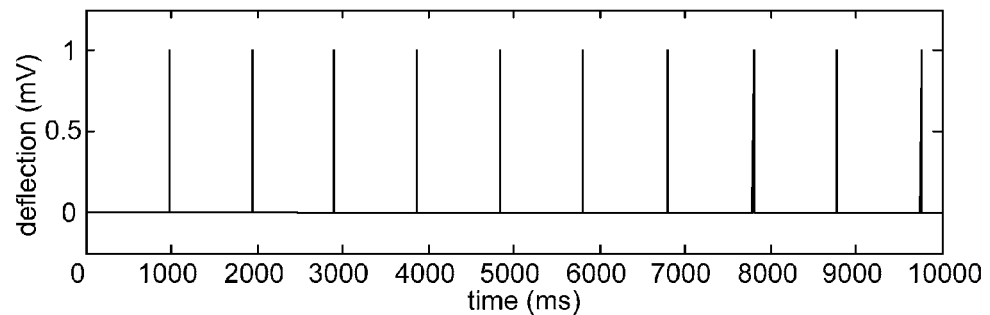
FIG. 14 shows an impulse train of a waveform window which was created by taking an ECG sampled at 1000 samples per second and making all of its deflections zero except for its R peak locations, which are set to a deflection of one.

FIG. 14 shows an example of the impulse train based on an R-wave beat marker of an ECG sampled at 1000 samples per second.

3. Refining the Prime Arrhythmological ECG

Prior to creating the prime arrhythmological ECG, the waveform train may be refined by using a waveform that is specific to the type of transform to be taken for subsequent transform-domain analysis. Time-domain simplicity does not imply transform-domain simplicity. For example, the impulse train, which represents the simplest waveform train in the time-domain, has the appearance of an impulse train in the frequency domain, as shown in FIG. 13B. In contrast, the sine wave, being of a higher complexity compared to the impulse train, has the appearance of a single impulse in the frequency domain, as shown in FIG. 13D.

The choice of the waveform for the refinement of the waveform train depends on the type of transform to be taken. For example, if one is interested in using a discrete sinusoidal transform such as the discrete Fourier transform or the discrete cosine transform (DCT), one would select the a sinusoid such as a sine wave or a cosine wave, as sinusoids form the basis for sinusoidal transforms. See Oppenheim et al. (2006) SIGNALS AND SYSTEMS, Prentice, which is herein incorporated by reference. Similarly, if one is interested in using a discrete wavelet transform such as a Daubechies transform, one would select a wavelet such as a Daubechies wavelet as wavelets form the basis for wavelet transforms. See Stark (2005) WAVELETS AND SIGNAL PROCESSING, Springer, which is herein incorporated by reference.

For example, a discrete sine wave based on a beat marker of an ECG representing the R-peak was created by first identifying a beat marker representing the R-peak for all beats. The beat periods in between the beat marker of the identified beats were then computed. Then for each beat the sine function was taken of the range of zero to $2\pi$ ($[0,2\pi]$) divided over the beat period, and was placed into the beat in place of the ECG. Then any partial beat at the start or the end of the impulse train was excluded.

For example, a sine wave of the range $[0,2\pi]$, based on a beat marker representing the R-peak ($b_R[i]$, i=1, 2, ..., $N_{b0}$), for beats i=1, 2, ..., $N_{b0}$ for a length-N ECG sampled at 1000 samples per second is created by:

1. Computing the beat periods ($dn_{b0}$): $dn_{b0}[i]=b_R[i+1]-b_R[i]$, for beats i=1, 2, ..., $N_{b0}-1$
2. Dividing the range $[0,2\pi]$ over each beat period $dn_{b0}[i]$ (i=1, 2, ..., $N_{b0}-1$) to get a time sequence ($t_i$) at each beat:

$$t_i[n] = \frac{2\pi n}{dn_{b0}[i]}, n = 1, 2, \ldots, dn_{b0}[i]$$

3. Computing the sine function of $t_i[n]$ for each beat period, and replacing the ECG of this period with the sine function to form the length-$N-b_R[N_b]-b_R[1]$ waveform train ($a_s$):

$$a_s=\{\sin(t_1[1]),\ldots,\sin(t_1[dn_{b0}[1]])|\sin(t_2[2]),\ldots,\sin(t_2[dn_{b0}[2]])|\ldots|\sin(t_{N_b-1}[1]),\ldots,\sin(t_{N_b-1}[dn_{b0}[N_b-1]])\}$$

Figure 15:
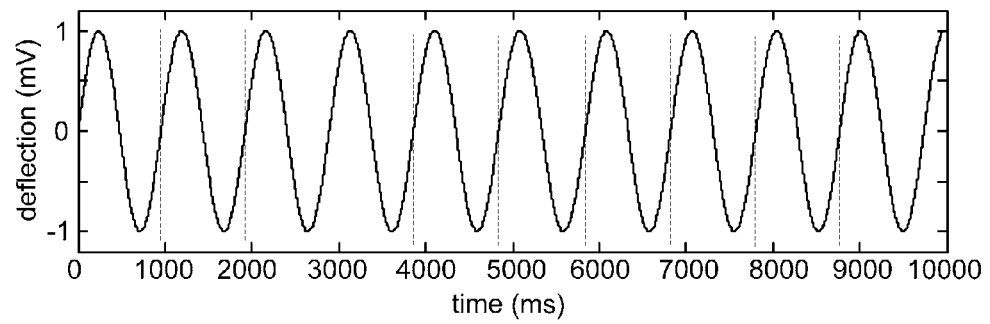
FIG. 15 shows a sine waveform segment which was created by taking the same ECG of FIG. 14 and replacing each beat with one period (0~2π) of the sine wave with magnitude one.

FIG. 15 shows an example of the sine waveform train based on an R-wave beat marker of an ECG sampled at 1000 samples per second. This is an example of frequency modulation (FM), in which sinusoids of a constant magnitude but varying frequencies are arranged in series in time to convey information. See Proakis (2000) DIGITAL COMMUNICATIONS, McGraw-Hill, which is herein incorporated by reference.

4. Density Function of a Prime Arrhythmological ECG

After the time-domain expression of a prime arrhythmological ECG is obtained, arrhythmological information of beats from the ECG may also be expressed as a density function. "Density" as applied to a prime arrhythmological ECG is the spectral energy attributable to each harmonic. "Density function" as applied to a prime arrhythmological ECG is the spectral energy at a range of frequencies relative to the frequency of a harmonic.

The density may be obtained by taking the DFT of an impulse train based on a beat marker represented by the R-peak of an ECG. First, an impulse train based on an ECG is created. Then the magnitude of the DFT is taken of the impulse train to compute the density.

For example, the density of a length-$N_I$ impulse train based on a beat marker representing by the R-peak of an ECG ($a_I[n]$) n=1, 2, ..., $N_I$ is computed by taking magnitude of the DFT of the impulse train ($m_I$): $m_I[k]=|\Sigma_{n=1}^{N_I} a_I[n] e^{-j2\pi k(n-1)/qN_I}|$, k=1, 2, ..., N/2−1.

Figure 16:
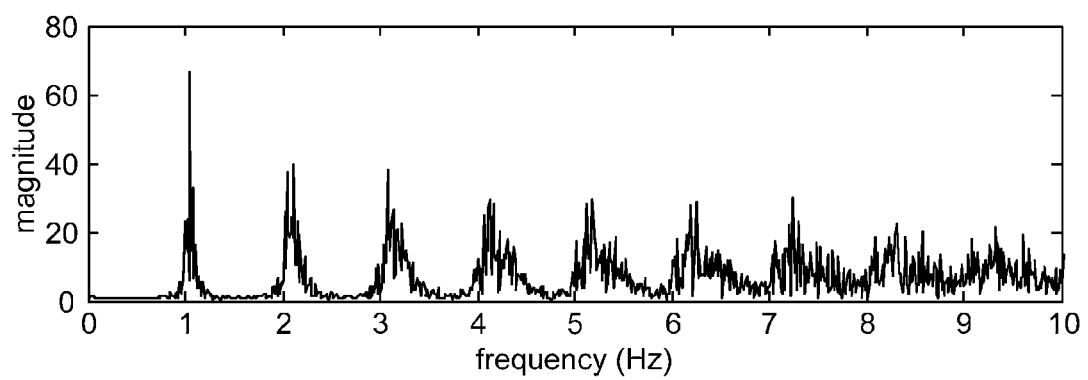
FIG. 16 shows the magnitude of the discrete Fourier transform of the impulse train of the waveform window of FIG. 14 from 0 to 10 Hz.

FIG. 16 shows an example of the density of an impulse train based on an R-wave beat marker of an ECG sampled at 1000 samples per second.

The density may also be obtained by taking the DFT of a sine waveform train based on a beat marker represented by the R-peak of an ECG. First, a sine waveform train based on an ECG is created. Then the magnitude of the DFT is taken of the sine waveform train to compute the density.

For example, the density of a length-$N_S$ waveform train based on a beat marker representing by the R-peak of an ECG ($a_S[n]$) n=1, 2, ..., $N_S$ is computed by taking magnitude of the DFT of the waveform train ($m_S$): $m_S[k]=|\Sigma_{n=1}^{N_S} a_S[n] e^{-j2\pi k(n-1)/qN_S}|$, k=1, 2, ..., N/2−1.

Figure 17:
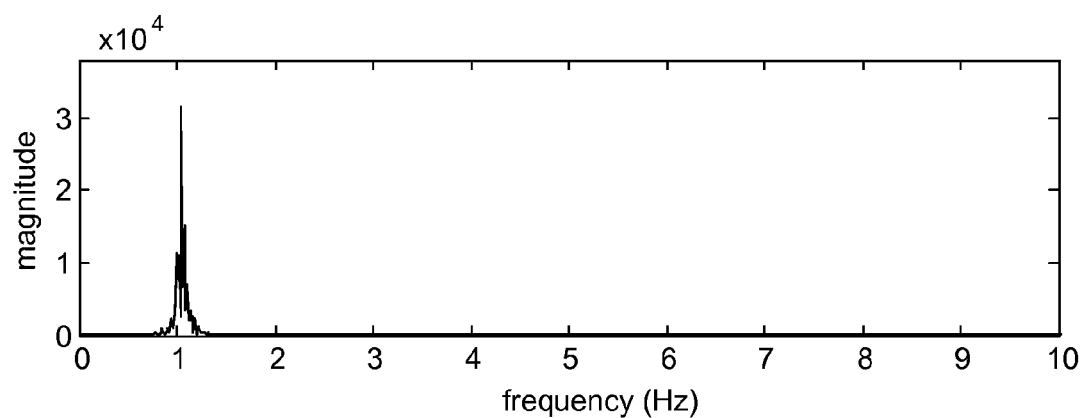
FIG. 17 shows the magnitude of the discrete Fourier transform of the sine waveform segment of FIG. 15 from 0 to 10 Hz.

FIG. 17 shows an example of the density of a sine waveform train based on an R-wave beat marker of an ECG sampled at 1000 samples per second.

5. Distribution Function of a Prime Arrhythmological ECG

After the density function is obtained, an accounting of the distribution of the energy of the density may be calculated. "Distribution" as applied to a prime arrhythmological ECG is the sum of the density from a range of frequencies. "Distribution function" as applied to a prime arrhythmological ECG is the sum of the density functions over a given range of frequencies. In some embodiments, the sum is a weighted sum. Those skilled in the art may readily optimize the weight a sum is given for a desired application.

As exemplified herein, the distribution function (M) of a density function (m[k], k=1, 2, ..., N/2−1) of a prime arrhythmological ECG, is computed by: $M[k]=\Sigma_{l=1}^{k} m[l]$, for k=1, 2, ..., N/2−1.

III. Applications—Correlating to Heart Disease and Disorders

After a prime ECG is created, it may be correlated to heart conditions using statistical pattern recognition techniques and used to classify or diagnose a subject as having a given heart condition. There are two approaches to pattern recognition: statistical pattern recognition and syntactic pattern recognition. The statistical approach classifies patterns based on the assumption that the relationship between pattern and classification is probabilistic. Syntactic pattern recognition classifies patterns based on a priori knowledge (syntax) of the relationship between patterns and classification. See Jain et al. (2000) IEEE Trans. on Pattern Analysis and Machine Intelligence 22(1): 4, which is herein incorporated by reference.

Pattern recognition of the present invention does not assume a priori knowledge of the relationship between any transform-domain expression of the ECG and a given abnormal heart condition such as ischemia or hypertrophies. However, given sufficient patterns that are statistically recognized or other advances in the art, an a priori knowledge rule base may be created to enable syntactic pattern recognition in the future.

Statistical pattern recognition is done by (1) obtaining multiple sets of patterns and their corresponding classifications (the training sets), and then (2) by determining the classification boundaries in the space spanned by the patterns that correspond to the training set classifications. See Jain et al. (2000) IEEE Trans. on Pattern Analysis and Machine Intelligence 22(1): 4, which is herein incorporated by reference.

The determination of classification boundaries in the space spanned by the patterns may be done using any number of statistical pattern recognition methods such as analysis of variance between groups (ANOVA), analysis of covariance (ANCOVA) between groups, autoregressive moving average (ARMA) models, neural networks, Kalman filter, and other methods known in the art. The determination of classification boundaries in the space spanned by the patterns may also be done using commercially available statistical software such as Statistica® available from StatSoft, Inc. (Tulsa, Okla.), SPSS® available from SPSS Inc. (Chicago, Ill.), and Matlab® available from The MathWorks, Inc. (Natick, Mass.).

As exemplified herein, multiple sets of patterns and their corresponding classification are obtained. First, patterns formed from resource-limited observations (RLO), such as various lead systems of ECG, such as the Frank-lead, EASI lead, 12-lead, and the like, and basic patient data such as age, gender, body mass index, conditions of diabetes, smoking, hypertension, dyslipidemia, and the like were collected from more than about 1000 subjects having a diverse array of clinically diagnosed heart conditions. Classifications of the same 1000 subjects were diagnosed by experienced cardiologists using prior art resource-rich observation (RRO) methods known in the art including exercise ECG, echocardiography, SPECT Thallium-201 scan, angiography, and a combination thereof, to diagnose heart diseases or disorders that included the presence or absence of myocardial ischemia, hypertrophies, conduction blocks, arrhythmias, cardiomyopathies, and the like. The subjects were further classified into one of two groups, "normal" and "ischemic," by experienced cardiologists using diagnostic methods known in the art. As exemplified herein, the determination of the classification boundaries of ischemia in the space spanned by the patterns was done using the statistical simulation software Statistica® available from StatSoft, Inc. (Tulsa, Okla.).

A. Density of Prime Morphological ECG

Figure 18A:
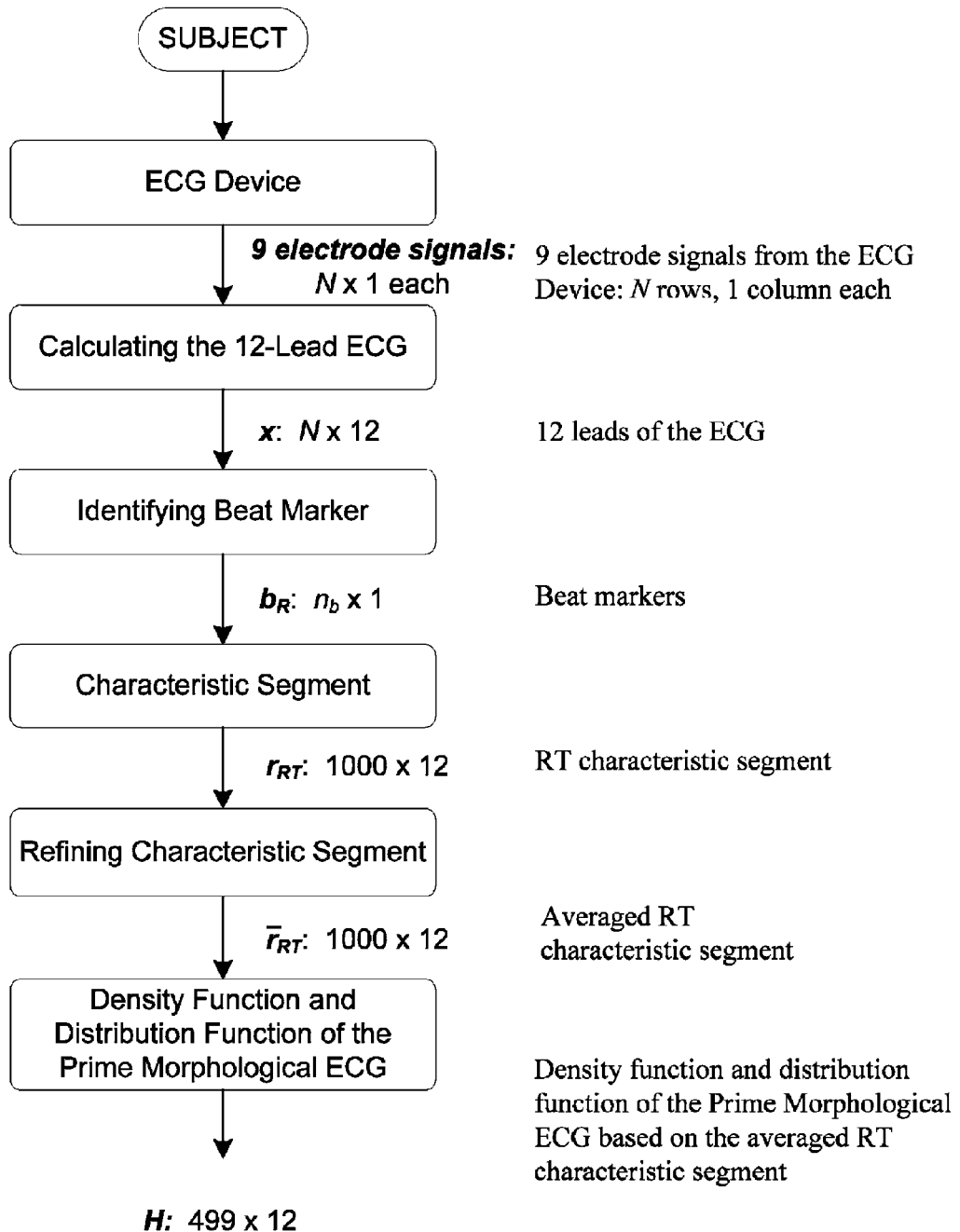
FIG. 18A schematically shows a method for obtaining the density function of the prime morphological ECG of a subject.

FIG. 18A schematically shows a method for obtaining the density function of the prime morphological ECG of a subject. FIG. 18A1 schematically shows the steps for calculating the 12-lead ECG and identifying the beat marker. FIG. 18A2 schematically shows obtaining the characteristic segment. FIG. 18A3 schematically shows refining the characteristic segment and obtaining the density and distribution. FIG. 18B outlines the steps in FIGS. 18A and 18A1 to 18A3.

After the prime morphological ECG is created, ECG may be correlated to heart conditions using statistical pattern recognition techniques. Since the prime morphological ECG only contains morphological information, it is suitable for the classification of heart diseases and disorders conventionally associated with ECG morphology, such as myocardial ischemia, hypertrophies, bundle branch blocks, and the like. See Camm, et al., eds. (2006) THE ESC TEXTBOOK OF CARDIOVASCULAR MEDICINE, Blackwell, which is herein incorporated by reference.

As exemplified herein, application for the classification of the presence or absence of myocardial ischemia was created using the distribution function of length-1000 characteristic segment of the RT segment of ECG sampled at 1000 Hz. Observations of density functions of RT characteristic segment of about 400 subjects showed that the amount of total harmonic energy already allocated at or before the $6^{th}$ harmonic (or the $6^{th}$ distribution) is consistently about 31.4%, with a standard deviation of about 7.5%, and that the amount of the total harmonic energy already allocated at or before the $30^{th}$ harmonic (or the $30^{th}$ distribution) is consistently about 94.3%, with a standard deviation of about 3.7%.

Although the $6^{th}$ distribution function, the $30^{th}$ distribution function and the $499^{th}$ distribution function are exemplified herein, distribution functions of other harmonics may be used to classify or diagnose a subject as suffering from a heart disease or disorder in accordance with the present invention.

Employing the $6^{th}$ distribution (H[6]), the $30^{th}$ distribution (H[30]), and the $499^{th}$ distribution (H[499]) of the prime morphological ECG of various leads of a 12-lead ECG, various system models, such as linear systems, basis function systems, polynomial systems, clustering techniques, decision trees, Bayesian networks, neural network systems, fuzzy logic systems, evolutionary algorithms, and other methods known in the art, may be used to classify the ECG of a subject for the presence or absence of heart disease or disorders in accordance with the present invention. See Nelles (2000) NONLINEAR SYSTEM IDENTIFICATION, Springer: Berlin, which is herein incorporated by reference.

As exemplified herein, statistical decision trees and artificial neural network systems were created to classify the ECG of a subject for the presence or absence of ischemia.

The training sets employed herein were obtained from more than about 1000 subjects, which subjects have a diverse array of clinically diagnosed heart conditions. A training set of a subject comprises various inputs obtained from the subject which includes the computed ECG distribution functions, the specified resource-limited observation (RLO), and the desired output, e.g. the diagnosis of "normal" or "ischemic" based on a clinical diagnosis by an experienced cardiologist using resource-rich observation (RRO) methods known in the art. As used herein, an experienced cardiologist is a medical doctor who specializes in cardiology and has experience with conventional methods for diagnosing ischemia in a subject.

Statistical Decision Trees

Since a statistical decision tree is a formal stepwise process used in coming to a conclusion or making a judgment, it is suitable for classifying the ECG of a subject for the presence or absence of ischemia. See Breiman et al. (1984) CLASSIFICATION AND REGRESSION TREES, CRC, which is herein incorporated by reference.

Figure 19:
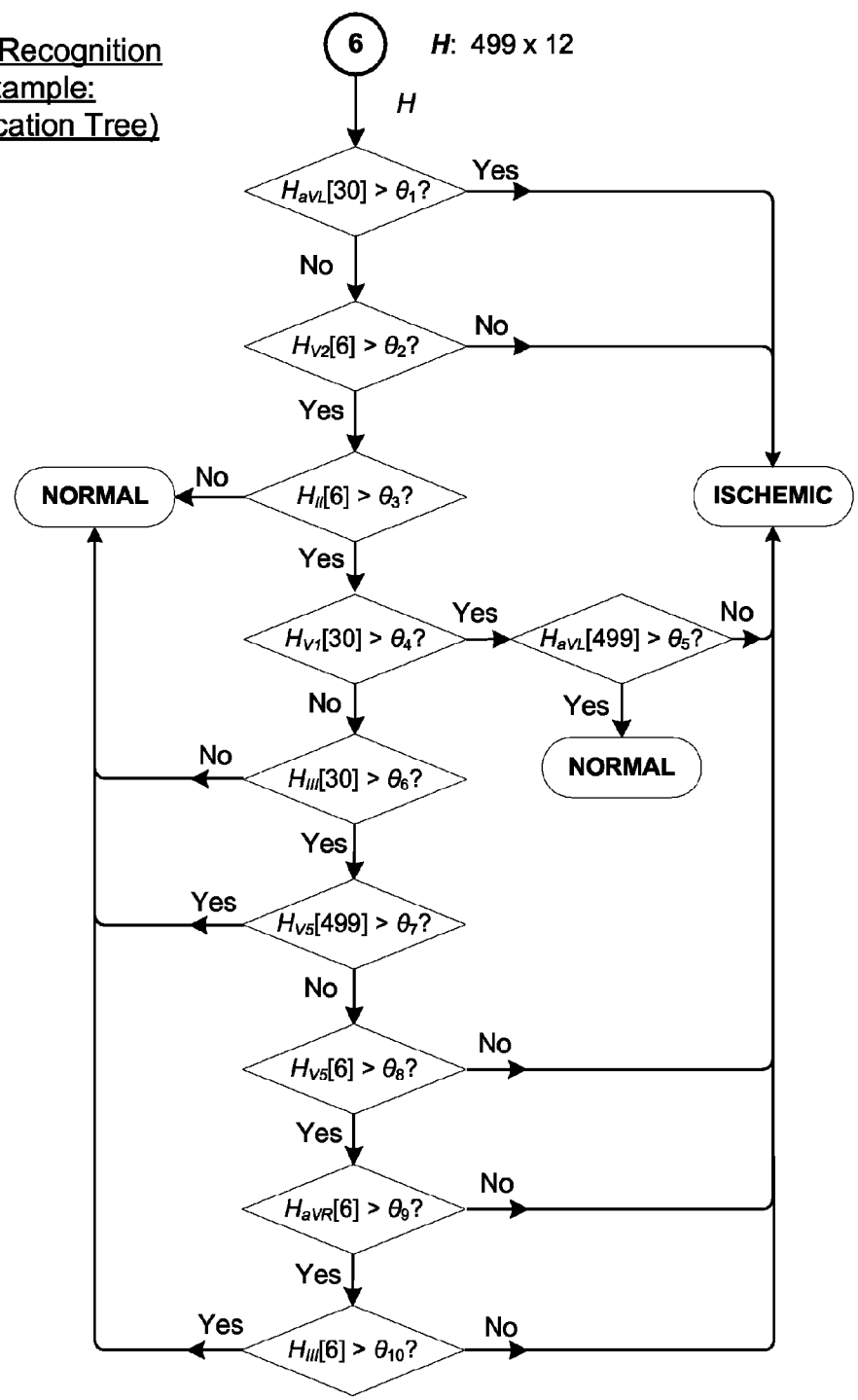
FIG. 19 is an example of a statistical decision tree using distribution functions of a prime morphological ECG for classifying or diagnosing a subject as suffering from myocardial ischemia.

Thus, in some embodiments, as outlined in FIG. 19, a subject is classified as being normal or ischemic as follows:

1. An ECG of a subject is considered "normal" (characterized as not suffering from a heart disease or disorder) if:

$H_{aVL}[30] \leq \theta_1$, $H_{V2}[6] > \theta_2$, and $H_{II}[6] \leq \theta_3$, or $H_{aVL}[30] \leq \theta_1$, $H_{V2}[6] > \theta_2$, $H_{II}[6] > \theta_3$, $H_{V1}[30] > \theta_4$, and $H_{aVL}[499] > \theta_5$, or $H_{aVL}[30] \leq \theta_1$, $H_{V2}[6] > \theta_2$, $H_{II}[6] > \theta_3$, $H_{V1}[30] \leq \theta_4$, and $H_{III}[30] \leq \theta_6$, or $H_{aVL}[30] \leq \theta_1$, $H_{V2}[6] > \theta_2$, $H_{II}[6] > \theta_3$, $H_{V1}[30] \leq \theta_4$, $H_{III}[30] > \theta_6$, and $H_{V5}[499] > \theta_7$, or $H_{aVL}[30] \leq \theta_1$, $H_{V2}[6] > \theta_2$, $H_{II}[6] > \theta_3$, $H_{V1}[30] \leq \theta_4$, $H_{III}[30] > \theta_6$, $H_{V5}[499] \leq \theta_7$, $H_{V5}[6] \leq \theta_8$, $H_{aVR}[6] > \theta_9$, and $H_{III}[6] > \theta_{10}$ 2. An ECG of a subject is considered "ischemic" (characterized as suffering from a heart disease or disorder such as myocardial ischemia) if:

$H_{aVL}[30] > \theta_1$, or $H_{aVL}[30] \leq \theta_1$, and $H_{V2}[6] \leq \theta_2$, or $H_{aVL}[30] \leq \theta_1$, $H_{V2}[6] > \theta_2$, $H_{II}[6] > \theta_3$, $H_{V1}[30] > \theta_4$, and $H_{aVL}[499] \leq \theta_5$, or $H_{aVL}[30] \leq \theta_1$, $H_{V2}[6] > \theta_2$, $H_{II}[6] > \theta_3$, $H_{V1}[30] \leq \theta_4$, $H_{III}[30] > \theta_6$, $H_{V5}[499] \leq \theta_7$, and $H_{V5}[6] \leq \theta_8$, or $H_{aVL}[30] \leq \theta_1$, $H_{V2}[6] > \theta_2$, $H_{II}[6] > \theta_3$, $H_{V1}[30] \leq \theta_4$, $H_{III}[30] > \theta_6$, $H_{V5}[499] \leq \theta_7$, $H_{V5}[6] > \theta_8$, and $H_{aVR}[6] \leq \theta_9$, or $H_{aVL}[30] \leq \theta_1$, $H_{V2}[6] > \theta_2$, $H_{II}[6] > \theta_3$, $H_{V1}[30] \leq \theta_4$, $H_{III}[30] > \theta_6$, $H_{V5}[499] \leq \theta_7$, $H_{V5}[6] > \theta_8$, $H_{aVR}[6] > \theta_9$, and $H_{III}[6] \leq \theta_{10}$ 3. The structure and threshold values ($\theta$) of the statistical decision tree may be readily obtained from the training of the input set and the desired output set by one skilled in the art using the statistical simulation software Statistica® available from StatSoft, Inc. (Tulsa, Okla.) and/or other methods and software known in the art.

Figure 20:
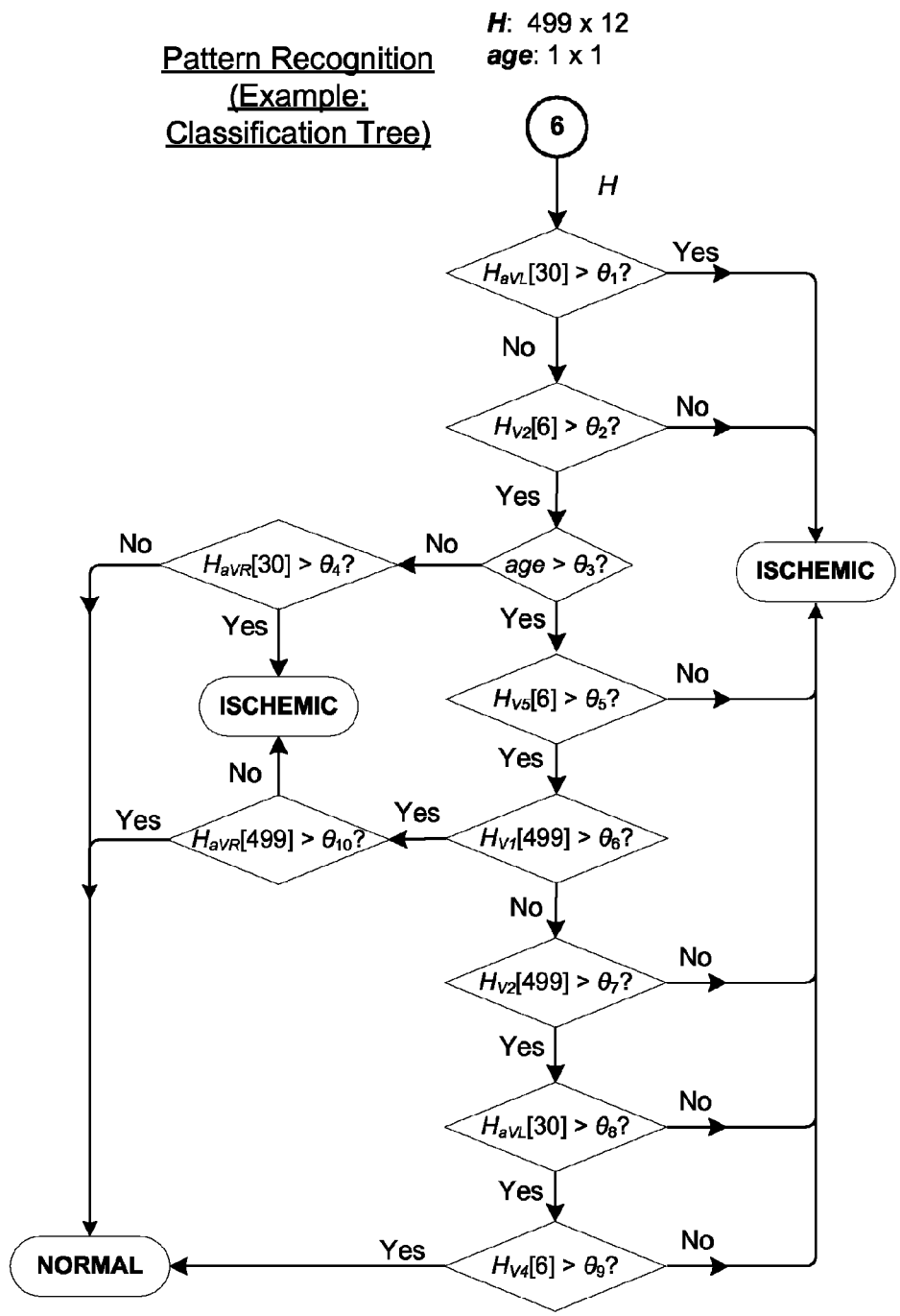
FIG. 20 is an example of a statistical decision tree using distribution functions of a prime morphological ECG and age for classifying or diagnosing a subject as suffering from myocardial ischemia.

In addition to distribution, other secondary factors, such as age or the presence or absence of a disease such as diabetes mellitus (DM), may be used. Other secondary factors include hypertension, smoking, dyslipidemia, and the like. Thus, in some embodiments, as outlined in FIG. 20, a subject is classified as being normal or ischemic as follows:

1. An ECG of a subject is considered "normal" (characterized as not suffering from a heart disease or disorder) if:

$H_{aVL}[30] \leq \theta_1$, $H_{V2}[6] > \theta_2$, age $\leq \theta_3$, and $H_{aVR}[30] \leq \theta_4$, or $H_{aVL}[30] \leq \theta_1$, $H_{V2}[6] > \theta_2$, age $> \theta_3$, $H_{V5}[6] > \theta_5$, $H_{V1}[499] > \theta_6$, and $H_{aVR}[499] > \theta_{10}$, or $H_{aVL}[30] \leq \theta_1$, $H_{V2}[6] > \theta_2$, age $> \theta_3$, $H_{V5}[6] > \theta_5$, $H_{V1}[499] \leq \theta_6$, $H_{V2}[499] > \theta_7$, $H_{aVL}[30] > \theta_7$, $H_{aVL}[30] > \theta_8$, and $H_{V4}[6] > \theta_9$.

2. An ECG of a subject is considered "ischemic" (characterized as suffering from a heart disease or disorder such as myocardial ischemia) if:

$H_{aVL}[30] > \theta_1$, or $H_{aVL}[30] > \theta_1$ and $H_{V2}[6] \leq \theta_2$, or $H_{aVL}[30] > \theta_1$, $H_{V2}[6] \leq \theta_2$, age $\leq \theta_3$, and $H_{aVR}[30] > \theta_4$, or $H_{aVL}[30] \leq \theta_1$, $H_{V2}[6] > \theta_2$, age $> \theta_3$, and $H_{V5}[6] \leq \theta_5$, or $H_{aVL}[30] \leq \theta_1$, $H_{V2}[6] > \theta_2$, age $> \theta_3$, $H_{V5}[6] > \theta_5$, $H_{V1}[499] > \theta_6$, and $H_{aVR}[499] \leq \theta_{10}$, or $H_{aVL}[30] \leq \theta_1$, $H_{V2}[6] > \theta_2$, age $> \theta_3$, $H_{V5}[6] > \theta_5$, $H_{V1}[499] \leq \theta_6$, and $H_{V2}[499] \leq \theta_7$, or $H_{aVL}[30] \leq \theta_1$, $H_{V2}[6] > \theta_2$, age $> \theta_3$, $H_{V5}[6] > \theta_5$, $H_{V1}[499] \leq \theta_6$, $H_{V2}[499] > \theta_7$, $H_{aVL}[30] > \theta_7$, and $H_{aVL}[30] \leq \theta_8$, or $H_{aVL}[30] \leq \theta_1$, $H_{V2}[6] > \theta_2$, age $> \theta_3$, $H_{V5}[6] > \theta_5$, $H_{V1}[499] \leq \theta_6$, $H_{V2}[499] > \theta_7$, $H_{aVL}[30] > \theta_7$, $H_{aVL}[30] > \theta_8$, and $H_{V4}[6] \leq \theta_9$.

3. The structure and threshold values ($\theta$) of the statistical decision tree may be readily obtained from the training of the input set and the desired output set by one skilled in the art using the statistical simulation software Statistica® available from StatSoft, Inc. (Tulsa, Okla.) and/or other methods and software known in the art.

Figure 21:
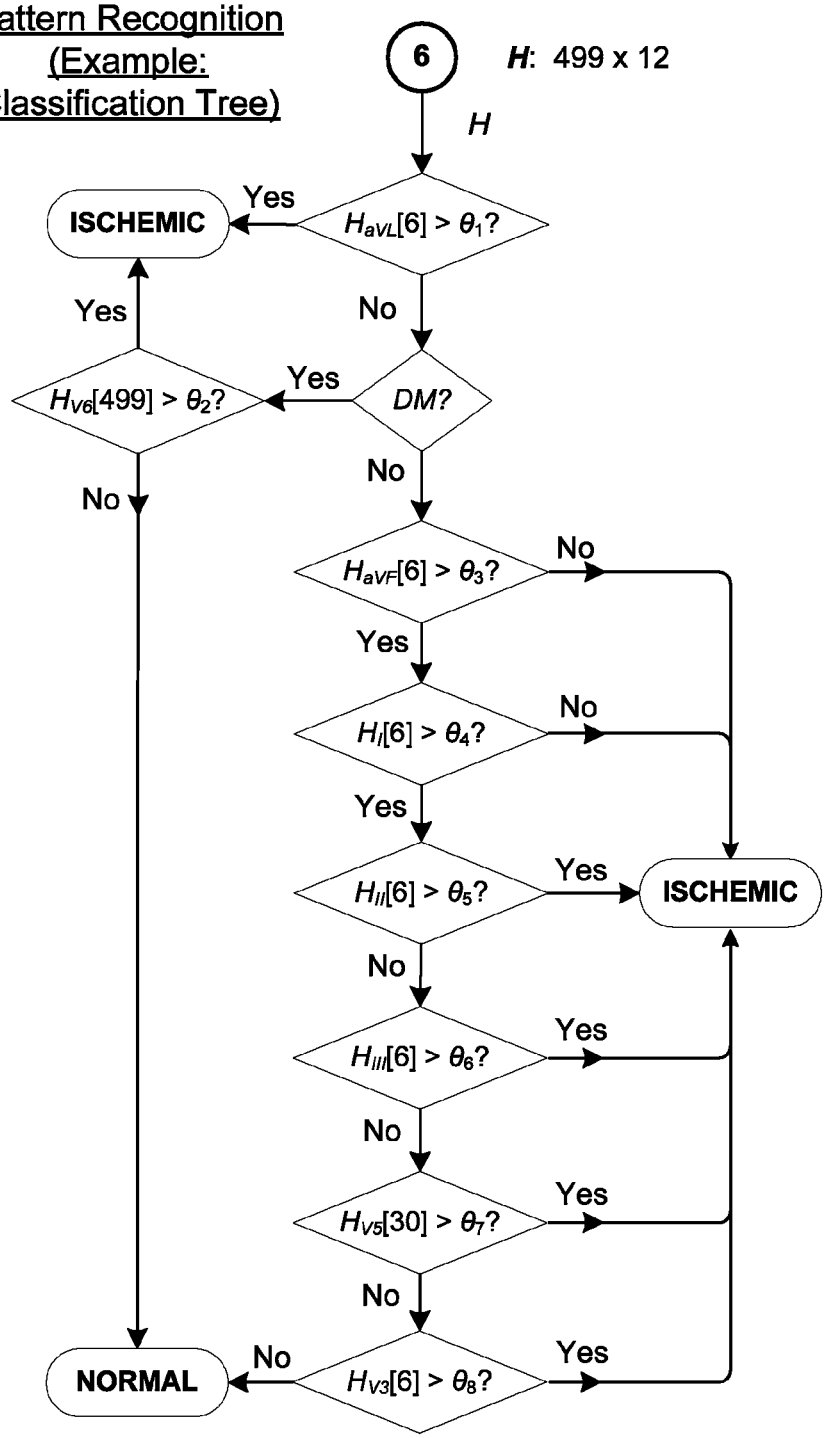
FIG. 21 is an example of a statistical decision tree using distribution functions of a prime morphological ECG and the presence or absence of diabetes mellitus for classifying or diagnosing a subject as suffering from myocardial ischemia.

Alternatively, as shown in FIG. 21, a subject is classified as being normal or ischemic as follows:

1. An ECG of a subject is considered "normal" (characterized as not suffering from a heart disease or disorder) if:

$H_{aVL}[6] \le \theta_1$, DM is positive, and $H_{V6}[499] \le \theta_2$, or $H_{aVL}[6] \le \theta_1$, DM is negative, $H_{aVF}[6] > \theta_3$, $H_I[6] > \theta_4$ $SH_I[6] > \theta_4$, $H_{II}[6] \le \theta_5$, $H_{III}[6] \le \theta_6$, $H_{V5}[30] \le \theta_7$, and $H_{V3}[6] \le \theta_8$ 2. An ECG of a subject is considered "ischemic" (characterized as suffering from a heart disease or disorder such as myocardial ischemia) if:

$H_{aVL}[6] > \theta_1$, $H_{aVL}[6] \le \theta_1$, DM is positive, and $H_{V6}[499] > \theta_2$, $H_{aVL}[6] \le \theta_1$, DM is negative, and $H_{aVF}[6] \le \theta_3$, $H_{aVL}[6] \le \theta_1$, DM is negative, $H_{aVF}[6] > \theta_3$, and $H_I[6] \le \theta_4$, $H_{aVL}[6] \le \theta_1$, DM is negative, $H_{aVF}[6] > \theta_3$, $H_I[6] > \theta_4$, and $H_{II}[6] > \theta_5$, $H_{aVL}[6] \le \theta_1$, DM is negative, $H_{aVF}[6] > \theta_3$, $H_I[6] > \theta_4$, $H_{II}[6] \le \theta_5$, and $H_{III}[6] > \theta_6$, $H_{aVL}[6] \le \theta_1$, DM is negative, $H_{aVF}[6] > \theta_3$, $H_I[6] > \theta_4$, $H_{II}[6] \le \theta_5$, $H_{III}[6] \le \theta_6$, and $H_{V5}[30] > \theta_7$, and/or $H_{aVL}[6] \le \theta_1$, DM is negative, $H_{aVF}[6] > \theta_3$, $H_I[6] > \theta_4 SH_I[6] > \theta_4$, $H_{II}[6] \le \theta_5$, $H_{III}[6] \le \theta_6$, $H_{V5}[30] \le \theta_7$, and $H_{V3}[6] > \theta_8$.

3. The structure and threshold values (A) of the statistical decision tree may be readily obtained from the training of the input set and the desired output set by one skilled in the art using the statistical simulation software Statistica® available from StatSoft, Inc. (Tulsa, Okla.) and/or other methods and software known in the art.

Artificial Neural Network Systems

An artificial neural network may be used in accordance with the present invention to analyze the ECG of a subject and classify the subject as suffering from ischemia or not or classifying the ECG as being indicative of ischemia or not. Suitable neural network systems include multi-layer preceptrons, radial basis systems, associative maps, Hopfield networks, and the like. See Gurney (1997) AN INTRODUCTION TO NEURAL NETWORKS, CRC, which is herein incorporated by reference.

Figure 23:
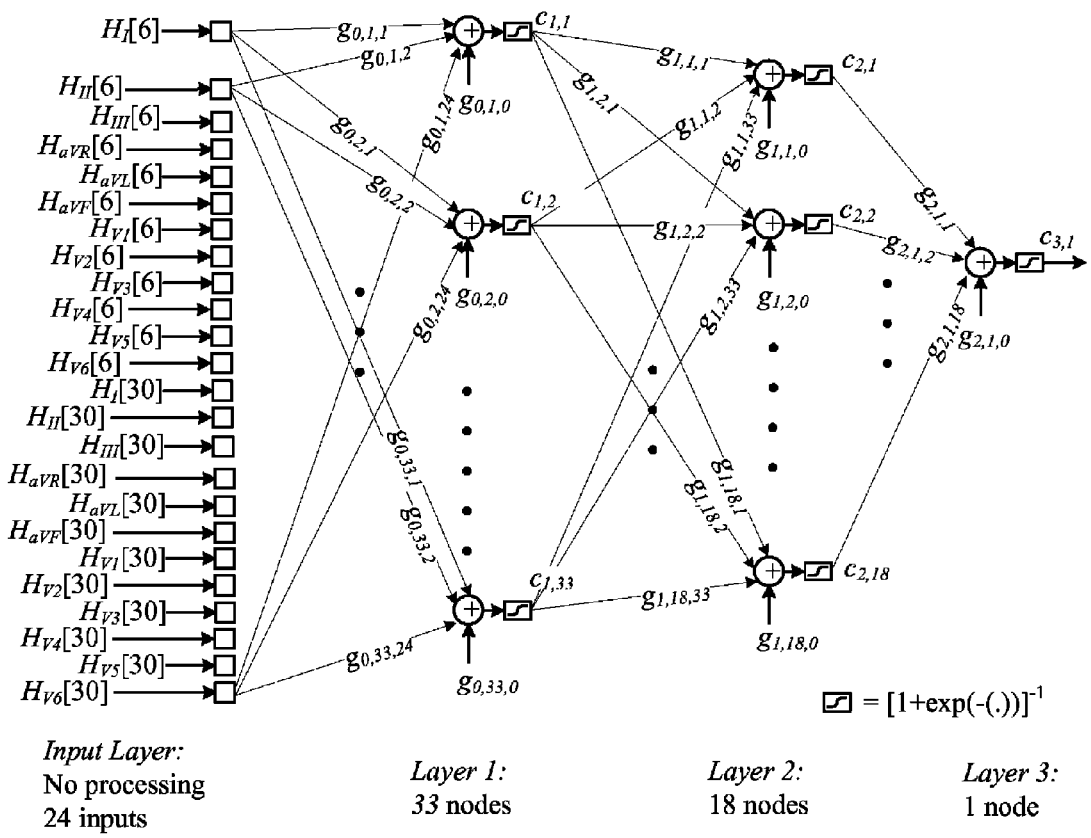
FIG. 23 is an example of an artificial neural network system of two processing layers using distribution functions of a prime morphological ECG for classifying or diagnosing a subject as suffering from myocardial ischemia.

In some embodiments, a multi-layer perceptron as set forth in FIG. 23 may be used to classify a subject or the ECG of the subject as being normal or ischemic as follows:

1. An ECG of a subject is considered "normal" (or the subject is characterized as not suffering from a heart disease or disorder) if:

$$c_{3,1} = \left[1 + \exp\left(-\sum_{l=1}^{18} c_{2,l} g_{2,1,l} - g_{2,1,0}\right)\right]^{-1} \le 0.5, \text{ where}$$

$$c_{2,l} = \left[1 + \exp\left(-\sum_{m=1}^{33} c_{1,m} g_{1,l,m} - g_{1,l,0}\right)\right]^{-1} \text{ for } l = 1, 2, \ldots, 18,$$

where $c_{1,m} = [1 + \exp(-Q_m - g_{0,m,0})]^{-1}$ for $m = 1, 2, \ldots, 33$, where $Q_m = H_I[6]g_{0,m,1} + H_{II}[6]g_{0,m,2} + H_{III}[6]g_{0,m,3} + H_{aVR}[6]g_{0,m,4} +$ $H_{aVL}[6]g_{0,m,5} + H_{aVF}[6]g_{0,m,6} + H_{V1}[6]g_{0,m,7} + H_{V2}[6]g_{0,m,8} +$ $H_{V3}[6]g_{0,m,9} + H_{V4}[6]g_{0,m,10} + H_{V5}[6]g_{0,m,11} + H_{V6}[6]g_{0,m,12} +$ $H_I[30]g_{0,m,13} + H_{II}[30]g_{0,m,14} + H_{III}[30]g_{0,m,15} + H_{aVR}[30]g_{0,m,16} +$ $H_{aVL}[30]g_{0,m,17} + H_{aVF}[30]g_{0,m,18} + H_{V1}[30]g_{0,m,19} + H_{V2}[30]g_{0,m,20} +$ $H_{V3}[30]g_{0,m,21} + H_{V4}[30]g_{0,m,22} + H_{V5}[30]g_{0,m,23} + H_{V6}[30]g_{0,m,24}$ for $m = 1, 2, \ldots, 33$.

2. An ECG of a subject is considered "ischemic" (or the subject is characterized as suffering from a heart disease or disorder such as myocardial ischemia) if:

$$c_{3,1} = \left[1 + \exp\left(-\sum_{l=1}^{18} c_{2,l} g_{2,1,l} - g_{2,1,0}\right)\right]^{-1} > 0.5, \text{ where}$$

$$c_{2,l} = \left[1 + \exp\left(-\sum_{m=1}^{33} c_{1,m} g_{1,l,m} - g_{1,l,0}\right)\right]^{-1} \text{ for } l = 1, 2, \ldots, 18,$$

where $c_{1,m} = [1 + \exp(-Q_m - g_{0,m,0})]^{-1}$ for $m = 1, 2, \ldots, 33$, where $Q_m = H_I[6]g_{0,m,1} + H_{II}[6]g_{0,m,2} + H_{III}[6]g_{0,m,3} + H_{aVR}[6]g_{0,m,4} +$ $H_{aVL}[6]g_{0,m,5} + H_{aVF}[6]g_{0,m,6} + H_{V1}[6]g_{0,m,7} + H_{V2}[6]g_{0,m,8} +$ $H_{V3}[6]g_{0,m,9} + H_{V4}[6]g_{0,m,10} + H_{V5}[6]g_{0,m,11} + H_{V6}[6]g_{0,m,12} +$ $H_I[30]g_{0,m,13} + H_{II}[30]g_{0,m,14} + H_{III}[30]g_{0,m,15} + H_{aVR}[30]g_{0,m,16} +$ $H_{aVL}[30]g_{0,m,17} + H_{aVF}[30]g_{0,m,18} + H_{V1}[30]g_{0,m,19} + H_{V2}[30]g_{0,m,20} +$ $H_{V3}[30]g_{0,m,21} + H_{V4}[30]g_{0,m,22} + H_{V5}[30]g_{0,m,23} + H_{V6}[30]g_{0,m,24}$ for $m = 1, 2, \ldots, 33$.

3. The architecture and weight values (g) of the multi-layer perceptron may be readily obtained by one skilled in the art from the training of the input set and the desired output set using the statistical simulation software Statistica® available from StatSoft, Inc. (Tulsa, Okla.) or other methods and software known in the art.

In addition to distribution, other secondary factors, e.g. age or the presence or absence of a disease such as diabetes mellitus (DM), hypertension, smoking, dyslipidemia, and the like may be used. Thus, in some embodiments, a subject or an ECG of a subject may be classified as being normal or ischemic using a multi-layer preceptron as outlined in FIG. 24 as follows:

1. An ECG of a subject is considered "normal" (or the subject is characterized as not suffering from a heart disease or disorder) if:

$$c_{3,1} = \left[1 + \exp\left(-\sum_{i=1}^{20} c_{2,1} g_{2,1,l} - g_{2,1,0}\right)\right]^{-1} \le 0.5, \text{ where}$$

$$c_{2,1} = \left[1 + \exp\left(-\sum_{m=1}^{50} c_{1,m} g_{1,i,m} - g_{1,i,0}\right)\right]^{-1} \text{ for } l = 1, 2, \ldots, 20,$$

where $c_{1,m} - [1 + \exp(-Q_m - g_{0,m,0})]^{-1}$ for $m = 1, 2, \ldots, 50$, where $Q_m =$ $H_I[6]g_{0,m,1} + H_{II}[6]g_{0,m,2} + H_{III}[6]g_{0,m,3} + H_{aVR}[6]g_{0,m,4} + H_{aVL}[6]g_{0,m,5} +$ $H_{aVF}[6]g_{0,m,6} + H_{V1}[6]g_{0,m,7} + H_{V2}[6]g_{0,m,8} + H_{V0}[6]g_{0,m,0} +$ $H_{V4}[6]g_{0,m,10} + H_{V5}[6]g_{0,m,11} + H_{V6}[6]g_{0,m,12} + H_I[30]g_{0,m,13} +$ -continued $H_{II}[30]g_{0,m,14} + H_{III}[30]g_{0,m,15} + H_{aVR}[30]g_{0,m,16} + H_{aVL}[30]g_{0,m,17} +$ $H_{aVF}[30]g_{0,m,18} + H_{V1}[30]g_{0,m,19} + H_{V2}[30]g_{0,m,20} +$ $H_{V3}[30]g_{0,m,21} + H_{V4}[30]g_{0,m,22} + H_{V5}[30]g_{0,m,23} + H_{V6}[30]g_{0,m,24} +$ $(age)g_{0,m,25} + (DM)g_{0,m,26}$ for $m = 1, 2, \ldots, 50$, where age is the age in years, and
DM=1, if there is presence of diabetes mellitus, and
DM=0, if there is no presence of diabetes mellitus.

2. An ECG of a subject is considered "ischemic" (or the subject is characterized as suffering from a heart disease or disorder such as myocardial ischemia) if:

$$c_{3,1} = \left[1 + \exp\left(-\sum_{l=1}^{20} c_{2,l}g_{2,1,l} - g_{2,1,0}\right)\right]^{-1} > 0.5, \text{ where}$$

$$c_{2,1} = \left[1 + \exp\left(-\sum_{m=1}^{50} c_{1,m}g_{1,l,m} - g_{1,l,0}\right)\right]^{-1} \text{ for } l = 1, 2, \ldots, 20,$$

where $c_{1,m} = [1 + \exp(-Q_m - g_{0,m,0})]^{-1}$ for $m = 1, 2, \ldots, 50$, where $Q_m = H_I[6]g_{0,m,1} + H_{II}[6]g_{0,m,2} + H_{III}[6]g_{0,m,3} + H_{aVR}[6]g_{0,m,4} +$ $H_{aVL}[6]g_{0,m,5} + H_{aVF}[6]g_{0,m,6} + H_{V1}[6]g_{0,m,7} + H_{V2}[6]g_{0,m,8} +$ $H_{V3}[6]g_{0,m,9} + H_{V4}[6]g_{0,m,10} + H_{V5}[6]g_{0,m,11} + H_{V6}[6]g_{0,m,12} +$ $H_I[30]g_{0,m,13} + H_{II}[30]g_{0,m,14} + H_{III}[30]g_{0,m,15} + H_{aVR}[30]g_{0,m,16} +$ $H_{aVL}[30]g_{0,m,17} + H_{aVF}[30]g_{0,m,18} + H_{V1}[30]g_{0,m,19} +$ $H_{V2}[30]g_{0,m,20} + H_{V3}[30]g_{0,m,21} + H_{V4}[30]g_{0,m,22} +$ $H_{V5}[30]g_{0,m,23} + H_{V6}[30]g_{0,m,24} + (age)g_{0,m,25} + (DM)g_{0,m,26}$ for $m = 1, 2, \ldots, 50$, where
age is the age in years, and
DM=1, if there is presence of diabetes mellitus, and
DM=0, if there is no presence of diabetes mellitus.

3. The architecture and weight values (g) of the multi-layer perceptron may be readily obtained by one skilled in the art from the training of the input set and the desired output set using the statistical simulation software Statistica® available from StatSoft, Inc. (Tulsa, Okla.) or other methods and software known in the art.

Figure 24:
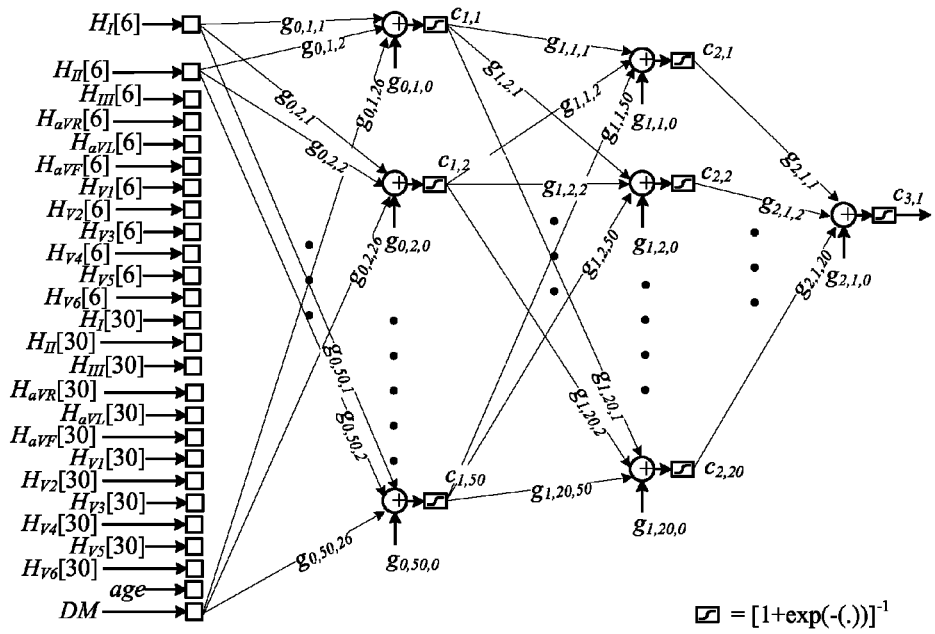
FIG. 24 is an example of an artificial neural network system of two processing layers using distribution functions of a prime morphological ECG, age, and the presence or absence of diabetes mellitus for classifying or diagnosing a subject as suffering from myocardial ischemia.
Figure 25:
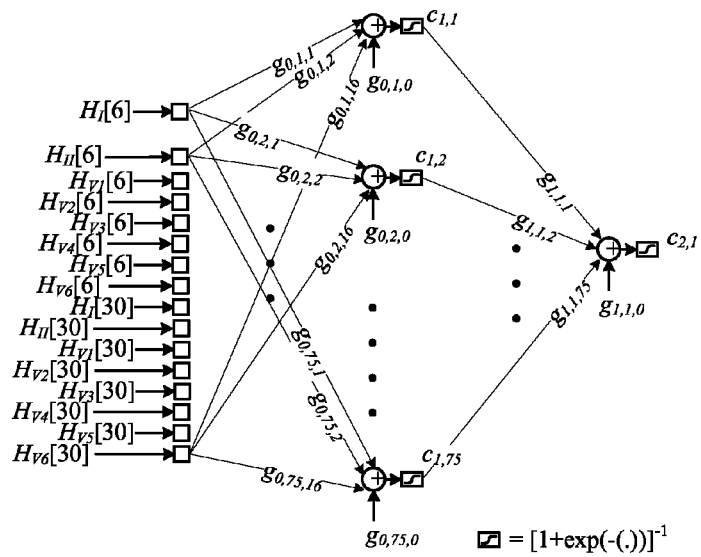
FIG. 25 is an example of an artificial neural network system of one processing layer using distribution functions of a prime morphological ECG for classifying or diagnosing a subject as suffering from myocardial ischemia.

Alternatively, a subject or an ECG may be classified as being normal or ischemic using a multi-layer preceptron having a structure that is different from that of FIG. 23 or 24 such as the structure shown in FIG. 25 as follows:

1. An ECG of a subject is considered "normal" (or the subject characterized as not suffering from a heart disease or disorder) if:

$$c_{2,1} = \left[1 + \exp\left(-\sum_{m=1}^{75} c_{1,m}g_{1,1,m} - g_{1,1,0}\right)\right]^{-1} \leq 0.5, \text{ where}$$

$c_{1,m} = [1 + \exp(-Q_m - g_{0,m,0})]^{-1}$ for $m = 1, 2, \ldots, 75$, where $Q_m = H_I[6]g_{0,m,1} + H_{II}[6]g_{0,m,2} + H_{V1}[6]g_{0,m,3} + H_{V2}[6]g_{0,m,4} +$ $H_{V3}[6]g_{0,m,5} + H_{V4}[6]g_{0,m,6} + H_{V5}[6]g_{0,m,7} + H_{V6}[6]g_{0,m,8} +$ $H_I[30]g_{0,m,9} + H_{II}[30]g_{0,m,10} + H_{V1}[30]g_{0,m,11} + H_{V2}[30]g_{0,m,12} +$ $H_{V3}[30]g_{0,m,13} + H_{V4}[30]g_{0,m,14} + H_{V5}[30]g_{0,m,15} + H_{V6}[30]g_{0,m,16}$ for $m = 1, 2, \ldots, 75$.

2. An ECG of a subject is considered "ischemic" (or the subject is characterized as suffering from a heart disease or disorder such as myocardial ischemia) if:

$$c_{2,1} = \left[1 + \exp\left(-\sum_{m=1}^{75} c_{1,m}g_{1,1,m} - g_{1,1,0}\right)\right]^{-1} > 0.5, \text{ where}$$

$c_{1,m} = [1 + \exp(-Q_m - g_{0,m,0})]^{-1}$ for $m = 1, 2, \ldots, 75$, where $Q_m = H_I[6]g_{0,m,1} + H_{II}[6]g_{0,m,2} + H_{V1}[6]g_{0,m,3} + H_{V2}[6]g_{0,m,4} +$ $H_{V3}[6]g_{0,m,5} + H_{V4}[6]g_{0,m,6} + H_{V5}[6]g_{0,m,7} + H_{V6}[6]g_{0,m,8} +$ $H_I[30]g_{0,m,9} + H_{II}[30]g_{0,m,10} + H_{V1}[30]g_{0,m,11} + H_{V2}[30]g_{0,m,12} +$ $H_{V3}[30]g_{0,m,13} + H_{V4}[30]g_{0,m,14} + H_{V5}[30]g_{0,m,15} + H_{V6}[30]g_{0,m,16}$ for $m = 1, 2, \ldots, 75$.

3. The architecture and weight values (g) of the multi-layer perceptron may be readily obtained by one skilled in the art from the training of the input set and the desired output set using the statistical simulation software Statistica® available from StatSoft, Inc. (Tulsa, Okla.) and/or other methods and software known in the art.

Data test sets obtained from 200 different subjects, which subjects have a diverse array of clinically diagnosed heart conditions. A data test set of a subject comprises various inputs obtained from the subject which includes the computed ECG distribution functions as disclosed herein, the specified resource-limited observations (RLO), and the desired output, e.g. the diagnosis of "normal" or "ischemic" based on a clinical diagnosis by an experienced cardiologist using resource-rich observation (RRO) methods known in the art. As used herein, an experienced cardiologist is a medical doctor who specializes in cardiology and has experience with conventional methods for diagnosing ischemia in a subject.

The performance of a classification system, such as a statistical decision tree or a multi-layer perceptron, for ischemia detection is defined by the predictive accuracy of the system for the testing set. The predictive accuracy is a number between 0 and 1, and is computed by dividing the number of correct actual outputs as compared with the desired outputs by the total number of the testing set (i.e. 200). The actual output of a subject is the result obtained from the classification system based the inputs.

More than ten multi-layer perceptron systems were trained and tested using the training sets and testing sets described herein using the statistical simulation software Statistica® available from StatSoft, Inc. (Tulsa, Okla.) and methods known in the art. Using the same training sets and the same data test sets as used in the multi-layer perceptrons, more than ten statistical decision trees were trained and tested using the statistical simulation software Statistica® available from StatSoft, Inc. (Tulsa, Okla.) and methods known in the art. The predictive accuracy of ten of the multi-layer perceptron systems were more than about 0.05 greater than the predictive accuracy of ten of the statistical decision trees. Therefore, according to the present invention, classifying a subject as having a heart disease or disorder such as ischemia using an artificial neural network is significantly more accurate than using a statistical decision tree.

B. Density of a Prime Arrhythmological ECG

After the prime arrhythmological ECG is created, ECG may be correlated to heart conditions using statistical pattern recognition techniques. Since the prime arrhythmological ECG only contains arrhythmological information, it is suitable for the classification of heart diseases and disorders conventionally associated with ECG arrhythmology, such as sinus arrhythmias, ischemia, infarction, and the like. See Thaler et al. (2003) THE ONLY EKG BOOK YOU'LL EVER NEED, Lippincott Williams & Wilkins, which is herein incorporated by reference.

For example, application for the classification of the presence or absence of an onset of myocardial infarction may be created using the distribution function of a sine waveform train, computed using the sinusoidal transform function the discrete Fourier transform. For example, there is correlation between the frequency-domain expression of arrhythmological information and the parasympathetic effect on the sinoatrial node. See Goldberger et al. (2001) Circulation 103 (15): 1977, which is herein incorporated by reference. Parasympathetic effect is an indicator and predictor for sudden cardiac death. See Kannenkeril et al. (2002) Am J Physiol Heart Circ Physiol 282: H2091, which is herein incorporated by reference. Hence, a statistical decision tree or an artificial neural network system may be similarly created that correlates between the frequency-domain distribution of a sine waveform train based on an ECG and the onset of sudden cardiac death.

IV. Device Structure

An ECG device known in the art may be used. In some embodiments, an ECG device is capable of providing at least 9 differential-input (DI) channels, a sampling rate of about 1000 Hz, a frequency response of about 500 Hz, an amplification factor of about 1000 times, a bit resolution of about 12 bits, a differential amplifier design, or a combination thereof. An example of a commercially available ECG device which may be employed in the methods and devices of the present invention is the Cardio Card 12-Lead ECG board (Nasiff Associates, Brewerton, N.Y.). Peripheral equipment and components such as ECG clamps, electrodes and cables known in the art may be used in accordance with the present invention.

In accordance with the present invention, any ECG device with the following specifications may be used:
  9 differential input (DI) channels or 10 single-ended (SE) channels
  A sampling rate of about 1000 Hz or greater
  A frequency response of about 500 Hz or greater
  A resolution (combination of signal amplification and signal bit representation) such that the voltage resolution is equal to or smaller than about 0.005 mV
  A Common Mode Rejection Ratio (CMRR) of about 100 dB or more
  An ECG electrode patient interface
  An ability to acquire about a 90-second sample of the simultaneous 10-channel data from a human subject and store into memory For example, the devices and systems of the present invention comprise a data acquisition module, a prime electrocardiogram converter and a computer which calculates at least one distribution function of a prime electrocardiogram. The data acquisition module receives an analog signal, magnifies the signal, samples the signal in time, and quantities the magnitude of the signal to provide a digital signal) comprises a lead ECG electrode patient interface (e.g. a 12-lead, a 16 lead, and the like), and differential input channels or single-ended channels (e.g. 9 or 15 differential input channels, 10 single-ended channels, and the like). The prime ECG converter and the distribution function computer each comprise a processor chip which provides a single-precision floating-point computation or a double-precision floating-point computation. The prime ECG converter or the distribution function computer may further comprise storage memory.

By solving the problem of harmonic disintegration and isolating the prime ECG, and by generating a statistical decision tree or an artificial neural network system that classifies a subject's prime ECG distributions, the present invention provides methods, systems and devices for detecting and diagnosing heart diseases and disorders. An overview of the method of the present invention is as follows:
  Acquiring and calculating the 12-lead ECG
  Identifying ECG beats and beat periods
  Creating the prime ECG
  Computing transform-domain densities
  Computing transform-domain distributions
  Classifying transform-domain distributions by heart condition One or more of the steps of the method of the present invention may be conducted using a software program, a computer, an electrocardiograph, an electrical circuit, a data acquisition module, a prime electrocardiogram converter, or a combination thereof. For example, software for the artificial neural network systems or statistical decision trees according to the present invention which is fixed on a computer readable medium may be used with a computer to classify the ECG distributions of an ECG obtained from a subject in accordance with the present invention. In some embodiments, the artificial neural network system may comprise a multi-layer perceptron written in the C Sharp computer language and compiled on Microsoft Visual C Studio available from Microsoft Corporation (Redmond, Wash.). In some embodiments, the artificial neural network system may comprise the Fast Artificial Neural Network Library written in the C computer language available open-source from the World Wide Web at leenissen.dk. In some embodiments, a computer or an electrocardiograph is used with the methods of the present invention.

In some embodiments, the present invention provides a method of treating a subject which comprises diagnosing or detecting a heart disease or disorder such as ischemia in the subject as described herein, and then, according to the diagnosis, treating the subject using methods known in the art. In some embodiments, the subject is a mammalian subject. In some embodiments, the subject is human.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:
1. A method for diagnosing or detecting a heart disease or disorder in a subject which comprises
  creating a prime electrocardiogram from a raw electrocardiogram of the subject, obtaining harmonics from the prime electrocardiogram by performing Fourier analysis;

obtaining a plurality of density functions for the harmonics in a range of harmonics of the prime electrocardiogram, wherein the density function refers to the sampling rate multiplied by the harmonic peak energy divided by the length of the period of the prime electrocardiogram;

summing the plurality of density functions to give at least one distribution function; and determining the presence or absence of the heart disease or disorder based on whether the distribution function is indicative of the heart disease or disorder by using an artificial neural network system.

2. The method of claim 1, wherein the prime electrocardiogram is a prime morphological electrocardiogram.

3. The method of claim 2, wherein the prime morphological electrocardiogram is obtained by acquiring a raw electrocardiogram as electronic data from the subject;

selecting at least one characteristic segment or at least one characteristic window; and isolating the characteristic segment or the characteristic window by removing information extraneous to the characteristic segment or the characteristic window.

4. The method of claim 3, wherein the characteristic segment is a QT segment, an RT segment, or a PR segment or the characteristic window includes part or all of a T-wave or part or all of a PQRST interval.

5. The method of claim 3, which further comprises refining the characteristic segment or the characteristic window by averaging the characteristic segment or the characteristic window.

6. The method of claim 5, which further comprises repeating the averaged characteristic window or the averaged characteristic segment by N times, wherein N is any positive integer.

7. The method of claim 3, wherein the isolated characteristic segment is a plurality of isolated characteristic segments in series or a plurality of isolated characteristic windows in series.

8. The method of claim 1, wherein the heart disease or disorder is myocardial ischemia.

9. The method of claim 1, which further comprises determining a secondary factor such as the subject's age or whether the subject suffers from diabetes mellitus.

10. The method of claim 9, wherein the following combination of distribution functions

A)

$$c_{3,1} = \left[1 + \exp\left(-\sum_{l=1}^{20} c_{2,l} g_{2,1,l} - g_{2,1,0}\right)\right]^{-1} \leq 0.5, \text{ where}$$

$$c_{2,l} = \left[1 + \exp\left(-\sum_{m=1}^{50} c_{1,m} g_{1,l,m} - g_{1,l,0}\right)\right]^{-1} \text{ for } l = 1, 2, \ldots, 20,$$

where $c_{1,m} = [1 + \exp(-Q_m - g_{0,m,0})]^{-1}$ for $m = 1, 2, \ldots, 50$, where $Q_m = H_I[6]g_{0,m,1} + H_{II}[6]g_{0,m,2} + H_{III}[6]g_{0,m,3} + H_{aVR}[6]g_{0,m,4} +$ $H_{aVL}[6]g_{0,m,5} + H_{aVF}[6]g_{0,m,6} + H_{V1}[6]g_{0,m,7} + H_{V2}[6]g_{0,m,8} +$ $H_{V3}[6]g_{0,m,9} + H_{V4}[6]g_{0,m,10} + H_{V5}[6]g_{0,m,11} + H_{V6}[6]g_{0,m,12} +$ $H_I[30]g_{0,m,13} + H_{II}[30]g_{0,m,14} + H_{III}[30]g_{0,m,15} + H_{aVR}[30]g_{0,m,16} +$ -continued $H_{aVL}[30]g_{0,m,17} + H_{aVF}[30]g_{0,m,18} + H_{V1}[30]g_{0,m,19} +$ $H_{V2}[30]g_{0,m,20} + H_{V3}[30]g_{0,m,21} + H_{V4}[30]g_{0,m,22} +$ $H_{V5}[30]g_{0,m,23} + H_{V6}[30]g_{0,m,24} + (\text{age})g_{0,m,25} + (DM)g_{0,m,26}$ for $m = 1, 2, \ldots, 50$, where age is the age in years, and DM=1, if there is presence of diabetes mellitus, or DM=0, if there is no presence of diabetes mellitus;

B)

$$c_{2,1} = \left[1 + \exp\left(-\sum_{l=1}^{75} c_{1,m} g_{1,1,m} - g_{1,1,0}\right)\right]^{-1} \leq 0.5, \text{ where}$$

$c_{1,m} = [1 + \exp(-Q_m - g_{0,m,0})]^{-1}$ for $m = 1, 2, \ldots, 75$, where $Q_m = H_I[6]g_{0,m,1} + H_{II}[6]g_{0,m,2} + H_{V1}[6]g_{0,m,3} + H_{V2}[6]g_{0,m,4} +$ $H_{V3}[6]g_{0,m,5} + H_{V4}[6]g_{0,m,6} + H_{V5}[6]g_{0,m,7} + H_{V6}[6]g_{0,m,8} +$ $H_I[30]g_{0,m,9} + H_{II}[30]g_{0,m,10} + H_{V1}[30]g_{0,m,11} + H_{V2}[30]g_{0,m,12} +$ $H_{V3}[30]g_{0,m,13} + H_{V4}[30]g_{0,m,14} + H_{V5}[30]g_{0,m,15} + H_{V6}[30]g_{0,m,16}$ for $m = 1, 2, \ldots, 75$; or

C)

$$c_{2,1} = \left[1 + \exp\left(-\sum_{m=1}^{75} c_{1,m} g_{1,1,m} - g_{1,1,0}\right)\right]^{-1} > 0.5, \text{ where}$$

$c_{1,m} = [1 + \exp(-Q_m - g_{0,m,0})]^{-1}$ for $m = 1, 2, \ldots, 75$, where $Q_m =$ $H_I[6]g_{0,m,1} + H_{II}[6]g_{0,m,2} + H_{V1}[6]g_{0,m,3} + H_{V2}[6]g_{0,m,4} + H_{V3}[6]g_{0,m,5} +$ $H_{V4}[6]g_{0,m,6} + H_{V5}[6]g_{0,m,7} + H_{V6}[6]g_{0,m,8} + H_I[30]g_{0,m,9} +$ $H_{II}[30]g_{0,m,10} + H_{V1}[30]g_{0,m,11} + H_{V2}[30]g_{0,m,12} +$ $H_{V3}[30]g_{0,m,13} + H_{V4}[30]g_{0,m,14} + H_{V5}[30]g_{0,m,15} +$ $H_{V6}[30]g_{0,m,16}$ for $m = 1, 2, \ldots, 75$ is indicative of the absence of the heart disease or disorder.

11. The method of claim 9, wherein the following combination of distribution functions $$c_{3,1} = \left[1 + \exp\left(-\sum_{l=1}^{20} c_{2,1} g_{2,1,i} - g_{2,1,0}\right)\right]^{-1} > 0.5, \text{ where}$$

$$c_{2,1} = \left[1 + \exp\left(-\sum_{m=1}^{50} c_{1,m} g_{1,l,m} - g_{1,l,0}\right)\right]^{-1} \text{ for}$$

$l = 1, 2, \ldots, 20$, where $c_{1,m} = [1 + \exp(-Q_m - g_{0,m,0})]^{-1}$ for $m = 1, 2, \ldots, 50$, where $Q_m =$ $H_I[6]g_{0,m,1} + H_{II}[6]g_{0,m,2} + H_{III}[6]g_{0,m,3} + H_{aVR}[6]g_{0,m,4} + H_{aVL}[6]g_{0,m,5} +$ $H_{aVF}[6]g_{0,m,6} + H_{V1}[6]g_{0,m,7} + H_{V2}[6]g_{0,m,8} + H_{V3}[6]g_{0,m,9} +$ $H_{V4}[6]g_{0,m,10} + H_{V5}[6]g_{0,m,11} + H_{V6}[6]g_{0,m,12} + H_I[30]g_{0,m,13} +$ -continued $$H_{II}[30]g_{0,m,14} + H_{III}[30]g_{0,m,15} + H_{aVR}[30]g_{0,m,16} +$$
$$H_{aVF}[30]g_{0,m,18} + H_{V1}[30]g_{0,m,19} + H_{V2}[30]g_{0,m,20} +$$
$$H_{V3}[30]g_{0,m,21} + H_{V4}[30]g_{0,m,22} + H_{V5}[30]g_{0,m,23} + H_{V6}[30]g_{0,m,24} +$$
$$(age)g_{0,m,25} + (DM)g_{0,m,26} \text{ for } m = 1, 2, \ldots, 50, \text{ where}$$

age is the age in years, and
DM=1, if there is presence of diabetes mellitus, or
DM=0, if there is no presence of diabetes mellitus
is indicative of the presence of the heart disease or disorder.

12. The method of claim 1, wherein a plurality of distribution functions greater than a set threshold value is indicative of the presence of the heart disease or disorder.

13. The method of claim 1, wherein the following combination of distribution functions $$c_{3,1} = \left[1 + \exp\left(-\sum_{l=1}^{18} c_{2,l}g_{2,1,l} - g_{2,1,0}\right)\right]^{-1} \leq 0.5, \text{ where}$$

$$c_{2,l} = \left[1 + \exp\left(-\sum_{m=1}^{33} c_{1,m}g_{1,l,m} - g_{1,l,0}\right)\right]^{-1} \text{ for } l = 1, 2, \ldots, 18,$$

where $$c_{1,m} = [1 + \exp(-Q_m - g_{0,m,0})]^{-1} \text{ for } m = 1, 2, \ldots, 33, \text{ where}$$

$$Q_m = H_I[6]g_{0,m,1} + H_{II}[6]g_{0,m,2} + H_{III}[6]g_{0,m,3} + H_{aVR}[6]g_{0,m,4} +$$
$$H_{aVL}[6]g_{0,m,5} + H_{aVF}[6]g_{0,m,6} + H_{V1}[6]g_{0,m,7} + H_{V2}[6]g_{0,m,8} +$$
$$H_{V3}[6]g_{0,m,9} + H_{V4}[6]g_{0,m,10} + H_{V5}[6]g_{0,m,11} + H_{V6}[6]g_{0,m,12} +$$
$$H_I[30]g_{0,m,13} + H_{II}[30]g_{0,m,14} + H_{III}[30]g_{0,m,15} + H_{aVR}[30]g_{0,m,16} +$$
$$H_{aVL}[30]g_{0,m,17} + H_{aVF}[30]g_{0,m,18} + H_{V1}[30]g_{0,m,19} + H_{V2}[30]g_{0,m,20} +$$
$$H_{V3}[30]g_{0,m,21} + H_{V4}[30]g_{0,m,22} + H_{V5}[30]g_{0,m,23} + H_{V6}[30]g_{0,m,24}$$
$$\text{for } m = 1, 2, \ldots, 33.$$

is indicative of the absence of the heart disease or disorder.

14. The method of claim 1, wherein the following combination of distribution functions $$c_{3,1} = \left[1 + \exp\left(-\sum_{l=1}^{18} c_{2,l}g_{2,1,l} - g_{2,1,0}\right)\right]^{-1} > 0.5, \text{ where}$$

$$c_{2,l} = \left[1 + \exp\left(-\sum_{m=1}^{33} c_{1,m}g_{1,l,m} - g_{1,l,0}\right)\right]^{-1} \text{ for } l = 1, 2, \ldots, 18,$$

where $$c_{1,m} = [1 + \exp(-Q_m - g_{0,m,0})]^{-1} \text{ for } m = 1, 2, \ldots, 33, \text{ where}$$

$$Q_m = H_I[6]g_{0,m,1} + H_{II}[6]g_{0,m,2} + H_{III}[6]g_{0,m,3} + H_{aVR}[6]g_{0,m,4} +$$
$$H_{aVL}[6]g_{0,m,5} + H_{aVF}[6]g_{0,m,6} + H_{V1}[6]g_{0,m,7} + H_{V2}[6]g_{0,m,8} +$$
$$H_{V3}[6]g_{0,m,9} + H_{V4}[6]g_{0,m,10} + H_{V5}[6]g_{0,m,11} + H_{V6}[6]g_{0,m,12} +$$
$$H_I[30]g_{0,m,13} + H_{II}[30]g_{0,m,14} + H_{III}[30]g_{0,m,15} + H_{aVR}[30]g_{0,m,16} +$$
$$H_{aVL}[30]g_{0,m,17} + H_{aVF}[30]g_{0,m,18} + H_{V1}[30]g_{0,m,19} + H_{V2}[30]g_{0,m,20} +$$
$$H_{V3}[30]g_{0,m,21} + H_{V4}[30]g_{0,m,22} + H_{V5}[30]g_{0,m,23} + H_{V6}[30]g_{0,m,24}$$
$$\text{for } m = 1, 2, \ldots, 33.$$

is indicative of the presence of the heart disease or disorder.

15. The method of claim 1, wherein the prime electrocardiogram is created using a beat marker.

16. The method of claim 15, wherein in the marker is selected using a vectorcardiogram.

17. A system or device for detecting or diagnosing a subject as suffering from a heart disease or disorder comprising
an electrocardiograph machine which obtains a raw electrocardiogram from the subject;
a data acquisition module which converts the raw electrocardiogram into a raw digital electrocardiogram;
a prime electrocardiogram which converts the raw digital electrocardiogram into a prime electrocardiogram;
a computer which calculates at least one distribution function of the prime electrocardiogram, and
an artificial neural network system which determines whether the distribution function is indicative of the heart disease or disorder.

18. The system or device of claim 17, wherein the distribution function is a sum of a plurality of density functions for harmonics in a range of harmonics of the prime electrocardiogram which are obtained by performing Fourier analysis, and wherein the density function refers to the sampling rate multiplied by the harmonic peak energy divided by the length of the period of the prime electrocardiogram.

19. The system or device of claim 17, wherein the prime electrocardiogram converter converts the raw electrocardiogram into the prime electrocardiogram using a beat marker that was identified using a vectorcardiogram.

20. A method for diagnosing or detecting a heart disease or disorder in a subject which comprises
creating a prime electrocardiogram from a raw electrocardiogram of the subject using a beat marker that was identified using a vectorcardiogram,
obtaining harmonics from the prime electrocardiogram by performing Fourier analysis;
obtaining a plurality of density functions for the harmonics in a range of harmonics of the prime electrocardiogram, wherein the density function refers to the sampling rate multiplied by the harmonic peak energy divided by the length of the period of the prime electrocardiogram;
summing the plurality of density functions to give at least one distribution function; and
determining the presence or absence of the heart disease or disorder based on whether the distribution function is indicative of the heart disease or disorder by using an artificial neural network system.

* * * * *